(12) United States Patent
Murray et al.

(10) Patent No.: US 6,518,411 B1
(45) Date of Patent: *Feb. 11, 2003

(54) RGS COMPOSITIONS AND THERAPEUTIC AND DIAGNOSTIC USES THEREFOR

(75) Inventors: Jeffrey C. Murray, Iowa City, IA (US); Elena Semina, Coralville, IA (US)

(73) Assignee: University of Iowa, Iowa City, IA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/754,477

(22) Filed: Nov. 22, 1996

(51) Int. Cl.$^7$ .............................................. C07H 21/04
(52) U.S. Cl. .................. 536/23.1; 536/23.5; 536/24.31; 536/24.33; 536/24.5
(58) Field of Search ............................... 536/23.5, 23.1, 536/24.31, 24.33, 24.5; 435/325; 935/9

(56) References Cited

PUBLICATIONS

1994–1995 Promega Catalog p. 167.*
Accession No. T 64905 Mar. 7, 1995.*
Accession No. W5 9350, Jun. 6, 1996.*
Accession No. W77 302, Jun. 20, 1996.*
Accession No. AA 32943 Aug. 22, 1996.*
Hillier et al, GeneBank, Accession No. T64905, H13139, AA056634, N69394, T61705, 1995.*
Jin, Y. et al. Nature, 372 (6508): 780–783, 1994.*
Szeto, DP. et al. PNAS, USA, 93(15): 7706–7710, 1996.*
Matthews, B. "Genetic and Structural Anaylsis of the Protein Stability Problem", Perspectives in Biochemistry, Hans Neurath, Ed., vol. 1, pp. 6–9, 1989.*
Mathews and VanHolde, Biochemistry (Textbook), 2nd edition, pp. 165–171, 1996.*
Frisch et al, "A Soluble Immunoglobin Variable domain without a Disulfide Bridge . . . ", Biol. Chem. Hoppe–Seyler, vol. 375, pp. 353–356, 1994.*
Kim et al, "Restoring allosterism with compensatory mutaions in hemoglobin", PNAS, vol. 91, pp. 11547–11551, Nov. 1994.*
Semina, E.V. , et al. "Cloning and characterization of a novel human homeobox gene involved in the Reiger syndrome and its mouse homolog" (ABSTRACT) *American J. of Human Genetics*, vol. 59, #4 (suppl.) pA9, No. 34; Oct., 1996.
Hillier, L., et al. GENBANK Accession No. H95407 Nov. 25, 1996.
Lamonerie, T. et al. "Ptx1, a biocoid–related homeo box transcription factor involved in transcription of the pro–o-piomelanocortin gene." *Genes & Development* 10:1284–1295, 1996.
Gordon, D.F., et al. "Human Cart–1: structural organization, chromosomal localization, and functional analysis of a cartilage–specific homeodomain cDNA." *DNA Cell Biol.* 15(7):531–541, 1996.
Wright, D.A., et al. GENBANK Accession No. U15276 Oct. 11, 1994.

* cited by examiner

*Primary Examiner*—Anthony C. Caputa
*Assistant Examiner*—Karen A. Canella
(74) *Attorney, Agent, or Firm*—Isabelle Clauss; Foley Hoag, LLP

(57) ABSTRACT

The present invention relates to the discovery of novel genes encoding RGS polypeptides. Therapeutics, diagnostics and screening assays based on these molecules are also disclosed.

9 Claims, 14 Drawing Sheets

(A)
```
1    CGAGAAAGCT  GGAGAGGAGC  AGAAAGAAAC  TGCCAGTGGC  GGCTAGATTT
51   CGGAGGCCCC  AGTGCACCCG  TGGACTCCTT  CGGAACTTGG  CACCCTCAGG
101  AGCCCTGCAG  TCCTCTCAGG  CCCGGCTTTC  GGGCGCTTGC  CGTGCAGCCG
151  GAGGCTCGGC  TCGCTGGAAA  TCGCCCCGGG  AAGCAGTGGG  ACGCGGAGAC
201  AGCAGCTCTC  TCCCGGTAGC  CGgtaagtgg  agg····
                                        ·······cgc  ttcttacagc cttcctttct  tctgttttgc  agATAACGGG  GAAATG GAG ACC AAC TGC
                                        Met Glu Thr Asn Cys
```

```
242  CGC AAA CTG GTG TCG GCG TGT CTG CAA TTA Ggtaagaaccccttctcc
     Arg Lys Leu Val Ser Ala Cys Val Gln Leu
                                                            Glu
                                              #              G G
     tgcc····cgggtcatcggac····tgtgtttcagttttcagAG AAA GAT AAA AGC
                                              #Glu Lys Asp Lys Ser
```

```
                A   A                  T                       C
286  CAG CAG GGG AAG AAT GAG GAC GTG GGC GCC GAG GAC CCG TCT AAG
     Gln Gln Gly Lys Asn Glu Asp Val Gly Ala Glu Asp Pro Ser Lys

C C         A           T   C   T
331  AAG AAG CGG CAA AGG CGG CAG CGG ACT CAC TTT ACC AGC CAG CAG
     Lys Lys Arg Gln Arg Arg Gln Arg Thr His Phe Thr Ser Gln Gln

G           A               A                   A
374  CTC CAG CAG CTG GAG GCC ACT TTC CAG AGG AAC CGC TAC CCG GAC
     Leu Gln Gln Leu Glu Ala Thr Phe Gln Arg Asn Arg Tyr Pro Asp
             A*
             Gln

T
413  ATG TCC ACA CGC GAA GAA ATC GCT GTG TGG ACC AAC CTT ACG GAA
     Met Ser Thr Arg Glu Glu Ile Ala Val Trp Thr Asn Leu Thr Glu
             C*
             Pro
```

```
ag
464  GCC CGA GTC CGGgtgagccagcacggagtctgggagg········ctgtttgctcccttgc
     Ala Arg Val Arg   c*

C
     cccaaccgcccccag GTT TGG TTC AAG AAT CGT CGG GCC AAA TGG AGA
                g*  Val Trp Phe Lys Asn Arg Arg Ala Lys Trp Arg
                                                        C*
                                                        Pro
```

FIG. 1A

```
                  C     A                              G                            T
509  AAG AGG GAG CGC   AAC CAG CAG GCC GAG CTA TGC AAG AAT GGC TTC
     Lys Arg Glu Arg   Asn Gln Gln Ala Glu Leu Cys Lys Asn Gly Phe
                              C
554  GGG CCG CAG TTC AAT GGG CTC ATG CAG CCC TAC GAC GAC ATG TAC
     Gly Pro Gln Phe Asn Gly Leu Met Gln Pro Tyr Asp Asp Met Tyr
         C           G               T               C   G   A
559  CCA GGC TAT TCC TAC AAC AAC TGG GCC GCC AAG GGC CTT ACA TCC
     Pro Gly Tyr Ser Tyr Asn Asn Trp Ala Ala Lys Gly Leu Thr Ser
                                     A
                                  Stop Codon G   T   G                                              C
644  GCC TCC CTA TCC ACC AAG AGC TTC CCC TTC TTC AAC TCT ATG AAC
     Ala Ser Leu Ser Thr Lys Ser Phe Pro Phe Phe Asn Ser Met Asn
             T           G   T       T           G           C
689  GTC AAC CCC CTG TCA TCA CAG AGC ATG TTT TCC CCA CCC AAC TCT
     Val Asn Pro Leu Ser Ser Gln Ser Met Phe Ser Pro Pro Asn Ser
             A   T       T                              C   G
734  ATC TCG TCC ATG AGC ATG TCG TCC AGC ATG GTG CCC TCA GCA GTG
     Ile Ser Ser Met Ser Met Ser Ser Ser Met Val Pro Ser Ala Val
                 C                       C       T
779  ACA GGC GTC CCG GGC TCC AGT CTC AAC AGC CTG AAT AAC TTG AAC
     Thr Gly Val Pro Gly Ser Ser Leu Asn Ser Leu Asn Asn Leu Asn
                     C                               C       C
824  AAC CTG AGT AGC CCG TCG CTG AAT TCC GCG GTG CCG ACG CCT GCC
     Asn Leu Ser Ser Pro Ser Leu Asn Ser Ala Val Pro Thr Pro Ala
                                                 C                   A
869  TGT CCT TAC GCG CCG CCG ACT CCT CCG TAT GTT TAT AGG GAC ACG
     Cys Pro Tyr Ala Pro Pro Thr Pro Pro Tyr Val Tyr Arg Asp Thr
914  TGT AAC TCG AGC CTG GCC AGC CTG AGA CTG AAA GCA AAG CAG CAC
     Cys Asn Ser Ser Leu Ala Ser Leu Arg Leu Lys Ala Lys Gln His
     ----------------------------------------------------------------
                                             Asn
                                              C
959  TCC AGC TTC GGC TAC GCC AGC GTG CAG AAA CCG GCC TCC AAC CTG
     Ser Ser Phe Bly Tyr Ala Ser Val Gln Lys Pro Ala Ser Asn Leu
     ---
                                                 C           G
1004 AGT GCT TGC CAG TAT GCA GTG GAC CGG CCC GTG TGAG CCGCACCCAC
     Ser Ala Cys Gln Tyr Ala Val Asp Arg Pro Val Stop
```

FIG. 1A-1

1051 AGCGCCGGGA TCCTAGGACC TTGCCGGATG GGGCAACTCC GCCCTTGAAA
1101 GACTGGGAAT TATGCTAGAA GGTCGTGGGC ACTAAAGAAA GGGAGAGAAA
1151 GAGAAGCTAT ATAGAGAAAA GGAAACCACT GAATCAAAGA GAGAGCTCCT
1201 TTGATTTCAA AGGGATGTCC TCAGTGTCTG ACATCTTTCA CTACAAGTAT
1251 TTCTAACAGT TGCAAGGACA CATACACAAA CAAATGT*TTT* *GACTGGATAT*
1301 *GACATTTTAA* *CATTACTATA* *AGCTTGTTAT* *TTTTTAAGTT* *TAGCATTGTT*
1351 *AACATTTAAA* *TGACTGAAAG* *GATGTATATA* *TATCGAAATG* *TCAAATTAAT
1401 *TTTATAAAAG* *CAGTTGTTAG* *TAATATCACA* *ACAGTGTTTT* *TAAAGGTTAG*
1451 *GCTTTA**AAAT* *AAA**GCATGTT* *ATACAGAAGC* *GATTAGGATT* *TTTCGCTTGC*
1501 *GAGCAAGGGA* *GTGTATATAC* *TAAATGCCAC* *ACTGTATGTT* *TCTAACATAT*
1551 *TATTATTATT* ATAAAAATG TGTGAATATC AGTTTTAGAA TAGTTTGTGT
1601 GGTGGATGCA ATGATGTTTC TGAAACTGCT ATGTACAACC TACCCTGTGT
1651 ATAACATTTC GTACAATATT ATTGTTTTAC TTTTCAGCAA ATATGAAACA
1701 AATGTGTTTT ATTTTCATGG GAGTAAAATA TACTGCATAC AAAAAAAAAA
1751 AAAAAAAAAA AAAAA (B)
1   CACCGAGCGG CTCCCTAAAG AGGCTCGCAG CGGTTCCCTC CTGCCCACGT CCCCACGTCT
61  GCGTTGGCCC CCCTGCCTTT CGGCTGCCGA ACTCTTTTTG GCTGGAGTCT GAAGCTAGAG
121 GAGACAGGGC TGGAGGATTC GGCAGTTTGC GTTCCCTGGC TCTTTCAAGT CTCGGCTAAC
181 ACGGGGACAC TTGGCGCCTA GAGCGCTACC GAGAACCGGC GGCCACCGGG GCTCCACTGG
241 CGGTAGCCCT GGACTCATAG GGCTCCGCAC TCCCTCGTCCATG AAC TGC ATG AAA GGC
                                              Met Asn Cys Met Lys Gly

CCG CTG CCC TTG GAG CAC CGA GCA GCC GGG ACT AAG CTG TCG GCC GCC TCC
Pro Leu Pro Leu Glu His Arg Ala Ala Gly Thr Lys Leu Ser Ala Ala Ser

TCA CCC TTC TGT CAC CAT CCC CAG GCG TTA GCC ATG GCT TCG GTC CTA GCT
Ser Pro Phe Cys His His Pro Gln Ala Leu Ala Met Ala Ser Val Leu Ala

CCT GGC CAG CCC CGC TCC TTG GAC TCC TCC AAA CAT AGA CTG GAG GTG CAT
Pro Gly Gln Pro Arg Ser Leu Asp Ser Ser Lys His Arg Leu Glu Val His
                                                                  #

ACA ATC TCC GAT ACT TCC AGC CCT GAA GTC GCA
Thr Ile Ser Asp Thr Ser Ser Pro Glu Val Ala (C)
ACCGCGCCCA GGGCGCGGGG ATCCGAGGAC TGTCGGAGTG GGCAACTCTG CCCCAGAAAG
ACTGAGAATT GTGCTAGAAG TTCGTGCGCA CTATGGGAAG GAAGAGGGGG GAAAAAGAT
CAGAGGAAAA GAAACCACTG AATTCAAAGA GAGAGCGCCT TTGATTTCAA AGGAATGTCC
CCAAGTGTCT ACGTCTTTCG CTAAGAGTAT TCCCAACAGT GGAGGACGC GTACGCCCAC
AAATGTTTGA CTGGATATGA CATTTTAACA TTACTATAAG CTTGTTATTT TTAAGTTTA
GCATTGTTAA CATTAAAATG ACTGAAAGGA TGTATATATA TCGAAATGTC AAATTAATTT
*TATAAAAGCA* *GTTGTTAGTA* *CTATCACTAC* *AGTGTTTTA* *AAGGCTAGGC* *TTTA**AAATAA*
*A**GCATGTTAT* *ACAGAATCAG* *TTAGGATTTT* *TCGCTTGCGA* *GCAAAGGAAT* *GTATATACTA*
*AATGCCACAC* *TGTATGTTTC* *TAACATATTA* *TTATT*

FIG. 1B (A)

| gene name | \<--- homeodomain sequence ---\> | | | | | | identity | SEQ ID NO. |
|---|---|---|---|---|---|---|---|---|
| | helix 1 | | helix 2 | | helix 3/4 | | | |
| | QRRQRTHFTS | QQLQELEATF | QRNRTPDMST | REEIAVWTNL | TEARVRVWFK | NRRAKWRKRE | | |
| Solurshin | ---------- | ---------- | ---------- | ---------- | ---------- | ---------- | 97% | SEQ ID NO. 7 |
| ptx-1 | P--------- | ---------- | ---------M | ---------- | --P------- | ---------- | 83% | SEQ ID NO. 8 |
| unc-30 | ---------- | H--T---NW- | S------AC | --------IS- | ---------- | ---------- | 62% | SEQ ID NO. 9 |
| otx-1 | ---E--T--R | S---DV----L | AKT----IF- | ---V-LKI-- | P-S--Q---- | ----C-QQQ | 62% | SEQ ID NO.10 |
| otx-2 | ---E--T--R | A--DV----L | AKT----IF- | ---V-LKI-- | P-S--Q---- | ----C-QQQ | 62% | SEQ ID NO.11 |
| dm-otd | ---E--T--R | A--DV----L | GKT----IF- | ---V-LKI-- | P-S--Q---- | ----C-QQL | 62% | SEQ ID NO.12 |
| goosecoid | K--H--I---D | E--EA---NL- | -ETK----VGT | --QL-RKVH- | R-EK-E---- | ----RQK | 53% | SEQ ID NO.13 |
| pax-7 | ---S--T--A | E--E---KA- | E-TH----IY- | ---L-QR-K- | ----Q---S | ----R---QA | 65% | SEQ ID NO.14 |
| pax-3 | ---S--T--A | E--E---KA- | E-TH----IYT | ---L-QRAK- | --A--Q---S | ----R---QA | 60% | SEQ ID NO.15 |
| paired | ---C--T-SA | S--D---RA- | E-TQ----IYT | ---L-QR--- | --A--Q---S | ----RL--QH | 58% | SEQ ID NO.16 |
| rat drg11 | ---N--T-AL | ---EA----V- | AQTH---VF- | ---L-MKI-- | --A--Q---Q | -----T--- | 67% | SEQ ID NO.17 |
| prd-like | ---Y--T-AL | F--E---KA- | S-TH----VF- | ---L-MKIG- | ---IQ---Q | -----Q--- | 67% | SEQ ID NO.18 |
| dm-al | ---Y--T-AL | F--E---KA- | S-TH----VF- | ---L-MKIG- | ---IQ---Q | -----Q--- | 67% | SEQ ID NO.19 |
| cart-1 | K--H--T--- | L--E---KV- | -KTH----VYV | --QL-LR-E- | --A--Q---Q | -------- | 65% | SEQ ID NO.20 |
| prx-1 | ---N--T-N- | S---A--RV- | E-TH----AFV | --DL-RRV-- | -----Q---Q | ----F-RN- | 62% | SEQ ID NO.21 |
| prx-2 | ---N--T-N- | S---A--RV- | E-TH----AFV | ---L-RRV-- | S----Q---Q | ----F-RN- | 62% | SEQ ID NO.22 |
| phox-2 | ---I--T--- | A--K---RV- | AETH---IYT | ---L-LKID- | --A--Q---Q | ----F-Q-- | 62% | SEQ ID NO.23 |
| murine hmk2 | ---N--T-N- | S---A--RV- | E-TH----AFV | --DL-RRV-- | -----Q---Q | ----F-RN- | 62% | SEQ ID NO.24 |
| murine chx10 | K--H--I--- | Y--E---KA | -NEAH---VYA | --ML-MK-E- | P-D-IQ---Q | -------- | 60% | SEQ ID NO.25 |
| murine otp | -K-H--R-P | A--N---RS | -AKTH---IFM | ---L-LRIG- | ---S--Q---Q | ----K--K | 58% | SEQ ID NO.26 |

FIG. 2A (B)

| gene name | sequence | | SEQ ID NO. |
|---|---|---|---|
| Solurshin | SSLASLRLKAKQHS | (14) | SEQ ID NO.27 |
| murine ptx-1 | -------------- | (0) | SEQ ID NO.28 |
| chick prx-2 | N-I-----EF-- | (4) | SEQ ID NO.29 |
| chick prx-1 | N-I-N-----EY- | (5) | SEQ ID NO.30 |
| human Cart-1 | --I-V--M---E-T | (5) | SEQ ID NO.31 |
| dm-aristaless | --I-A-----RE-E | (5) | SEQ ID NO.32 |
| murine hmk2 | N-I-N-----EY- | (5) | SEQ ID NO.33 |
| rat drg11 | A-V-A--M--RE-- | (6) | SEQ ID NO.34 |
| murine chx10 | N-I-A--A--QE-- | (6) | SEQ ID NO.35 |
| murine otp | T-I-----R--LE-T | (6) | SEQ ID NO.36 |

FIG. 2B

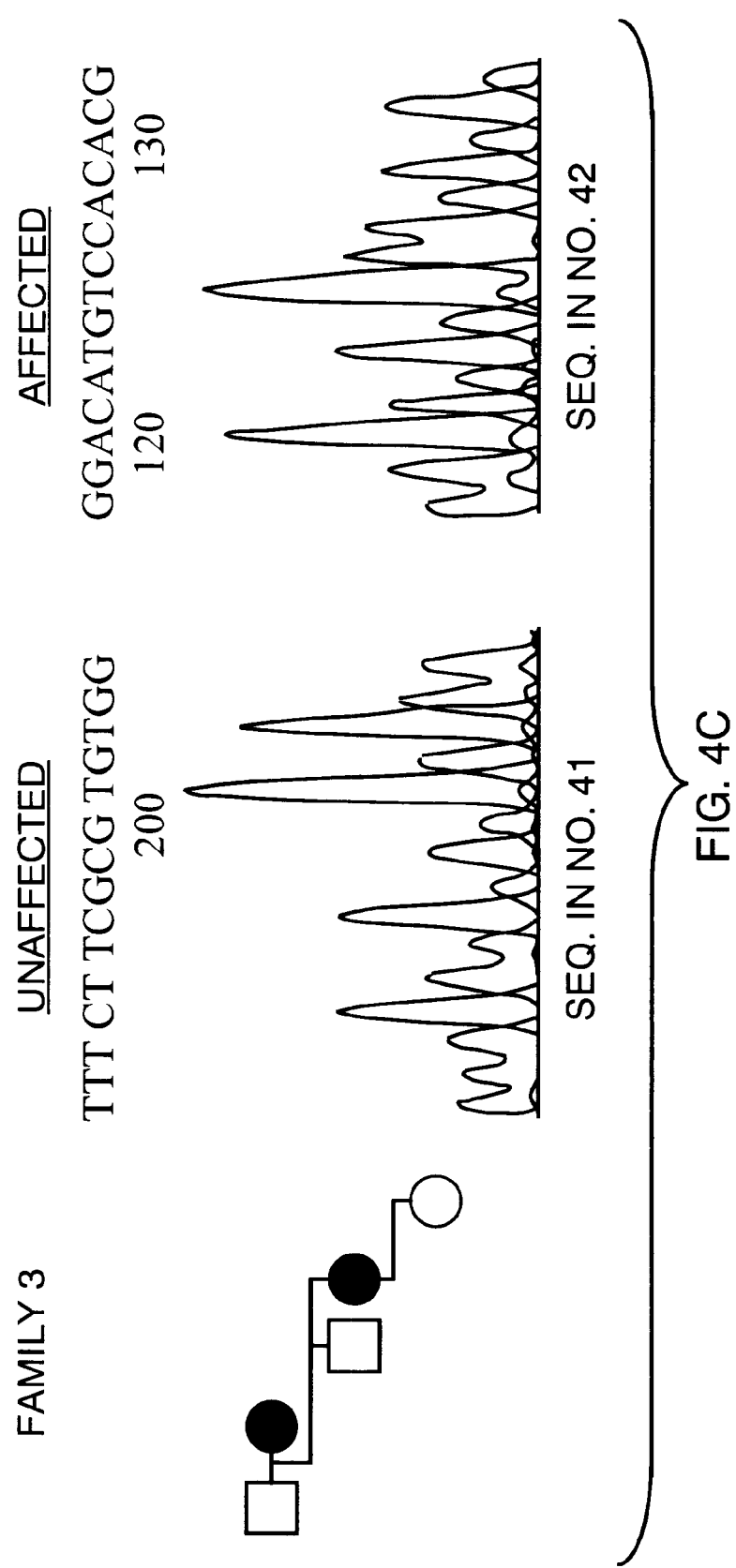

SEQUENCE LISTING (1) GENERAL INFORMATION:

(iii) NUMBER OF SEQUENCES: 139

(2) INFORMATION FOR SEQ ID NO:1:

(i) SEQUENCE CHARACTERISTICS:
       (A) LENGTH: 1775 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 234..1047

(xi) SEQUENCE DESCRIPTION: SEQ ID NO:1:

```
CGAGAAAGCT GGAGAGGAGC AGAAAGAAAC TGCCAGTGGC GGCTAGATTT CGGAGGCCCC      60

AGTGCACCCG TGGACTCCTT CGGAACTTGG CACCCTCAGG AGCCCTGCAG TCCTCTCAGG     120

CCCGGCTTTC GGGCGCTTGC CGTGCAGCCG GAGGCTCGGC TCGCTGGAAA TCGCCCCGGG     180

AAGCAGTGGG ACGCGGAGAC AGCAGCTCTC TCCCGGTAGC CGATAACGGG GAA ATG        236
                                                          Met
                                                            1

GAG ACC AAC TGC CGC AAA CTG GTG TCG GCG TGT CTG CAA TTA GAG AAA       284
Glu Thr Asn Cys Arg Lys Leu Val Ser Ala Cys Leu Gln Leu Glu Lys
              5                  10                  15

GAT AAA AGC CAG CAG GGG AAG AAT GAG GAC GTG GGC GCC GAG GAC CCG       332
Asp Lys Ser Gln Gln Gly Lys Asn Glu Asp Val Gly Ala Glu Asp Pro
         20                  25                  30

TCT AAG AAG AAG CGG CAA AGG CGG CAG CGG ACT CAC TTT ACC AGC CAG       380
Ser Lys Lys Lys Arg Gln Arg Arg Gln Arg Thr His Phe Thr Ser Gln
     35                  40                  45

CAG CTC CAG CAG CTG GAG GCC ACT TTC CAG AGG AAC CGC TAC CCG GAC       428
Gln Leu Gln Gln Leu Glu Ala Thr Phe Gln Arg Asn Arg Tyr Pro Asp
 50                  55                  60                  65

ATG TCC ACA CGC GAA GAA ATC GCT GTG TGG ACC AAC CTT ACG GAA GCC       476
Met Ser Thr Arg Glu Glu Ile Ala Val Trp Thr Asn Leu Thr Glu Ala
                 70                  75                  80

CGA GTC CGG GTT TGG TTC AAG AAT CGT CGG GCC AAA TGG AGA AAG AGG       524
Arg Val Arg Val Trp Phe Lys Asn Arg Arg Ala Lys Trp Arg Lys Arg
             85                  90                  95

GAG CGC AAC CAG CAG GCC GAG CTA TGC AAG AAT GGC TTC GGG CCG CAG       572
Glu Arg Asn Gln Gln Ala Glu Leu Cys Lys Asn Gly Phe Gly Pro Gln
        100                 105                 110

TTC AAT GGG CTC ATG CAG CCC TAC GAC GAC ATG TAC CCA GGC TAT TCC       620
Phe Asn Gly Leu Met Gln Pro Tyr Asp Asp Met Tyr Pro Gly Tyr Ser
    115                 120                 125

TAC AAC AAC TGG GCC GCC AAG GGC CTT ACA TCC GCC TCC CTA TCC ACC       668
Tyr Asn Asn Trp Ala Ala Lys Gly Leu Thr Ser Ala Ser Leu Ser Thr
130                 135                 140                 145

AAG AGC TTC CCC TTC TTC AAC TCT ATG AAC GTC AAC CCC CTG TCA TCA       716
Lys Ser Phe Pro Phe Phe Asn Ser Met Asn Val Asn Pro Leu Ser Ser
                150                 155                 160

CAG AGC ATG TTT TCC CCA CCC AAC TCT ATC TCG TCC ATG AGC ATG TCG       764
Gln Ser Met Phe Ser Pro Pro Asn Ser Ile Ser Ser Met Ser Met Ser
            165                 170                 175

TCC AGC ATG GTG CCC TCA GCA GTG ACA GGC GTC CCG GGC TCC AGT CTC       812
```

```
            Ser Ser Met Val Pro Ser Ala Val Thr Gly Val Pro Gly Ser Ser Leu
                    180                 185                 190

AAC AGC CTG AAT AAC TTG AAC AAC CTG AGT AGC CCG TCG CTG AAT TCC              860
Asn Ser Leu Asn Asn Leu Asn Asn Leu Ser Ser Pro Ser Leu Asn Ser
    195                 200                 205

GCG GTG CCG ACG CCT GCC TGT CCT TAC GCG CCG CCG ACT CCT CCG TAT              908
Ala Val Pro Thr Pro Ala Cys Pro Tyr Ala Pro Pro Thr Pro Pro Tyr
210                 215                 220                 225

GTT TAT AGG GAC ACG TGT AAC TCG AGC CTG GCC AGC CTG AGA CTG AAA              956
Val Tyr Arg Asp Thr Cys Asn Ser Ser Leu Ala Ser Leu Arg Leu Lys
                230                 235                 240

GCA AAG CAG CAC TCC AGC TTC GGC TAC GCC AGC GTG CAG AAA CCG GCC              1004
Ala Lys Gln His Ser Ser Phe Gly Tyr Ala Ser Val Gln Lys Pro Ala
            245                 250                 255

TCC AAC CTG AGT GCT TGC CAG TAT GCA GTG GAC CGG CCC GTG T                    1047
Ser Asn Leu Ser Ala Cys Gln Tyr Ala Val Asp Arg Pro Val
        260                 265                 270

GAGCCGCACC CACAGCGCCG GGATCCTAGG ACCTTGCCGG ATGGGCAAC TCCGCCCTTG              1107

AAAGACTGGG AATTATGCTA GAAGGTCGTG GGCACTAAAG AAAGGGAGAG AAAGAGAAGC             1167

TATATAGAGA AAAGGAAACC ACTGAATCAA AGAGAGAGCT CCTTTGATTT CAAAGGGATG             1227

TCCTCAGTGT CTGACATCTT TCACTACAAG TATTTCTAAC AGTTGCAAGG ACACATACAC             1287

AAACAAATGT TTTGACTGGA TATGACATTT TAACATTACT ATAAGCTTGT TATTTTTTAA             1347

GTTTAGCATT GTTAACATTT AAATGACTGA AAGGATGTAT ATATATCGAA ATGTCAAATT             1407

AATTTTATAA AAGCAGTTGT TAGTAATATC ACAACAGTGT TTTTAAAGGT TAGGCTTTAA             1467

AATAAAGCAT GTTATACAGA AGCGATTAGG ATTTTTCGCT TGCGAGCAAG GGAGTGTATA             1527

TACTAAATGC CACACTGTAT GTTTCTAACA TATTATTATT ATTATAAAAA ATGTGTGAAT             1587

ATCAGTTTTA GAATAGTTTG TGTGGTGGAT GCAATGATGT TTCTGAAACT GCTATGTACA             1647

ACCTACCCTG TGTATAACAT TTCGTACAAT ATTATTGTTT TACTTTTCAG CAAATATGAA             1707

ACAAATGTGT TTTATTTTCA TGGGAGTAAA ATATACTGCA TACAAAAAAA AAAAAAAAAA             1767

AAAAAAAA                                                                     1775

(2) INFORMATION FOR SEQ ID NO:2:

(i) SEQUENCE CHARACTERISTICS:
        (A) LENGTH: 271 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Thr Asn Cys Arg Lys Leu Val Ser Ala Cys Leu Gln Leu Glu
1               5                   10                  15

Lys Asp Lys Ser Gln Gln Gly Lys Asn Glu Asp Val Gly Ala Glu Asp
            20                  25                  30

Pro Ser Lys Lys Lys Arg Gln Arg Arg Gln Arg Thr His Phe Thr Ser
        35                  40                  45

Gln Gln Leu Gln Gln Leu Glu Ala Thr Phe Gln Arg Asn Arg Tyr Pro
    50                  55                  60

Asp Met Ser Thr Arg Glu Glu Ile Ala Val Trp Thr Asn Leu Thr Glu
65                  70                  75                  80

Ala Arg Val Arg Val Trp Phe Lys Asn Arg Arg Ala Lys Trp Arg Lys
                85                  90                  95
```

-continued

```
Arg Glu Arg Asn Gln Gln Ala Glu Leu Cys Lys Asn Gly Phe Gly Pro
            100                 105                 110

Gln Phe Asn Gly Leu Met Gln Pro Tyr Asp Asp Met Tyr Pro Gly Tyr
            115                 120                 125

Ser Tyr Asn Asn Trp Ala Ala Lys Gly Leu Thr Ser Ala Ser Leu Ser
        130                 135             140

Thr Lys Ser Phe Pro Phe Phe Asn Ser Met Asn Val Asn Pro Leu Ser
145                 150                 155                 160

Ser Gln Ser Met Phe Ser Pro Pro Asn Ser Ile Ser Ser Met Ser Met
                165                 170                 175

Ser Ser Ser Met Val Pro Ser Ala Val Thr Gly Val Pro Gly Ser Ser
            180                 185                 190

Leu Asn Ser Leu Asn Asn Leu Asn Asn Leu Ser Ser Pro Ser Leu Asn
        195                 200                 205

Ser Ala Val Pro Thr Pro Ala Cys Pro Tyr Ala Pro Pro Thr Pro Pro
    210                 215                 220

Tyr Val Tyr Arg Asp Thr Cys Asn Ser Ser Leu Ala Ser Leu Arg Leu
225                 230                 235                 240

Lys Ala Lys Gln His Ser Ser Phe Gly Tyr Ala Ser Val Gln Lys Pro
                245                 250                 255

Ala Ser Asn Leu Ser Ala Cys Gln Tyr Ala Val Asp Arg Pro Val
            260                 265                 270

(2) INFORMATION FOR SEQ ID NO:3:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..814

(xi) SEQUENCE DESCRIPTION: SEQ ID NO:3:

ATG GAG ACC AAC TGC CGC AAA CTG GTG TCG GCG TGT CTG CAA TTA GAG      48
Met Glu Thr Asn Cys Arg Lys Leu Val Ser Ala Cys Leu Gln Leu Glu
 1               5                  10                  15

AAA GAT AAA AGC CAG CAG GGG AAG AAT GAG GAC GTG GGC GCC GAG GAC      96
Lys Asp Lys Ser Gln Gln Gly Lys Asn Glu Asp Val Gly Ala Glu Asp
                20                  25                  30

CCG TCT AAG AAG AAG CGG CAA AGG CGG CAG CGG ACT CAC TTT ACC AGC     144
Pro Ser Lys Lys Lys Arg Gln Arg Arg Gln Arg Thr His Phe Thr Ser
            35                  40                  45

CAG CAG CTC CAG CAG CTG GAG GCC ACT TTC CAG AGG AAC CGC TAC CCG     192
Gln Gln Leu Gln Gln Leu Glu Ala Thr Phe Gln Arg Asn Arg Tyr Pro
        50                  55                  60

GAC ATG TCC ACA CGC GAA GAA ATC GCT GTG TGG ACC AAC CTT ACG GAA     240
Asp Met Ser Thr Arg Glu Glu Ile Ala Val Trp Thr Asn Leu Thr Glu
 65                  70                  75                  80

GCC CGA GTC CGG GTT TGG TTC AAG AAT CGT CGG GCC AAA TGG AGA AAG     288
Ala Arg Val Arg Val Trp Phe Lys Asn Arg Arg Ala Lys Trp Arg Lys
                85                  90                  95

AGG GAG CGC AAC CAG CAG GCC GAG CTA TGC AAG AAT GGC TTC GGG CCG     336
Arg Glu Arg Asn Gln Gln Ala Glu Leu Cys Lys Asn Gly Phe Gly Pro
                100                 105                 110

CAG TTC AAT GGG CTC ATG CAG CCC TAC GAC GAC ATG TAC CCA GGC TAT     384
```

```
Gln Phe Asn Gly Leu Met Gln Pro Tyr Asp Asp Met Tyr Pro Gly Tyr
        115                 120                 125

TCC TAC AAC AAC TGG GCC GCC AAG GGC CTT ACA TCC GCC TCC CTA TCC        432
Ser Tyr Asn Asn Trp Ala Ala Lys Gly Leu Thr Ser Ala Ser Leu Ser
    130                 135                 140

ACC AAG AGC TTC CCC TTC TTC AAC TCT ATG AAC GTC AAC CCC CTG TCA        480
Thr Lys Ser Phe Pro Phe Phe Asn Ser Met Asn Val Asn Pro Leu Ser
145                 150                 155                 160

TCA CAG AGC ATG TTT TCC CCA CCC AAC TCT ATC TCG TCC ATG AGC ATG        528
Ser Gln Ser Met Phe Ser Pro Pro Asn Ser Ile Ser Ser Met Ser Met
                165                 170                 175

TCG TCC AGC ATG GTG CCC TCA GCA GTG ACA GGC GTC CCG GGC TCC AGT        576
Ser Ser Ser Met Val Pro Ser Ala Val Thr Gly Val Pro Gly Ser Ser
                180                 185                 190

CTC AAC AGC CTG AAT AAC TTG AAC AAC CTG AGT AGC CCG TCG CTG AAT        624
Leu Asn Ser Leu Asn Asn Leu Asn Asn Leu Ser Ser Pro Ser Leu Asn
                195                 200                 205

TCC GCG GTG CCG ACG CCT GCC TGT CCT TAC GCG CCG CCG ACT CCT CCG        672
Ser Ala Val Pro Thr Pro Ala Cys Pro Tyr Ala Pro Pro Thr Pro Pro
210                 215                 220

TAT GTT TAT AGG GAC ACG TGT AAC TCG AGC CTG GCC AGC CTG AGA CTG        720
Tyr Val Tyr Arg Asp Thr Cys Asn Ser Ser Leu Ala Ser Leu Arg Leu
225                 230                 235                 240

AAA GCA AAG CAG CAC TCC AGC TTC GGC TAC GCC AGC GTG CAG AAA CCG        768
Lys Ala Lys Gln His Ser Ser Phe Gly Tyr Ala Ser Val Gln Lys Pro
                245                 250                 255

GCC TCC AAC CTG AGT GCT TGC CAG TAT GCA GTG GAC CGG CCC GTG T           814
Ala Ser Asn Leu Ser Ala Cys Gln Tyr Ala Val Asp Arg Pro Val
                260                 265                 270

GA                                                                      816

(2) INFORMATION FOR SEQ ID NO:4:

(i) SEQUENCE CHARACTERISTICS:
        (A) LENGTH: 1775 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 234..1047

(xi) SEQUENCE DESCRIPTION: SEQ ID NO:4:

CGAGAAAGCT GGAGAGGAGC AGAAAGAAAC TGCCAGTGGC GGCTAGATTT CGGAGGCCCC       60

AGTGCACCCG TGGACTCCTT CGGAACTTGG CACCCTCAGG AGCCCTGCAG TCCTCTCAGG      120

CCCGGCTTTC GGGCGCTTGC CGTGCAGCCG GAGGCTCGGC TCGCTGGAAA TCGCCCCGGG     180

AAGCAGTGGG ACGCGGAGAC AGCAGCTCTC TCCCGGTAGC CGATAACGGG GAA ATG         236
                                                              Met
                                                               1

GAG ACC AAC TGC CGC AAA CTG GTG TCG GCG TGT CTG CAA TTA GAG AAA        284
Glu Thr Asn Cys Arg Lys Leu Val Ser Ala Cys Leu Gln Leu Glu Lys
         5                  10                  15

GAT AAG GGC CAG CAA GGA AAG AAT GAG GAT GTG GGC GCC GAG GAC CCG        332
Asp Lys Gly Gln Gln Gly Lys Asn Glu Asp Val Gly Ala Glu Asp Pro
            20                  25                  30

TCC AAG AAG AAG CGG CAA CGC CGG CAG AGG ACT CAT TTC ACT AGC CAG        380
Ser Lys Lys Lys Arg Gln Arg Arg Gln Arg Thr His Phe Thr Ser Gln
        35                  40                  45
```

```
CAG CTG CAG CAG CTG GAA GCC ACT TTC CAG AGA AAC CGC TAC CCA GAC    428
Gln Leu Gln Gln Leu Glu Ala Thr Phe Gln Arg Asn Arg Tyr Pro Asp
 50                  55                  60                  65

ATG TCC ACT CGC GAA GAA ATC GCT GTG TGG ACC AAC CTT ACG GAA GCC    476
Met Ser Thr Arg Glu Glu Ile Ala Val Trp Thr Asn Leu Thr Glu Ala
                 70                  75                  80

CGA GTC CGG GTT TGG TTC AAG AAT CGC CGG GCC AAA TGG AGA AAG CGG    524
Arg Val Arg Val Trp Phe Lys Asn Arg Arg Ala Lys Trp Arg Lys Arg
                     85                  90                  95

GAA CGC AAC CAG CAG GCC GAG CTG TGC AAG AAT GGC TTT GGG CCG CAG    572
Glu Arg Asn Gln Gln Ala Glu Leu Cys Lys Asn Gly Phe Gly Pro Gln
                100                 105                 110

TTC AAC GGG CTC ATG CAG CCC TAC GAC GAC ATG TAC CCC GGC TAT TCG    620
Phe Asn Gly Leu Met Gln Pro Tyr Asp Asp Met Tyr Pro Gly Tyr Ser
115                 120                 125

TAC AAC AAC TGG GCT GCC AAG GGC CTC ACG TCA GCG TCT CTG TCC ACC    668
Tyr Asn Asn Trp Ala Ala Lys Gly Leu Thr Ser Ala Ser Leu Ser Thr
130                 135                 140                 145

AAG AGC TTC CCC TTC TTC AAC TCC ATG AAC GTC AAT CCC CTG TCG TCT    716
Lys Ser Phe Pro Phe Phe Asn Ser Met Asn Val Asn Pro Leu Ser Ser
                150                 155                 160

CAG AGT ATG TTT TCC CCG CCC AAC TCC ATC TCA TCT ATG AGT ATG TCG    764
Gln Ser Met Phe Ser Pro Pro Asn Ser Ile Ser Ser Met Ser Met Ser
            165                 170                 175

TCC AGC ATG GTG CCC TCC GCG GTG ACC GGC GTC CCG GGC TCC AGC CTC    812
Ser Ser Met Val Pro Ser Ala Val Thr Gly Val Pro Gly Ser Ser Leu
        180                 185                 190

AAT AGC CTG AAT AAC TTG AAC AAC CTG AGC AGC CCG TCG CTG AAT TCC    860
Asn Ser Leu Asn Asn Leu Asn Asn Leu Ser Ser Pro Ser Leu Asn Ser
    195                 200                 205

GCG GTG CCC ACG CCC GCC TGT CCT TAC GCG CCG CCG ACT CCT CCG TAC    908
Ala Val Pro Thr Pro Ala Cys Pro Tyr Ala Pro Pro Thr Pro Pro Tyr
210                 215                 220                 225

GTT TAT AGG GAC ACA TGT AAC TCG AGC CTG GCC AGC CTG AGA CTG AAA    956
Val Tyr Arg Asp Thr Cys Asn Ser Ser Leu Ala Ser Leu Arg Leu Lys
                230                 235                 240

GCA AAG CAG CAC TCC AGC TTC GGC TAC GCC AGC GTG CAG AAC CCG GCC   1004
Ala Lys Gln His Ser Ser Phe Gly Tyr Ala Ser Val Gln Asn Pro Ala
                245                 250                 255

TCC AAC CTG AGT GCT TGC CAG TAT GCA GTG GAC CCG CCC GTG T         1047
Ser Asn Leu Ser Ala Cys Gln Tyr Ala Val Asp Pro Pro Val
                260                 265                 270

GAGCCGCACC CACAGCGCCG GGATCCTAGG ACCTTGCCGG ATGGGCAAC TCCGCCCTTG   1107

AAAGACTGGG AATTATGCTA GAAGGTCGTG GGCACTAAAG AAAGGGAGAG AAAGAGAAGC  1167

TATATAGAGA AAAGGAAACC ACTGAATCAA AGAGAGAGCT CCTTTGATTT CAAAGGGATG  1227

TCCTCAGTGT CTGACATCTT TCACTACAAG TATTTCTAAC AGTTGCAAGG ACACATACAC  1287

AAACAAATGT TTTGACTGGA TATGACATTT TAACATTACT ATAAGCTTGT TATTTTTTAA  1347

GTTTAGCATT GTTAACATTT AAATGACTGA AGGATGTAT ATATATCGAA ATGTCAAATT   1407

AATTTTATAA AAGCAGTTGT TAGTAATATC ACAACAGTGT TTTTAAAGGT TAGGCTTTAA  1467

AATAAAGCAT GTTATACAGA AGCGATTAGG ATTTTTCGCT TGCGAGCAAG GGAGTGTATA  1527

TACTAAATGC CACACTGTAT GTTTCTAACA TATTATTATT ATTATAAAAA ATGTGTGAAT  1587

ATCAGTTTTA GAATAGTTTG TGTGGTGGAT GCAATGATGT TTCTGAAACT GCTATGTACA  1647

ACCTACCCTG TGTATAACAT TTCGTACAAT ATTATTGTTT TACTTTTCAG CAAATATGAA  1707
```

```
ACAAATGTGT TTTATTTTCA TGGGAGTAAA ATATACTGCA TACAAAAAAA AAAAAAAAAA      1767

AAAAAAAA                                                               1775
```

(2) INFORMATION FOR SEQ ID NO:5:

(i) SEQUENCE CHARACTERISTICS:
        (A) LENGTH: 271 amino acids
        (B) TYPE: amino acid
        (D) TOPOLOGY: linear (ii) MOLECULE TYPE: protein (xi) SEQUENCE DESCRIPTION: SEQ ID NO:5:

```
Met Glu Thr Asn Cys Arg Lys Leu Val Ser Ala Cys Leu Gln Leu Glu
 1               5                  10                  15

Lys Asp Lys Gly Gln Gln Gly Lys Asn Glu Asp Val Gly Ala Glu Asp
            20                  25                  30

Pro Ser Lys Lys Lys Arg Gln Arg Arg Gln Arg Thr His Phe Thr Ser
        35                  40                  45

Gln Gln Leu Gln Gln Leu Glu Ala Thr Phe Gln Arg Asn Arg Tyr Pro
    50                  55                  60

Asp Met Ser Thr Arg Glu Glu Ile Ala Val Trp Thr Asn Leu Thr Glu
65                  70                  75                  80

Ala Arg Val Arg Val Trp Phe Lys Asn Arg Arg Ala Lys Trp Arg Lys
                85                  90                  95

Arg Glu Arg Asn Gln Gln Ala Glu Leu Cys Lys Asn Gly Phe Gly Pro
            100                 105                 110

Gln Phe Asn Gly Leu Met Gln Pro Tyr Asp Asp Met Tyr Pro Gly Tyr
        115                 120                 125

Ser Tyr Asn Asn Trp Ala Ala Lys Gly Leu Thr Ser Ala Ser Leu Ser
    130                 135                 140

Thr Lys Ser Phe Pro Phe Phe Asn Ser Met Asn Val Asn Pro Leu Ser
145                 150                 155                 160

Ser Gln Ser Met Phe Ser Pro Pro Asn Ser Ile Ser Ser Met Ser Met
                165                 170                 175

Ser Ser Ser Met Val Pro Ser Ala Val Thr Gly Val Pro Gly Ser Ser
            180                 185                 190

Leu Asn Ser Leu Asn Asn Leu Asn Asn Leu Ser Ser Pro Ser Leu Asn
        195                 200                 205

Ser Ala Val Pro Thr Pro Ala Cys Pro Tyr Ala Pro Pro Thr Pro Pro
    210                 215                 220

Tyr Val Tyr Arg Asp Thr Cys Asn Ser Ser Leu Ala Ser Leu Arg Leu
225                 230                 235                 240

Lys Ala Lys Gln His Ser Ser Phe Gly Tyr Ala Ser Val Gln Asn Pro
                245                 250                 255

Ala Ser Asn Leu Ser Ala Cys Gln Tyr Ala Val Asp Pro Pro Val
            260                 265                 270
```

(2) INFORMATION FOR SEQ ID NO:6:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ii) MOLECULE TYPE: cDNA (ix) FEATURE:

(A) NAME/KEY: CDS
        (B) LOCATION: 1..814

(xi) SEQUENCE DESCRIPTION: SEQ ID NO:6:

```
ATG GAG ACC AAC TGC CGC AAA CTG GTG TCG GCG TGT CTG CAA TTA GAG      48
Met Glu Thr Asn Cys Arg Lys Leu Val Ser Ala Cys Leu Gln Leu Glu
 1               5                  10                  15

AAA GAT AAG GGC CAG CAA GGA AAG AAT GAG GAT GTG GGC GCC GAG GAC      96
Lys Asp Lys Gly Gln Gln Gly Lys Asn Glu Asp Val Gly Ala Glu Asp
             20                  25                  30

CCG TCC AAG AAG AAG CGG CAA CGC CGG CAG AGG ACT CAT TTC ACT AGC     144
Pro Ser Lys Lys Lys Arg Gln Arg Arg Gln Arg Thr His Phe Thr Ser
         35                  40                  45

CAG CAG CTG CAG CAG CTG GAA GCC ACT TTC CAG AGA AAC CGC TAC CCA     192
Gln Gln Leu Gln Gln Leu Glu Ala Thr Phe Gln Arg Asn Arg Tyr Pro
     50                  55                  60

GAC ATG TCC ACT CGC GAA GAA ATC GCT GTG TGG ACC AAC CTT ACG GAA     240
Asp Met Ser Thr Arg Glu Glu Ile Ala Val Trp Thr Asn Leu Thr Glu
 65                  70                  75                  80

GCC CGA GTC CGG GTT TGG TTC AAG AAT CGC CGG GCC AAA TGG AGA AAG     288
Ala Arg Val Arg Val Trp Phe Lys Asn Arg Arg Ala Lys Trp Arg Lys
                 85                  90                  95

CGG GAA CGC AAC CAG CAG GCC GAG CTG TGC AAG AAT GGC TTT GGG CCG     336
Arg Glu Arg Asn Gln Gln Ala Glu Leu Cys Lys Asn Gly Phe Gly Pro
            100                 105                 110

CAG TTC AAC GGG CTC ATG CAG CCC TAC GAC GAC ATG TAC CCC GGC TAT     384
Gln Phe Asn Gly Leu Met Gln Pro Tyr Asp Asp Met Tyr Pro Gly Tyr
        115                 120                 125

TCG TAC AAC AAC TGG GCT GCC AAG GGC CTC ACG TCA GCG TCT CTG TCC     432
Ser Tyr Asn Asn Trp Ala Ala Lys Gly Leu Thr Ser Ala Ser Leu Ser
    130                 135                 140

ACC AAG AGC TTC CCC TTC TTC AAC TCC ATG AAC GTC AAT CCC CTG TCG     480
Thr Lys Ser Phe Pro Phe Phe Asn Ser Met Asn Val Asn Pro Leu Ser
145                 150                 155                 160

TCT CAG AGT ATG TTT TCC CCG CCC AAC TCC ATC TCA TCT ATG AGT ATG     528
Ser Gln Ser Met Phe Ser Pro Pro Asn Ser Ile Ser Ser Met Ser Met
                165                 170                 175

TCG TCC AGC ATG GTG CCC TCC GCG GTG ACC GGC GTC CCG GGC TCC AGC     576
Ser Ser Ser Met Val Pro Ser Ala Val Thr Gly Val Pro Gly Ser Ser
            180                 185                 190

CTC AAT AGC CTG AAT AAC TTG AAC AAC CTG AGC AGC CCG TCG CTG AAT     624
Leu Asn Ser Leu Asn Asn Leu Asn Asn Leu Ser Ser Pro Ser Leu Asn
        195                 200                 205

TCC GCG GTG CCC ACG CCC GCC TGT CCT TAC GCG CCG CCG ACT CCT CCG     672
Ser Ala Val Pro Thr Pro Ala Cys Pro Tyr Ala Pro Pro Thr Pro Pro
    210                 215                 220

TAC GTT TAT AGG GAC ACA TGT AAC TCG AGC CTG GCC AGC CTG AGA CTG     720
Tyr Val Tyr Arg Asp Thr Cys Asn Ser Ser Leu Ala Ser Leu Arg Leu
225                 230                 235                 240

AAA GCA AAG CAG CAC TCC AGC TTC GGC TAC GCC AGC GTG CAG AAC CCG     768
Lys Ala Lys Gln His Ser Ser Phe Gly Tyr Ala Ser Val Gln Asn Pro
                245                 250                 255

GCC TCC AAC CTG AGT GCT TGC CAG TAT GCA GTG GAC CCG CCC GTG T       814
Ala Ser Asn Leu Ser Ala Cys Gln Tyr Ala Val Asp Pro Pro Val
            260                 265                 270

GA                                                                  816
```

(2) INFORMATION FOR SEQ ID NO:7:

(i) SEQUENCE CHARACTERISTICS:

(A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:7:

Gln Arg Arg Gln Arg Thr His Phe Thr Ser Gln Gln Leu Gln Glu Leu
1               5                  10                  15

Glu Ala Thr Phe Gln Arg Asn Arg Tyr Pro Asp Met Ser Thr Arg Glu
            20                  25                  30

Glu Ile Ala Val Trp Thr Asn Leu Thr Glu Ala Arg Val Arg Val Trp
        35                  40                  45

Phe Lys Asn Arg Arg Ala Lys Trp Arg Lys Arg Glu
50                  55                  60

(2) INFORMATION FOR SEQ ID NO:8:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:8:

Gln Arg Arg Gln Arg Thr His Phe Thr Ser Gln Gln Leu Gln Glu Leu
1               5                  10                  15

Glu Ala Thr Phe Gln Arg Asn Arg Tyr Pro Asp Met Ser Met Arg Glu
            20                  25                  30

Glu Ile Ala Val Trp Thr Asn Leu Thr Glu Pro Arg Val Arg Val Trp
        35                  40                  45

Phe Lys Asn Arg Arg Ala Lys Trp Arg Lys Arg Glu
50                  55                  60

(2) INFORMATION FOR SEQ ID NO:9:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:9:

Pro Arg Arg Gln Arg Thr His Phe Thr Ser His Gln Leu Thr Glu Leu
1               5                  10                  15

Glu Asn Trp Phe Ser Arg Asn Arg Tyr Pro Asp Met Ala Cys Arg Glu
            20                  25                  30

Glu Ile Ala Val Trp Ile Ser Leu Thr Glu Ala Arg Val Arg Val Trp
        35                  40                  45

Phe Lys Asn Arg Arg Ala Lys Trp Arg Lys Arg Glu
50                  55                  60

(2) INFORMATION FOR SEQ ID NO:10:

(i) SEQUENCE CHARACTERISTICS:
        (A) LENGTH: 60 amino acids (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:10:

Gln Arg Arg Glu Arg Thr Thr Phe Thr Arg Ser Gln Leu Asp Val Leu
1               5                   10                  15

Glu Ala Leu Phe Ala Lys Thr Arg Tyr Pro Asp Ile Phe Thr Arg Glu
            20                  25                  30

Glu Val Ala Leu Lys Ile Asn Leu Pro Glu Ser Arg Val Gln Val Trp
        35                  40                  45

Phe Lys Asn Arg Arg Ala Lys Cys Arg Gln Gln Gln
50                  55                  60

(2) INFORMATION FOR SEQ ID NO:11:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:11:

Gln Arg Arg Glu Arg Thr Thr Phe Thr Arg Ala Gln Leu Asp Val Leu
1               5                   10                  15

Glu Ala Leu Phe Ala Lys Thr Arg Tyr Pro Asp Ile Phe Thr Arg Glu
            20                  25                  30

Glu Val Ala Leu Lys Ile Asn Leu Pro Glu Ser Arg Val Gln Val Trp
        35                  40                  45

Phe Lys Asn Arg Arg Ala Lys Cys Arg Gln Gln Gln
50                  55                  60

(2) INFORMATION FOR SEQ ID NO:12:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:12:

Gln Arg Arg Glu Arg Thr Thr Phe Thr Arg Ala Gln Leu Asp Val Leu
1               5                   10                  15

Glu Ala Leu Phe Gly Lys Thr Arg Tyr Pro Asp Ile Phe Thr Arg Glu
            20                  25                  30

Glu Val Ala Leu Lys Ile Asn Leu Pro Glu Ser Arg Val Gln Val Trp
        35                  40                  45

Phe Lys Asn Arg Arg Ala Lys Cys Arg Gln Gln Leu
50                  55                  60

(2) INFORMATION FOR SEQ ID NO:13:

(i) SEQUENCE CHARACTERISTICS:
        (A) LENGTH: 60 amino acids
        (B) TYPE: amino acid

```
         (D) TOPOLOGY: linear (ii) MOLECULE TYPE: peptide (v) FRAGMENT TYPE: internal (xi) SEQUENCE DESCRIPTION: SEQ ID NO:13:

Lys Arg Arg His Arg Thr Ile Phe Thr Asp Glu Gln Leu Glu Ala Leu
1               5                  10                  15

Glu Asn Leu Phe Gln Glu Thr Lys Tyr Pro Asp Val Gly Thr Arg Glu
            20                  25                  30

Gln Leu Ala Arg Lys Val His Leu Arg Glu Glu Lys Val Glu Val Trp
        35                  40                  45

Phe Lys Asn Arg Arg Ala Lys Trp Arg Arg Gln Lys
50                  55                  60

(2) INFORMATION FOR SEQ ID NO:14:

(i) SEQUENCE CHARACTERISTICS:
         (A) LENGTH: 60 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO:14:

Gln Arg Arg Ser Arg Thr Thr Phe Thr Ala Glu Gln Leu Glu Glu Leu
1               5                  10                  15

Glu Lys Ala Phe Glu Arg Thr His Tyr Pro Asp Ile Tyr Thr Arg Glu
            20                  25                  30

Glu Leu Ala Gln Arg Thr Lys Leu Thr Glu Ala Arg Val Gln Val Trp
        35                  40                  45

Phe Ser Asn Arg Arg Ala Arg Trp Arg Lys Gln Ala
50                  55                  60

(2) INFORMATION FOR SEQ ID NO:15:

(i) SEQUENCE CHARACTERISTICS:
         (A) LENGTH: 60 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO:15:

Gln Arg Arg Ser Arg Thr Thr Phe Thr Ala Glu Gln Leu Glu Glu Leu
1               5                  10                  15

Glu Arg Ala Phe Glu Arg Thr His Tyr Pro Asp Ile Tyr Thr Arg Glu
            20                  25                  30

Glu Leu Ala Gln Arg Ala Lys Leu Thr Glu Ala Arg Val Gln Val Trp
        35                  40                  45

Phe Ser Asn Arg Arg Ala Arg Trp Arg Lys Gln Ala
50                  55                  60

(2) INFORMATION FOR SEQ ID NO:16:

(i) SEQUENCE CHARACTERISTICS:
         (A) LENGTH: 60 amino acids
         (B) TYPE: amino acid
         (D) TOPOLOGY: linear
```

(ii) MOLECULE TYPE: peptide (v) FRAGMENT TYPE: internal (xi) SEQUENCE DESCRIPTION: SEQ ID NO:16:

Gln Arg Arg Cys Arg Thr Thr Phe Ser Ala Ser Gln Leu Asp Glu Leu
1               5                   10                  15

Glu Arg Ala Phe Glu Arg Thr Gln Tyr Pro Asp Ile Tyr Thr Arg Glu
            20                  25                  30

Glu Leu Ala Gln Arg Thr Asn Leu Thr Glu Ala Arg Ile Gln Val Trp
        35                  40                  45

Phe Ser Asn Arg Arg Ala Arg Leu Arg Lys Gln His
    50                  55                  60

(2) INFORMATION FOR SEQ ID NO:17:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:17:

Gln Arg Arg Asn Arg Thr Thr Phe Ala Leu Gln Gln Leu Glu Ala Leu
1               5                   10                  15

Glu Ala Val Phe Ala Gln Thr His Tyr Pro Asp Val Phe Thr Arg Glu
            20                  25                  30

Glu Leu Ala Met Lys Ile Asn Leu Thr Glu Ala Arg Val Gln Val Trp
        35                  40                  45

Phe Gln Asn Arg Arg Ala Lys Trp Arg Lys Thr Glu
    50                  55                  60

(2) INFORMATION FOR SEQ ID NO:18:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:18:

Gln Arg Arg Tyr Arg Thr Thr Phe Thr Ser Phe Gln Leu Glu Glu Leu
1               5                   10                  15

Glu Lys Ala Phe Ser Arg Thr His Tyr Pro Asp Val Phe Thr Arg Glu
            20                  25                  30

Glu Leu Ala Met Lys Ile Gly Leu Thr Glu Ala Arg Ile Gln Val Trp
        35                  40                  45

Phe Gln Asn Arg Arg Ala Lys Trp Arg Lys Gln Glu
    50                  55                  60

(2) INFORMATION FOR SEQ ID NO:19:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:19:

Gln Arg Arg Tyr Arg Thr Thr Phe Thr Ser Phe Gln Leu Glu Glu Leu
1               5                   10                  15

Glu Lys Ala Phe Ser Arg Thr His Tyr Pro Asp Val Phe Thr Arg Glu
            20                  25                  30

Glu Leu Ala Met Lys Ile Gly Leu Thr Glu Ala Arg Ile Gln Val Trp
            35                  40                  45

Phe Gln Asn Arg Arg Ala Lys Trp Arg Lys Gln Glu
    50                  55                  60

(2) INFORMATION FOR SEQ ID NO:20:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:20:

Lys Arg Arg His Arg Thr Thr Phe Thr Ser Leu Gln Leu Glu Glu Leu
1               5                   10                  15

Glu Lys Val Phe Gln Lys Thr His Tyr Pro Asp Val Tyr Val Arg Glu
            20                  25                  30

Gln Leu Ala Leu Arg Thr Glu Leu Thr Glu Ala Arg Val Gln Val Trp
            35                  40                  45

Phe Gln Asn Arg Arg Ala Lys Trp Arg Lys Arg Glu
    50                  55                  60

(2) INFORMATION FOR SEQ ID NO:21:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:21:

Gln Arg Arg Asn Arg Thr Thr Phe Asn Ser Ser Gln Leu Gln Ala Leu
1               5                   10                  15

Glu Arg Val Phe Glu Arg Thr His Tyr Pro Asp Ala Phe Val Arg Glu
            20                  25                  30

Asp Leu Ala Arg Arg Val Asn Leu Thr Glu Ala Arg Val Gln Val Trp
            35                  40                  45

Phe Gln Asn Arg Arg Ala Lys Phe Arg Arg Asn Glu
    50                  55                  60

(2) INFORMATION FOR SEQ ID NO:22:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:22:

Gln Arg Arg Asn Arg Thr Thr Phe Asn Ser Ser Gln Leu Gln Ala Leu
1               5                   10                  15

Glu Arg Val Phe Glu Arg Thr His Tyr Pro Asp Ala Phe Val Arg Glu
            20                  25                  30

Glu Leu Ala Arg Arg Val Asn Leu Ser Glu Ala Arg Val Gln Val Trp
        35                  40                  45

Phe Gln Asn Arg Arg Ala Lys Phe Arg Arg Asn Glu
50                  55                  60

(2) INFORMATION FOR SEQ ID NO:23:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:23:

Gln Arg Arg Ile Arg Thr Thr Phe Thr Ser Ala Gln Leu Lys Glu Leu
1               5                   10                  15

Glu Arg Val Phe Ala Glu Thr His Tyr Pro Asp Ile Tyr Thr Arg Glu
            20                  25                  30

Glu Leu Ala Leu Lys Ile Asp Leu Thr Glu Ala Arg Val Gln Val Trp
        35                  40                  45

Phe Gln Asn Arg Arg Ala Lys Phe Arg Lys Gln Glu
50                  55                  60

(2) INFORMATION FOR SEQ ID NO:24:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:24:

Gln Arg Arg Asn Arg Thr Thr Phe Asn Ser Ser Gln Leu Gln Ala Leu
1               5                   10                  15

Glu Arg Val Phe Glu Arg Thr His Tyr Pro Asp Ala Phe Val Arg Glu
            20                  25                  30

Asp Leu Ala Arg Arg Val Asn Leu Thr Glu Ala Arg Val Gln Val Trp
        35                  40                  45

Phe Gln Asn Arg Arg Ala Lys Phe Arg Arg Asn Glu
50                  55                  60

(2) INFORMATION FOR SEQ ID NO:25:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:25:

```
Lys Arg Arg His Arg Thr Ile Phe Thr Ser Tyr Gln Leu Glu Leu
1               5                   10                  15

Glu Lys Ala Phe Asn Glu Ala His Tyr Pro Asp Val Tyr Ala Arg Glu
            20                  25                  30

Met Leu Ala Met Lys Thr Glu Leu Pro Glu Asp Arg Ile Gln Val Trp
            35                  40                  45

Phe Gln Asn Arg Arg Ala Lys Trp Arg Lys Arg Glu
            50                  55                  60
```

(2) INFORMATION FOR SEQ ID NO:26:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:26:

```
Gln Lys Arg His Arg Thr Arg Phe Thr Pro Ala Gln Leu Asn Glu Leu
1               5                   10                  15

Glu Arg Ser Phe Ala Lys Thr His Tyr Pro Asp Ile Phe Met Arg Glu
            20                  25                  30

Glu Leu Ala Leu Arg Ile Gly Leu Thr Glu Ser Arg Val Gln Val Trp
            35                  40                  45

Phe Gln Asn Arg Arg Ala Lys Trp Lys Lys Arg Lys
            50                  55                  60
```

(2) INFORMATION FOR SEQ ID NO:27:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:27:

```
Ser Ser Leu Ala Ser Leu Arg Leu Lys Ala Lys Gln His Ser
1               5                   10
```

(2) INFORMATION FOR SEQ ID NO:28:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:28:

```
Ser Ser Leu Ala Ser Leu Arg Leu Lys Ala Lys Gln His Ser
1               5                   10
```

(2) INFORMATION FOR SEQ ID NO:29:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:29:

Asn Ser Ile Ala Ser Leu Arg Leu Lys Ala Lys Glu Phe Ser
1               5                   10

(2) INFORMATION FOR SEQ ID NO:30:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:30:

Asn Ser Ile Ala Asn Leu Arg Leu Lys Ala Lys Glu Tyr Ser
1               5                   10

(2) INFORMATION FOR SEQ ID NO:31:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:31:

Ser Ser Ile Ala Val Leu Arg Met Lys Ala Lys Glu His Thr
1               5                   10

(2) INFORMATION FOR SEQ ID NO:32:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:32:

Ser Ser Ile Ala Ala Leu Arg Leu Lys Ala Arg Glu His Glu
1               5                   10

(2) INFORMATION FOR SEQ ID NO:33:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:33:

```
Asn Ser Ile Ala Asn Leu Arg Leu Lys Ala Lys Glu Tyr Ser
1               5                   10
```

(2) INFORMATION FOR SEQ ID NO:34:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:34:

```
Ala Ser Val Ala Ala Leu Arg Met Lys Ala Arg Glu His Ser
1               5                   10
```

(2) INFORMATION FOR SEQ ID NO:35:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:35:

```
Asn Ser Ile Ala Ala Leu Arg Ala Lys Ala Gln Glu His Ser
1               5                   10
```

(2) INFORMATION FOR SEQ ID NO:36:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:36:

```
Thr Ser Ile Ala Ser Leu Arg Arg Lys Ala Leu Glu His Thr
1               5                   10
```

(2) INFORMATION FOR SEQ ID NO:37:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

```
GGCCTCCAGC TCCTGG                                             16
```

(2) INFORMATION FOR SEQ ID NO:38:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

GGCCTCCNGC TCCTGG                                               16

(2) INFORMATION FOR SEQ ID NO:39:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

CTGGCTCCTA CCCGG                                                15

(2) INFORMATION FOR SEQ ID NO:40:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

CTGGCTNCTA CCCGG                                                15

(2) INFORMATION FOR SEQ ID NO:41:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

TTTCTTCGCG TGTGG                                                15

(2) INFORMATION FOR SEQ ID NO:42:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

GGACATGTCC ACACG                                                15

(2) INFORMATION FOR SEQ ID NO:43:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

TTTCTTCGCG TGTGG                                                15

(2) INFORMATION FOR SEQ ID NO:44:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

GGACATGTCC CCACG         15

(2) INFORMATION FOR SEQ ID NO:45:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

GGGGGCGGTT GGGGC         15

(2) INFORMATION FOR SEQ ID NO:46:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

GGGGGCGGNT GGGGC         15

(2) INFORMATION FOR SEQ ID NO:47:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

TTTGGCCCGA CGATT         15

(2) INFORMATION FOR SEQ ID NO:48:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

TTTGGCCGGA CGATT         15

(2) INFORMATION FOR SEQ ID NO:49:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:49:

CAACTGGGCC GCCA                                            14

(2) INFORMATION FOR SEQ ID NO:50:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:50:

ACAACTGAGC CGCCA                                           15

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:51:

GAAAGTTCAA ACTCATCAAG                                      20

(2) INFORMATION FOR SEQ ID NO:52:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:52:

GAGTACTTAC CCACACAAGT A                                    21

(2) INFORMATION FOR SEQ ID NO:53:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:53:

GGTCTCTTTC TTCCACCCA                                       19

(2) INFORMATION FOR SEQ ID NO:54:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:54:

TGTAGGTAAG GGTATTTTAC                                                        20

(2) INFORMATION FOR SEQ ID NO:55:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

TAAAATTTGA TTTTCGAGAG AG                                                     22

(2) INFORMATION FOR SEQ ID NO:56:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

CTGAATACAG CAGAATTTAC C                                                      21

(2) INFORMATION FOR SEQ ID NO:57:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

TGAAGTGTGT TTGCCCTCA                                                         19

(2) INFORMATION FOR SEQ ID NO:58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:58:

ATACCAAGAG TAAAACTTAC                                                        20

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

TTTGTCGGTT GCTTTTTAGG                                                    20

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

CAAGGTCAAC GATGACTCAC                                                    20

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:61:

CCCACTCCAA ATAAAGCATC                                                    20

(2) INFORMATION FOR SEQ ID NO:62:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

CATTACCTTC ACAGTCATTC                                                    20

(2) INFORMATION FOR SEQ ID NO:63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:63:

TTTGAATGTA TTGTGCTGTT G                                                  21

(2) INFORMATION FOR SEQ ID NO:64:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:64:

TAATGCAATA AATACTTGTT GC                                                 22

(2) INFORMATION FOR SEQ ID NO:65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:65:

AACACTAATC TGACCTGTCT                                        20

(2) INFORMATION FOR SEQ ID NO:66:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:66:

CAAACAAAAG GTAAATAAAG CAA                                   23

(2) INFORMATION FOR SEQ ID NO:67:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:67:

GTAGCATCAT TACTAAGCAA TT                                    22

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:68:

GACACAGTTC CAGACAACCA                                        20

(2) INFORMATION FOR SEQ ID NO:69:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:69:

TAAATTCAGC CATATTTGAA ATT                                   23

(2) INFORMATION FOR SEQ ID NO:70:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:70:

TCCACATCTG TTCAAGTAAC                                           20

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:71:

AAATCACAGT GCTGTGTTCT                                           20

(2) INFORMATION FOR SEQ ID NO:72:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:72:

ACAGCTTAAA ACTGAAGCAG                                           20

(2) INFORMATION FOR SEQ ID NO:73:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:73:

TATTTGTTGT GTGCTTTCTT G                                         21

(2) INFORMATION FOR SEQ ID NO:74:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:74:

AAAATCGCCC ATCCCAAAG                                            19

(2) INFORMATION FOR SEQ ID NO:75:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:75:

GGTGTATTTA ACAAACTTGA AT                                                                22

(2) INFORMATION FOR SEQ ID NO:76:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:76:

GAAAGACTGT GTAACATCTC                                                                   20

(2) INFORMATION FOR SEQ ID NO:77:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:77:

CCCACTTGTG AATTTGTTTC                                                                   20

(2) INFORMATION FOR SEQ ID NO:78:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:78:

TTAGGTAATT GCCACATAAT TT                                                                22

(2) INFORMATION FOR SEQ ID NO:79:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:79:

AAATTTAATT GCATCTATTG AC                                                                22

(2) INFORMATION FOR SEQ ID NO:80:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:80:

AGGTATATTG GAGAACTAGT                                                    20

(2) INFORMATION FOR SEQ ID NO:81:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:81:

ATAACTGCAC GGGATTCTTG                                                    20

(2) INFORMATION FOR SEQ ID NO:82:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:82:

TGTCCAAATA TGTGAATTTG C                                                  21

(2) INFORMATION FOR SEQ ID NO:83:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:83:

CCTAAATATT GCACTAGTTC ATAAT                                              25

(2) INFORMATION FOR SEQ ID NO:84:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:84:

CCCTCCTCCC CAGCACATGT                                                    20

(2) INFORMATION FOR SEQ ID NO:85:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:85:

TCTCTCCCGT ACTCTGTCTT                                                    20

(2) INFORMATION FOR SEQ ID NO:86:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:86:

TCCCCTTCAC TGTAGACCAC                                    20

(2) INFORMATION FOR SEQ ID NO:87:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:87:

GAAAGTAAAA GTAATGTCTT GG                                 22

(2) INFORMATION FOR SEQ ID NO:88:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:88:

ATCTCTCTGT CCATCAGCAA                                    20

(2) INFORMATION FOR SEQ ID NO:89:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:89:

CTGATGACCT CTGTTTGTGT                                    20

(2) INFORMATION FOR SEQ ID NO:90:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:90:

AAAGAGGTTT CCAGTACCAA                                    20

(2) INFORMATION FOR SEQ ID NO:91:

(i) SEQUENCE CHARACTERISTICS:
        (A) LENGTH: 21 base pairs (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:91:

TGAGATTGTC TCAAATTTTG G                                              21

(2) INFORMATION FOR SEQ ID NO:92:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:92:

TCCTTGCTTC ATCTGCTTTG                                                20

(2) INFORMATION FOR SEQ ID NO:93:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:93:

AATATCCTCT CTCCCTCCTT                                                20

(2) INFORMATION FOR SEQ ID NO:94:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:94:

ACCGAGGAGC CAGGATAAAA                                                20

(2) INFORMATION FOR SEQ ID NO:95:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:95:

GAATATTGAA ATTTCTTTTG TC                                             22

(2) INFORMATION FOR SEQ ID NO:96:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:96:

TTCTTCTTGA CTTTCCTTTT A                                                21

(2) INFORMATION FOR SEQ ID NO:97:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:97:

AAGAATTGGGAC GTGCAGTG                                                  20

(2) INFORMATION FOR SEQ ID NO:98:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:98:

AGCAGCTTCC ACATTTCCTG                                                  20

(2) INFORMATION FOR SEQ ID NO:99:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:99:

GCTCGCTTCC CAAAATTAGC                                                  20

(2) INFORMATION FOR SEQ ID NO:100:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:100:

CATTATAAGT CGACTATAAG TG                                               22

(2) INFORMATION FOR SEQ ID NO:101:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:101:

```
GAGTGTTTAG TTTTGCTTGT G                                              21

(2) INFORMATION FOR SEQ ID NO:102:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:102:

CCCACTTTTG GGTATGTATC C                                              21

(2) INFORMATION FOR SEQ ID NO:103:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:103:

TAACCTCTAG CCAATCTGAT C                                              21

(2) INFORMATION FOR SEQ ID NO:104:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:104:

TTGACCACAT CAGCCCAAC                                                 19

(2) INFORMATION FOR SEQ ID NO:105:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:105:

TCTATCTCCT CTTGGATTCA G                                              21

(2) INFORMATION FOR SEQ ID NO:106:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:106:

AATTGTAGAA TGTAGGTCAA AG                                             22

(2) INFORMATION FOR SEQ ID NO:107:
```

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:107:

CCACGCTTTA AATTCGACTC                                                  20

(2) INFORMATION FOR SEQ ID NO:108:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:108:

TTGGTTATTT GGCAACATTC                                                  20

(2) INFORMATION FOR SEQ ID NO:109:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:109:

CTGTCTCCCA ATTCCTCACT                                                  20

(2) INFORMATION FOR SEQ ID NO:110:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:110:

GTCAGCAGTC TGTGACAAGG                                                  20

(2) INFORMATION FOR SEQ ID NO:111:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:111:

GATAAAAGCC AGCAGGGGAA                                                  20

(2) INFORMATION FOR SEQ ID NO:112:

(i) SEQUENCE CHARACTERISTICS:
            (A) LENGTH: 20 base pairs
            (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO:112:

GAGGGAACTG TAATCTCGCA                                                    20

(2) INFORMATION FOR SEQ ID NO:113:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:113:

GTAATCTGCA CTGTGGCATC                                                    20

(2) INFORMATION FOR SEQ ID NO:114:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:114:

CCAGTTGTTG TAGGAATAGC C                                                  21

(2) INFORMATION FOR SEQ ID NO:115:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:115:

AGTTCAATGG GCTCATGCAG                                                    20

(2) INFORMATION FOR SEQ ID NO:116:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:116:

GGGGAAAACA TGCTCTGTGA                                                    20

(2) INFORMATION FOR SEQ ID NO:117:

(i) SEQUENCE CHARACTERISTICS:
        (A) LENGTH: 1929 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:117:

```
CGAGAAAGCT GGAGAGGAGC AGAAAGAAAC TGCCAGTGGC GGCTAGATTT CGGAGGCCCC      60
AGTGCACCCG TGGACTCCTT CGGAACTTGG CACCCTCAGG AGCCCTGCAG TCCTCTCAGG     120
CCCGGCTTTC GGGCGCTTGC CGTGCAGCCG GAGGCTCGGC TCGCTGGAAA TCGCCCCGGG     180
AAGCAGTGGG ACGCGGAGAC AGCAGCTCTC TCCCGGTAGC CGGTAAGTGG AGGCGCTTCT     240
TACAGCCTTC CTTTCTTCTG TTTTGCAGAT AACGGGGAAA TGGAGACCAA CTGCCGCAAA     300
CTGGTGTCGG CGTGTCTGCA ATTAGGTAAG AACCCCCTTC TCCTGCCCGG GTCATCGGAC     360
TGTGTTTCAG TTTTCAGAGA AAGATAAAAG CCAGCAGGGG AAGAATGAGG ACGTGGGCGC     420
CGAGGACCCG TCTAAGAAGA AGCGGCAAAG GCGGCAGCGG ACTCACTTTA CCAGCCAGCA     480
GCTCCAGCAG CTGGAGGCCA CTTTCCAGAG GAACCGCTAC CCGGACATGT CCACACGCGA     540
AGAAATCGCT GTGTGGACCA ACCTTACGGA AGCCCGAGTC CGGGTGAGCC AGCACGGAGT     600
CTGGGAGGCT GTTTGCTCCC TTGCCCCAAC CGCCCCCAGG TTTGGTTCAA GAATCGTCGG     660
GCCAAATGGA GAAAGAGGGA GCGCAACCAG CAGGCCGAGC TATGCAAGAA TGGCTTCGGG     720
CCGCAGTTCA ATGGGCTCAT GCAGCCCTAC GACGACATGT ACCCAGGCTA TTCCTACAAC     780
AACTGGGCCG CCAAGGGCCT TACATCCGCC TCCCTATCCA CCAAGAGCTT CCCCTTCTTC     840
AACTCTATGA ACGTCAACCC CCTGTCATCA CAGAGCATGT TTTCCCCACC CAACTCTATC     900
TCGTCCATGA GCATGTCGTC CAGCATGGTG CCCTCAGCAG TGACAGGCGT CCCGGGCTCC     960
AGTCTCAACA GCCTGAATAA CTTGAACAAC CTGAGTAGCC CGTCGCTGAA TTCCGCGGTG    1020
CCGACGCCTG CCTGTCCTTA CGCGCCGCCG ACTCCTCCGT ATGTTTATAG GGACACGTGT    1080
AACTCGAGCC TGGCCAGCCT GAGACTGAAA GCAAAGCAGC ACTCCAGCTT CGGCTACGCC    1140
AGCGTGCAGA AACCGGCCTC CAACCTGAGT GCTTGCCAGT ATGCAGTGGA CCGGCCCGTG    1200
TGAGCCGCAC CCACAGCGCC GGGATCCTAG GACCTTGCCG GATGGGCAA CTCCGCCCTT     1260
GAAAGACTGG GAATTATGCT AGAAGGTCGT GGGCACTAAA GAAAGGGAGA GAAAGAGAAG    1320
CTATATAGAG AAAAGGAAAC CACTGAATCA AGAGAGAGC TCCTTTGATT TCAAAGGGAT     1380
GTCCTCAGTG TCTGACATCT TTCACTACAA GTATTTCTAA CAGTTGCAAG ACACATACA     1440
CAAACAAATG TTTTGACTGG ATATGACATT TTAACATTAC TATAAGCTTG TTATTTTTTA    1500
AGTTTAGCAT TGTTAACATT TAAATGACTG AAAGGATGTA TATATATCGA AATGTCAAAT    1560
TAATTTTATA AAAGCAGTTG TTAGTAATAT CACAACAGTG TTTTTAAAGG TTAGGCTTTA    1620
AAATAAAGCA TGTTATACAG AAGCGATTAG GATTTTTCGC TTGCGAGCAA GGGAGTGTAT    1680
ATACTAAATG CCACACTGTA TGTTTCTAAC ATATTATTAT TATTATAAAA AATGTGTGAA    1740
TATCAGTTTT AGAATAGTTT GTGTGGTGGA TGCAATGATG TTTCTGAAAC TGCTATGTAC    1800
AACCTACCCT GTGTATAACA TTTCGTACAA TATTATTGTT TTACTTTTCA GCAAATATGA    1860
AACAAATGTG TTTTATTTTC ATGGGAGTAA AATATACTGC ATACAAAAAA AAAAAAAAAA    1920
AAAAAAAAA                                                            1929
```

(2) INFORMATION FOR SEQ ID NO:118:

(i) SEQUENCE CHARACTERISTICS:
      (A) LENGTH: 1929 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:118:

```
CGAGAAAGCT GGAGAGGAGC AGAAAGAAAC TGCCAGTGGC GGCTAGATTT CGGAGGCCCC      60
AGTGCACCCG TGGACTCCTT CGGAACTTGG CACCCTCAGG AGCCCTGCAG TCCTCTCAGG     120
CCCGGCTTTC GGGCGCTTGC CGTGCAGCCG GAGGCTCGGC TCGCTGGAAA TCGCCCGGG     180
AAGCAGTGGG ACGCGGAGAC AGCAGCTCTC TCCCGGTAGC CGGTAAGTGG AGGCGCTTCT    240
TACAGCCTTC CTTTCTTCTG TTTTGCAGAT AACGGGAAA TGGAGACCAA CTGCCGCAAA     300
CTGGTGTCGG CGTGTCTGCA ATTAGGTAAG AACCCCCTTC TCCTGCCCGG GTCATCGGAC    360
TGTGTTTCAG TTTTCAGAGA AAGATAAGGG CCAGCAAGGA AAGAATGAGG ATGTGGGCGC    420
CGAGGACCCG TCCAAGAAGA AGCGGCAACG CCGGCAGAGG ACTCATTTCA CTAGCCAGCA    480
GCTGCAGCAG CTGGAAGCCA CTTTCCAGAG AAACCGCTAC CCAGACATGT CCACTCGCGA    540
AGAAATCGCT GTGTGGACCA ACCTTACGGA AGCCCGAGTC CGGGTGAGCC AGCACGGAGT    600
CTGGGAGGCT GTTTGCTCCC TTGCCCCAAC CGCCCCAGG TTTGGTTCAA GAATCGCCGG     660
GCCAAATGGA GAAAGCGGGA ACGCAACCAG CAGGCCGAGC TGTGCAAGAA TGGCTTTGGG    720
CCGCAGTTCA ACGGGCTCAT GCAGCCCTAC GACGACATGT ACCCCGGCTA TTCGTACAAC    780
AACTGGGCTG CCAAGGGCCT CACGTCAGCG TCTCTGTCCA CCAAGAGCTT CCCCTTCTTC    840
AACTCCATGA ACGTCAATCC CCTGTCGTCT CAGAGTATGT TTTCCCCGCC CAACTCCATC    900
TCATCTATGA GTATGTCGTC CAGCATGGTG CCCTCCGCGG TGACCGGCGT CCCGGGCTCC    960
AGCCTCAATA GCCTGAATAA CTTGAACAAC CTGAGCAGCC CGTCGCTGAA TTCCGCGGTG   1020
CCCACGCCCG CCTGTCCTTA CGCGCCGCCG ACTCCTCCGT ACGTTTATAG GGACACATGT   1080
AACTCGAGCC TGGCCAGCCT GAGACTGAAA GCAAAGCAGC ACTCCAGCTT CGGCTACGCC   1140
AGCGTGCAGA ACCCGGCCTC CAACCTGAGT GCTTGCCAGT ATGCAGTGGA CCCGCCCGTG   1200
TGAGCCGCAC CCACAGCGCC GGGATCCTAG GACCTTGCCG GATGGGCAA CTCCGCCCTT    1260
GAAAGACTGG GAATTATGCT AGAAGGTCGT GGGCACTAAA GAAAGGGAGA GAAAGAGAAG   1320
CTATATAGAG AAAAGGAAAC CACTGAATCA AGAGAGAGC TCCTTTGATT TCAAAGGGAT    1380
GTCCTCAGTG TCTGACATCT TTCACTACAA GTATTTCTAA CAGTTGCAAG ACACATACA    1440
CAAACAAATG TTTTGACTGG ATATGACATT TTAACATTAC TATAAGCTTG TTATTTTTA    1500
AGTTTAGCAT TGTTAACATT TAAATGACTG AAAGGATGTA TATATATCGA AATGTCAAAT   1560
TAATTTTATA AAAGCAGTTG TTAGTAATAT CACAACAGTG TTTTTAAAGG TTAGGCTTTA   1620
AAATAAAGCA TGTTATACAG AAGCGATTAG GATTTTTCGC TTGCGAGCAA GGGAGTGTAT   1680
ATACTAAATG CCACACTGTA TGTTTCTAAC ATATTATTAT TATTATAAAA AATGTGTGAA   1740
TATCAGTTTT AGAATAGTTT GTGTGGTGGA TGCAATGATG TTTCTGAAAC TGCTATGTAC   1800
AACCTACCCT GTGTATAACA TTTCGTACAA TATTATTGTT TTACTTTTCA GCAAATATGA   1860
AACAAATGTG TTTTATTTTC ATGGGAGTAA AATATACTGC ATACAAAAAA AAAAAAAAAA   1920
AAAAAAAA                                                            1929
```

(2) INFORMATION FOR SEQ ID NO:119:

(i) SEQUENCE CHARACTERISTICS:
        (A) LENGTH: 515 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:119:

| | |
|---|---|
| ACCGCGCCCA GGGCGCGGGG ATCCGAGGAC TGTCGGAGTG GGCAACTCTG CCCCAGAAAG | 60 |
| ACTGAGAATT GTGCTAGAAG TTCGTGCGCA CTATGGGAAG GAAGAGGGGG GAAAAAAGAT | 120 |
| CAGAGGAAAA GAAACCACTG AATTCAAAGA GAGAGCGCCT TTGATTTCAA AGGAATGTCC | 180 |
| CCAAGTGTCT ACGTCTTTCG CTAAGAGTAT TCCCAACAGT TGGAGGACGC GTACGCCCAC | 240 |
| AAATGTTTGA CTGGATATGA CATTTTAACA TTACTATAAG CTTGTTATTT TTTAAGTTTA | 300 |
| GCATTGTTAA CATTAAAATG ACTGAAAGGA TGTATATATA TCGAAATGTC AAATTAATTT | 360 |
| TATAAAGCA GTTGTTAGTA CTATCACTAC AGTGTTTTTA AAGGCTAGGC TTTAAAATAA | 420 |
| AGCATGTTAT ACAGAATCAG TTAGGATTTT TCGCTTGCGA GCAAAGGAAT GTATATACTA | 480 |
| AATGCCACAC TGTATGTTTC TAACATATTA TTATT | 515 |

(2) INFORMATION FOR SEQ ID NO:120:

(i) SEQUENCE CHARACTERISTICS:
        (A) LENGTH: 1775 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 234..1047

(xi) SEQUENCE DESCRIPTION: SEQ ID NO:120:

| | |
|---|---|
| CGAGAAAGCT GGAGAGGAGC AGAAAGAAAC TGCCAGTGGC GGCTAGATTT CGGAGGCCCC | 60 |
| AGTGCACCCG TGGACTCCTT CGGAACTTGG CACCCTCAGG AGCCCTGCAG TCCTCTCAGG | 120 |
| CCCGGCTTTC GGGCGCTTGC CGTGCAGCCG GAGGCTCGGC TCGCTGGAAA TCGCCCCGGG | 180 |
| AAGCAGTGGG ACGCGGAGAC AGCAGCTCTC TCCCGGTAGC CGATAACGGG GAA ATG | 236 |
|                                                                                                                                        Met | |
|                                                                                                                                        1 | |
| GAG ACC AAC TGC CGC AAA CTG GTG TCG GCG TGT CTG CAA TTA GAG AAA<br>Glu Thr Asn Cys Arg Lys Leu Val Ser Ala Cys Leu Gln Leu Glu Lys<br>                5                    10                    15 | 284 |
| GAT AAA AGC CAG CAG GGG AAG AAT GAG GAC GTG GGC GCC GAG GAC CCG<br>Asp Lys Ser Gln Gln Gly Lys Asn Glu Asp Val Gly Ala Glu Asp Pro<br>        20                    25                    30 | 332 |
| TCT AAG AAG AAG CGG CAA AGG CGG CAG CGG ACT CAC TTT ACC AGC CAG<br>Ser Lys Lys Lys Arg Gln Arg Arg Gln Arg Thr His Phe Thr Ser Gln<br>            35                    40                    45 | 380 |
| CAG CTC CAG CAG CAG GAG GCC ACT TTC CAG AGG AAC CGC TAC CCG GAC<br>Gln Leu Gln Gln Gln Glu Ala Thr Phe Gln Arg Asn Arg Tyr Pro Asp<br>50                    55                    60                    65 | 428 |
| ATG TCC ACA CGC GAA GAA ATC GCT GTG TGG ACC AAC CTT ACG GAA GCC<br>Met Ser Thr Arg Glu Glu Ile Ala Val Trp Thr Asn Leu Thr Glu Ala<br>                70                    75                    80 | 476 |
| CGA GTC CGG GTT TGG TTC AAG AAT CGT CGG GCC AAA TGG AGA AAG AGG<br>Arg Val Arg Val Trp Phe Lys Asn Arg Arg Ala Lys Trp Arg Lys Arg<br>        85                    90                    95 | 524 |
| GAG CGC AAC CAG CAG GCC GAG CTA TGC AAG AAT GGC TTC GGG CCG CAG<br>Glu Arg Asn Gln Gln Ala Glu Leu Cys Lys Asn Gly Phe Gly Pro Gln<br>            100                  105                  110 | 572 |
| TTC AAT GGG CTC ATG CAG CCC TAC GAC GAC ATG TAC CCA GGC TAT TCC<br>Phe Asn Gly Leu Met Gln Pro Tyr Asp Asp Met Tyr Pro Gly Tyr Ser<br>       115                    120                  125 | 620 |

-continued

```
TAC AAC AAC TGG GCC GCC AAG GGC CTT ACA TCC GCC TCC CTA TCC ACC         668
Tyr Asn Asn Trp Ala Ala Lys Gly Leu Thr Ser Ala Ser Leu Ser Thr
130                 135                 140                 145

AAG AGC TTC CCC TTC TTC AAC TCT ATG AAC GTC AAC CCC CTG TCA TCA         716
Lys Ser Phe Pro Phe Phe Asn Ser Met Asn Val Asn Pro Leu Ser Ser
            150                 155                 160

CAG AGC ATG TTT TCC CCA CCC AAC TCT ATC TCG TCC ATG AGC ATG TCG         764
Gln Ser Met Phe Ser Pro Pro Asn Ser Ile Ser Ser Met Ser Met Ser
            165                 170                 175

TCC AGC ATG GTG CCC TCA GCA GTG ACA GGC GTC CCG GGC TCC AGT CTC         812
Ser Ser Met Val Pro Ser Ala Val Thr Gly Val Pro Gly Ser Ser Leu
        180                 185                 190

AAC AGC CTG AAT AAC TTG AAC AAC CTG AGT AGC CCG TCG CTG AAT TCC         860
Asn Ser Leu Asn Asn Leu Asn Asn Leu Ser Ser Pro Ser Leu Asn Ser
        195                 200                 205

GCG GTG CCG ACG CCT GCC TGT CCT TAC GCG CCG CCG ACT CCT CCG TAT         908
Ala Val Pro Thr Pro Ala Cys Pro Tyr Ala Pro Pro Thr Pro Pro Tyr
210                 215                 220                 225

GTT TAT AGG GAC ACG TGT AAC TCG AGC CTG GCC AGC CTG AGA CTG AAA         956
Val Tyr Arg Asp Thr Cys Asn Ser Ser Leu Ala Ser Leu Arg Leu Lys
            230                 235                 240

GCA AAG CAG CAC TCC AGC TTC GGC TAC GCC AGC GTG CAG AAA CCG GCC        1004
Ala Lys Gln His Ser Ser Phe Gly Tyr Ala Ser Val Gln Lys Pro Ala
            245                 250                 255

TCC AAC CTG AGT GCT TGC CAG TAT GCA GTG GAC CGG CCC GTG T              1047
Ser Asn Leu Ser Ala Cys Gln Tyr Ala Val Asp Arg Pro Val
        260                 265                 270

GAGCCGCACC CACAGCGCCG GGATCCTAGG ACCTTGCCGG ATGGGCAAC TCCGCCCTTG        1107

AAAGACTGGG AATTATGCTA GAAGGTCGTG GGCACTAAAG AAAGGGAGAG AAAGAGAAGC       1167

TATATAGAGA AAAGGAAACC ACTGAATCAA AGAGAGAGCT CCTTTGATTT CAAAGGGATG       1227

TCCTCAGTGT CTGACATCTT TCACTACAAG TATTTCTAAC AGTTGCAAGG ACACATACAC       1287

AAACAAATGT TTTGACTGGA TATGACATTT TAACATTACT ATAAGCTTGT TATTTTTTAA       1347

GTTTAGCATT GTTAACATTT AAATGACTGA AAGGATGTAT ATATATCGAA ATGTCAAATT       1407

AATTTTATAA AAGCAGTTGT TAGTAATATC ACAACAGTGT TTTTAAAGGT TAGGCTTTAA       1467

AATAAAGCAT GTTATACAGA AGCGATTAGG ATTTTTCGCT TGCGAGCAAG GGAGTGTATA       1527

TACTAAATGC CACACTGTAT GTTTCTAACA TATTATTATT ATTATAAAAA ATGTGTGAAT       1587

ATCAGTTTTA GAATAGTTTG TGTGGTGGAT GCAATGATGT TTCTGAAACT GCTATGTACA       1647

ACCTACCCTG TGTATAACAT TTCGTACAAT ATTATTGTTT TACTTTTCAG CAAATATGAA       1707

ACAAATGTGT TTTATTTTCA TGGGAGTAAA ATATACTGCA TACAAAAAAA AAAAAAAAA       1767

AAAAAAAA                                                              1775
```

(2) INFORMATION FOR SEQ ID NO:121:

(i) SEQUENCE CHARACTERISTICS:
        (A) LENGTH: 271 amino acids
        (B) TYPE: amino acid
        (D) TOPOLOGY: linear (ii) MOLECULE TYPE: protein (xi) SEQUENCE DESCRIPTION: SEQ ID NO:121:

```
Met Glu Thr Asn Cys Arg Lys Leu Val Ser Ala Cys Leu Gln Leu Glu
1               5                   10                  15

Lys Asp Lys Ser Gln Gln Gly Lys Asn Glu Asp Val Gly Ala Glu Asp
```

```
                  20                  25                  30
        Pro Ser Lys Lys Lys Arg Gln Arg Arg Gln Arg Thr His Phe Thr Ser
                 35                  40                  45
        Gln Gln Leu Gln Gln Gln Glu Ala Thr Phe Gln Arg Asn Arg Tyr Pro
                 50                  55                  60
        Asp Met Ser Thr Arg Glu Glu Ile Ala Val Trp Thr Asn Leu Thr Glu
         65                  70                  75                  80
        Ala Arg Val Arg Val Trp Phe Lys Asn Arg Arg Ala Lys Trp Arg Lys
                         85                  90                  95
        Arg Glu Arg Asn Gln Gln Ala Glu Leu Cys Lys Asn Gly Phe Gly Pro
                            100                 105                 110
        Gln Phe Asn Gly Leu Met Gln Pro Tyr Asp Asp Met Tyr Pro Gly Tyr
                        115                 120                 125
        Ser Tyr Asn Asn Trp Ala Ala Lys Gly Leu Thr Ser Ala Ser Leu Ser
                    130                 135                 140
        Thr Lys Ser Phe Pro Phe Phe Asn Ser Met Asn Val Asn Pro Leu Ser
        145                 150                 155                 160
        Ser Gln Ser Met Phe Ser Pro Pro Asn Ser Ile Ser Ser Met Ser Met
                        165                 170                 175
        Ser Ser Ser Met Val Pro Ser Ala Val Thr Gly Val Pro Gly Ser Ser
                    180                 185                 190
        Leu Asn Ser Leu Asn Asn Leu Asn Asn Leu Ser Ser Pro Ser Leu Asn
                    195                 200                 205
        Ser Ala Val Pro Thr Pro Ala Cys Pro Tyr Ala Pro Pro Thr Pro Pro
                210                 215                 220
        Tyr Val Tyr Arg Asp Thr Cys Asn Ser Ser Leu Ala Ser Leu Arg Leu
        225                 230                 235                 240
        Lys Ala Lys Gln His Ser Ser Phe Gly Tyr Ala Ser Val Gln Lys Pro
                        245                 250                 255
        Ala Ser Asn Leu Ser Ala Cys Gln Tyr Ala Val Asp Arg Pro Val
                    260                 265                 270

(2) INFORMATION FOR SEQ ID NO:122:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..814

(xi) SEQUENCE DESCRIPTION: SEQ ID NO:122:

ATG GAG ACC AAC TGC CGC AAA CTG GTG TCG GCG TGT CTG CAA TTA GAG           48
Met Glu Thr Asn Cys Arg Lys Leu Val Ser Ala Cys Leu Gln Leu Glu
 1               5                  10                  15

AAA GAT AAA AGC CAG CAG GGG AAG AAT GAG GAC GTG GGC GCC GAG GAC           96
Lys Asp Lys Ser Gln Gln Gly Lys Asn Glu Asp Val Gly Ala Glu Asp
             20                  25                  30

CCG TCT AAG AAG AAG CGG CAA AGG CGG CAG CGG ACT CAC TTT ACC AGC          144
Pro Ser Lys Lys Lys Arg Gln Arg Arg Gln Arg Thr His Phe Thr Ser
         35                  40                  45

CAG CAG CTC CAG CAG CAG GAG GCC ACT TTC CAG AGG AAC CGC TAC CCG          192
Gln Gln Leu Gln Gln Gln Glu Ala Thr Phe Gln Arg Asn Arg Tyr Pro
     50                  55                  60
```

-continued

```
GAC ATG TCC ACA CGC GAA GAA ATC GCT GTG TGG ACC AAC CTT ACG GAA      240
Asp Met Ser Thr Arg Glu Glu Ile Ala Val Trp Thr Asn Leu Thr Glu
 65              70                  75                  80

GCC CGA GTC CGG GTT TGG TTC AAG AAT CGT CGG GCC AAA TGG AGA AAG      288
Ala Arg Val Arg Val Trp Phe Lys Asn Arg Arg Ala Lys Trp Arg Lys
                 85                  90                  95

AGG GAG CGC AAC CAG CAG GCC GAG CTA TGC AAG AAT GGC TTC GGG CCG      336
Arg Glu Arg Asn Gln Gln Ala Glu Leu Cys Lys Asn Gly Phe Gly Pro
            100                 105                 110

CAG TTC AAT GGG CTC ATG CAG CCC TAC GAC GAC ATG TAC CCA GGC TAT      384
Gln Phe Asn Gly Leu Met Gln Pro Tyr Asp Asp Met Tyr Pro Gly Tyr
        115                 120                 125

TCC TAC AAC AAC TGG GCC GCC AAG GGC CTT ACA TCC GCC TCC CTA TCC      432
Ser Tyr Asn Asn Trp Ala Ala Lys Gly Leu Thr Ser Ala Ser Leu Ser
    130                 135                 140

ACC AAG AGC TTC CCC TTC TTC AAC TCT ATG AAC GTC AAC CCC CTG TCA      480
Thr Lys Ser Phe Pro Phe Phe Asn Ser Met Asn Val Asn Pro Leu Ser
145                 150                 155                 160

TCA CAG AGC ATG TTT TCC CCA CCC AAC TCT ATC TCG TCC ATG AGC ATG      528
Ser Gln Ser Met Phe Ser Pro Pro Asn Ser Ile Ser Ser Met Ser Met
                165                 170                 175

TCG TCC AGC ATG GTG CCC TCA GCA GTG ACA GGC GTC CCG GGC TCC AGT      576
Ser Ser Ser Met Val Pro Ser Ala Val Thr Gly Val Pro Gly Ser Ser
            180                 185                 190

CTC AAC AGC CTG AAT AAC TTG AAC AAC CTG AGT AGC CCG TCG CTG AAT      624
Leu Asn Ser Leu Asn Asn Leu Asn Asn Leu Ser Ser Pro Ser Leu Asn
        195                 200                 205

TCC GCG GTG CCG ACG CCT GCC TGT CCT TAC GCG CCG CCG ACT CCT CCG      672
Ser Ala Val Pro Thr Pro Ala Cys Pro Tyr Ala Pro Pro Thr Pro Pro
    210                 215                 220

TAT GTT TAT AGG GAC ACG TGT AAC TCG AGC CTG GCC AGC CTG AGA CTG      720
Tyr Val Tyr Arg Asp Thr Cys Asn Ser Ser Leu Ala Ser Leu Arg Leu
225                 230                 235                 240

AAA GCA AAG CAG CAC TCC AGC TTC GGC TAC GCC AGC GTG CAG AAA CCG      768
Lys Ala Lys Gln His Ser Ser Phe Gly Tyr Ala Ser Val Gln Lys Pro
                245                 250                 255

GCC TCC AAC CTG AGT GCT TGC CAG TAT GCA GTG GAC CGG CCC GTG T        814
Ala Ser Asn Leu Ser Ala Cys Gln Tyr Ala Val Asp Arg Pro Val
            260                 265                 270

GA                                                                   816
```

(2) INFORMATION FOR SEQ ID NO:123:

(i) SEQUENCE CHARACTERISTICS:
        (A) LENGTH: 1929 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:123:

```
CGAGAAAGCT GGAGAGGAGC AGAAAGAAAC TGCCAGTGGC GGCTAGATTT CGGAGGCCCC      60

AGTGCACCCG TGGACTCCTT CGGAACTTGG CACCCTCAGG AGCCCTGCAG TCCTCTCAGG     120

CCCGGCTTTC GGGCGCTTGC CGTGCAGCCG GAGGCTCGGC TCGCTGGAAA TCGCCCCGGG     180

AAGCAGTGGG ACGCGGAGAC AGCAGCTCTC TCCCGGTAGC CGGTAAGTGG AGGCGCTTCT     240

TACAGCCTTC CTTTCTTCTG TTTTGCAGAT AACGGGAAA TGGAGACCAA CTGCCGCAAA     300

CTGGTGTCGG CGTGTCTGCA ATTAGGTAAG AACCCCCTTC TCCTGCCCGG GTCATCGGAC     360
```

```
TGTGTTTCAG TTTTCAGAGA AAGATAAAAG CCAGCAGGGG AAGAATGAGG ACGTGGGCGC    420

CGAGGACCCG TCTAAGAAGA AGCGGCAAAG GCGGCAGCGG ACTCACTTTA CCAGCCAGCA    480

GCTCCAGCAG CAGGAGGCCA CTTTCCAGAG GAACCGCTAC CCGGACATGT CCACACGCGA    540

AGAAATCGCT GTGTGGACCA ACCTTACGGA AGCCCGAGTC CGGGTGAGCC AGCACGGAGT    600

CTGGGAGGCT GTTTGCTCCC TTGCCCCAAC CGCCCCCAGG TTTGGTTCAA GAATCGTCGG    660

GCCAAATGGA GAAAGAGGGA GCGCAACCAG CAGGCCGAGC TATGCAAGAA TGGCTTCGGG    720

CCGCAGTTCA ATGGGCTCAT GCAGCCCTAC GACGACATGT ACCCAGGCTA TTCCTACAAC    780

AACTGGGCCG CCAAGGGCCT TACATCCGCC TCCCTATCCA CCAAGAGCTT CCCCTTCTTC    840

AACTCTATGA ACGTCAACCC CCTGTCATCA CAGAGCATGT TTTCCCCACC CAACTCTATC    900

TCGTCCATGA GCATGTCGTC CAGCATGGTG CCCTCAGCAG TGACAGGCGT CCCGGGCTCC    960

AGTCTCAACA GCCTGAATAA CTTGAACAAC CTGAGTAGCC CGTCGCTGAA TTCCGCGGTG   1020

CCGACGCCTG CCTGTCCTTA CGCGCCGCCG ACTCCTCCGT ATGTTTATAG GGACACGTGT   1080

AACTCGAGCC TGGCCAGCCT GAGACTGAAA GCAAAGCAGC ACTCCAGCTT CGGCTACGCC   1140

AGCGTGCAGA AACCGGCCTC CAACCTGAGT GCTTGCCAGT ATGCAGTGGA CCGGCCCGTG   1200

TGAGCCGCAC CCACAGCGCC GGGATCCTAG GACCTTGCCG GATGGGGCAA CTCCGCCCTT   1260

GAAAGACTGG GAATTATGCT AGAAGGTCGT GGGCACTAAA GAAAGGGAGA GAAAGAGAAG   1320

CTATATAGAG AAAAGGAAAC CACTGAATCA AAGAGAGAGC TCCTTTGATT TCAAAGGGAT   1380

GTCCTCAGTG TCTGACATCT TTCACTACAA GTATTTCTAA CAGTTGCAAG GACACATACA   1440

CAAACAAATG TTTTGACTGG ATATGACATT TTAACATTAC TATAAGCTTG TTATTTTTA    1500

AGTTTAGCAT TGTTAACATT TAAATGACTG AAAGGATGTA TATATATCGA AATGTCAAAT   1560

TAATTTTATA AAAGCAGTTG TTAGTAATAT CACAACAGTG TTTTTAAAGG TTAGGCTTTA   1620

AAATAAAGCA TGTTATACAG AAGCGATTAG GATTTTTCGC TTGCGAGCAA GGGAGTGTAT   1680

ATACTAAATG CCACACTGTA TGTTTCTAAC ATATTATTAT TATTATAAAA AATGTGTGAA   1740

TATCAGTTTT AGAATAGTTT GTGTGGTGGA TGCAATGATG TTTCTGAAAC TGCTATGTAC   1800

AACCTACCCT GTGTATAACA TTTCGTACAA TATTATTGTT TTACTTTTCA GCAAATATGA   1860

AACAAATGTG TTTTATTTTC ATGGGAGTAA AATATACTGC ATACAAAAAA AAAAAAAAAA   1920

AAAAAAAA                                                            1929

(2) INFORMATION FOR SEQ ID NO:124:

(i) SEQUENCE CHARACTERISTICS:
        (A) LENGTH: 1775 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 234..1047

(xi) SEQUENCE DESCRIPTION: SEQ ID NO:124:

CGAGAAAGCT GGAGAGGAGC AGAAAGAAAC TGCCAGTGGC GGCTAGATTT CGGAGGCCCC     60

AGTGCACCCG TGGACTCCTT CGGAACTTGG CACCCTCAGG AGCCCTGCAG TCCTCTCAGG    120

CCCGGCTTTC GGGCGCTTGC CGTGCAGCCG GAGGCTCGGC TCGCTGGAAA TCGCCCCGGG    180

AAGCAGTGGG ACGCGGAGAC AGCAGCTCTC TCCCGGTAGC CGATAACGGG GAA ATG       236
```

-continued

```
                                                         Met
                                                          1
GAG ACC AAC TGC CGC AAA CTG GTG TCG GCG TGT CTG CAA TTA GAG AAA    284
Glu Thr Asn Cys Arg Lys Leu Val Ser Ala Cys Leu Gln Leu Glu Lys
             5                  10                  15

GAT AAA AGC CAG CAG GGG AAG AAT GAG GAC GTG GGC GCC GAG GAC CCG    332
Asp Lys Ser Gln Gln Gly Lys Asn Glu Asp Val Gly Ala Glu Asp Pro
         20                  25                  30

TCT AAG AAG AAG CGG CAA AGG CGG CAG CGG ACT CAC TTT ACC AGC CAG    380
Ser Lys Lys Lys Arg Gln Arg Arg Gln Arg Thr His Phe Thr Ser Gln
     35                  40                  45

CAG CTC CAG CAG CTG GAG GCC ACT TTC CAG AGG AAC CGC TAC CCG GAC    428
Gln Leu Gln Gln Leu Glu Ala Thr Phe Gln Arg Asn Arg Tyr Pro Asp
 50                  55                  60                  65

ATG TCC CCA CGC GAA GAA ATC GCT GTG TGG ACC AAC CTT ACG GAA GCC    476
Met Ser Pro Arg Glu Glu Ile Ala Val Trp Thr Asn Leu Thr Glu Ala
                 70                  75                  80

CGA GTC CGG GTT TGG TTC AAG AAT CGT CGG GCC AAA TGG AGA AAG AGG    524
Arg Val Arg Val Trp Phe Lys Asn Arg Arg Ala Lys Trp Arg Lys Arg
             85                  90                  95

GAG CGC AAC CAG CAG GCC GAG CTA TGC AAG AAT GGC TTC GGG CCG CAG    572
Glu Arg Asn Gln Gln Ala Glu Leu Cys Lys Asn Gly Phe Gly Pro Gln
         100                 105                 110

TTC AAT GGG CTC ATG CAG CCC TAC GAC GAC ATG TAC CCA GGC TAT TCC    620
Phe Asn Gly Leu Met Gln Pro Tyr Asp Asp Met Tyr Pro Gly Tyr Ser
     115                 120                 125

TAC AAC AAC TGG GCC GCC AAG GGC CTT ACA TCC GCC TCC CTA TCC ACC    668
Tyr Asn Asn Trp Ala Ala Lys Gly Leu Thr Ser Ala Ser Leu Ser Thr
130                 135                 140                 145

AAG AGC TTC CCC TTC TTC AAC TCT ATG AAC GTC AAC CCC CTG TCA TCA    716
Lys Ser Phe Pro Phe Phe Asn Ser Met Asn Val Asn Pro Leu Ser Ser
                 150                 155                 160

CAG AGC ATG TTT TCC CCA CCC AAC TCT ATC TCG TCC ATG AGC ATG TCG    764
Gln Ser Met Phe Ser Pro Pro Asn Ser Ile Ser Ser Met Ser Met Ser
             165                 170                 175

TCC AGC ATG GTG CCC TCA GCA GTG ACA GGC GTC CCG GGC TCC AGT CTC    812
Ser Ser Met Val Pro Ser Ala Val Thr Gly Val Pro Gly Ser Ser Leu
         180                 185                 190

AAC AGC CTG AAT AAC TTG AAC AAC CTG AGT AGC CCG TCG CTG AAT TCC    860
Asn Ser Leu Asn Asn Leu Asn Asn Leu Ser Ser Pro Ser Leu Asn Ser
     195                 200                 205

GCG GTG CCG ACG CCT GCC TGT CCT TAC GCG CCG CCG ACT CCT CCG TAT    908
Ala Val Pro Thr Pro Ala Cys Pro Tyr Ala Pro Pro Thr Pro Pro Tyr
210                 215                 220                 225

GTT TAT AGG GAC ACG TGT AAC TCG AGC CTG GCC AGC CTG AGA CTG AAA    956
Val Tyr Arg Asp Thr Cys Asn Ser Ser Leu Ala Ser Leu Arg Leu Lys
                 230                 235                 240

GCA AAG CAG CAC TCC AGC TTC GGC TAC GCC AGC GTG CAG AAA CCG GCC   1004
Ala Lys Gln His Ser Ser Phe Gly Tyr Ala Ser Val Gln Lys Pro Ala
             245                 250                 255

TCC AAC CTG AGT GCT TGC CAG TAT GCA GTG GAC CGG CCC GTG T         1047
Ser Asn Leu Ser Ala Cys Gln Tyr Ala Val Asp Arg Pro Val
         260                 265                 270

GAGCCGCACC CACAGCGCCG GGATCCTAGG ACCTTGCCGG ATGGGCAAC TCCGCCCTTG   1107

AAAGACTGGG AATTATGCTA GAAGGTCGTG GGCACTAAAG AAAGGGAGAG AAAGAGAAGC  1167

TATATAGAGA AAAGGAAACC ACTGAATCAA AGAGAGAGCT CCTTTGATTT CAAAGGGATG  1227

TCCTCAGTGT CTGACATCTT TCACTACAAG TATTTCTAAC AGTTGCAAGG ACACATACAC  1287
```

-continued

```
AAACAAATGT TTTGACTGGA TATGACATTT TAACATTACT ATAAGCTTGT TATTTTTTAA    1347

GTTTAGCATT GTTAACATTT AAATGACTGA AAGGATGTAT ATATATCGAA ATGTCAAATT    1407

AATTTTATAA AAGCAGTTGT TAGTAATATC ACAACAGTGT TTTTAAAGGT TAGGCTTTAA    1467

AATAAAGCAT GTTATACAGA AGCGATTAGG ATTTTTCGCT TGCGAGCAAG GGAGTGTATA    1527

TACTAAATGC CACACTGTAT GTTTCTAACA TATTATTATT ATTATAAAAA ATGTGTGAAT    1587

ATCAGTTTTA GAATAGTTTG TGTGGTGGAT GCAATGATGT TTCTGAAACT GCTATGTACA    1647

ACCTACCCTG TGTATAACAT TTCGTACAAT ATTATTGTTT TACTTTTCAG CAAATATGAA    1707

ACAAATGTGT TTTATTTTCA TGGGAGTAAA ATATACTGCA TACAAAAAAA AAAAAAAAA     1767

AAAAAAA                                                             1775
```

(2) INFORMATION FOR SEQ ID NO:125:

(i) SEQUENCE CHARACTERISTICS:
        (A) LENGTH: 271 amino acids
        (B) TYPE: amino acid
        (D) TOPOLOGY: linear (ii) MOLECULE TYPE: protein (xi) SEQUENCE DESCRIPTION: SEQ ID NO:125:

```
Met Glu Thr Asn Cys Arg Lys Leu Val Ser Ala Cys Leu Gln Leu Glu
  1               5                  10                  15

Lys Asp Lys Ser Gln Gln Gly Lys Asn Glu Asp Val Gly Ala Glu Asp
             20                  25                  30

Pro Ser Lys Lys Arg Gln Arg Gln Arg Thr His Phe Thr Ser
         35                  40                  45

Gln Gln Leu Gln Gln Leu Glu Ala Thr Phe Gln Arg Asn Arg Tyr Pro
     50                  55                  60

Asp Met Ser Pro Arg Glu Glu Ile Ala Val Trp Thr Asn Leu Thr Glu
 65                  70                  75                  80

Ala Arg Val Arg Val Trp Phe Lys Asn Arg Arg Ala Lys Trp Arg Lys
             85                  90                  95

Arg Glu Arg Asn Gln Gln Ala Glu Leu Cys Lys Asn Gly Phe Gly Pro
            100                 105                 110

Gln Phe Asn Gly Leu Met Gln Pro Tyr Asp Asp Met Tyr Pro Gly Tyr
            115                 120                 125

Ser Tyr Asn Asn Trp Ala Ala Lys Gly Leu Thr Ser Ala Ser Leu Ser
            130                 135                 140

Thr Lys Ser Phe Pro Phe Phe Asn Ser Met Asn Val Asn Pro Leu Ser
145                 150                 155                 160

Ser Gln Ser Met Phe Ser Pro Asn Ser Ile Ser Ser Met Ser Met
                165                 170                 175

Ser Ser Ser Met Val Pro Ser Ala Val Thr Gly Val Pro Gly Ser Ser
            180                 185                 190

Leu Asn Ser Leu Asn Asn Leu Asn Asn Leu Ser Ser Pro Ser Leu Asn
            195                 200                 205

Ser Ala Val Pro Thr Pro Ala Cys Pro Tyr Ala Pro Pro Thr Pro Pro
            210                 215                 220

Tyr Val Tyr Arg Asp Thr Cys Asn Ser Ser Leu Ala Ser Leu Arg Leu
225                 230                 235                 240

Lys Ala Lys Gln His Ser Ser Phe Gly Tyr Ala Ser Val Gln Lys Pro
                245                 250                 255

Ala Ser Asn Leu Ser Ala Cys Gln Tyr Ala Val Asp Arg Pro Val
```

-continued

```
            260              265              270
```

(2) INFORMATION FOR SEQ ID NO:126:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..814

(xi) SEQUENCE DESCRIPTION: SEQ ID NO:126:

```
ATG GAG ACC AAC TGC CGC AAA CTG GTG TCG GCG TGT CTG CAA TTA GAG      48
Met Glu Thr Asn Cys Arg Lys Leu Val Ser Ala Cys Leu Gln Leu Glu
 1               5                  10                  15

AAA GAT AAA AGC CAG CAG GGG AAG AAT GAG GAC GTG GGC GCC GAG GAC      96
Lys Asp Lys Ser Gln Gln Gly Lys Asn Glu Asp Val Gly Ala Glu Asp
            20                  25                  30

CCG TCT AAG AAG AAG CGG CAA AGG CGG CAG CGG ACT CAC TTT ACC AGC     144
Pro Ser Lys Lys Lys Arg Gln Arg Arg Gln Arg Thr His Phe Thr Ser
        35                  40                  45

CAG CAG CTC CAG CAG CTG GAG GCC ACT TTC CAG AGG AAC CGC TAC CCG     192
Gln Gln Leu Gln Gln Leu Glu Ala Thr Phe Gln Arg Asn Arg Tyr Pro
    50                  55                  60

GAC ATG TCC CCA CGC GAA GAA ATC GCT GTG TGG ACC AAC CTT ACG GAA     240
Asp Met Ser Pro Arg Glu Glu Ile Ala Val Trp Thr Asn Leu Thr Glu
65                  70                  75                  80

GCC CGA GTC CGG GTT TGG TTC AAG AAT CGT CGG GCC AAA TGG AGA AAG     288
Ala Arg Val Arg Val Trp Phe Lys Asn Arg Arg Ala Lys Trp Arg Lys
                85                  90                  95

AGG GAG CGC AAC CAG CAG GCC GAG CTA TGC AAG AAT GGC TTC GGG CCG     336
Arg Glu Arg Asn Gln Gln Ala Glu Leu Cys Lys Asn Gly Phe Gly Pro
            100                 105                 110

CAG TTC AAT GGG CTC ATG CAG CCC TAC GAC GAC ATG TAC CCA GGC TAT     384
Gln Phe Asn Gly Leu Met Gln Pro Tyr Asp Asp Met Tyr Pro Gly Tyr
        115                 120                 125

TCC TAC AAC AAC TGG GCC GCC AAG GGC CTT ACA TCC GCC TCC CTA TCC     432
Ser Tyr Asn Asn Trp Ala Ala Lys Gly Leu Thr Ser Ala Ser Leu Ser
    130                 135                 140

ACC AAG AGC TTC CCC TTC TTC AAC TCT ATG AAC GTC AAC CCC CTG TCA     480
Thr Lys Ser Phe Pro Phe Phe Asn Ser Met Asn Val Asn Pro Leu Ser
145                 150                 155                 160

TCA CAG AGC ATG TTT TCC CCA CCC AAC TCT ATC TCG TCC ATG AGC ATG     528
Ser Gln Ser Met Phe Ser Pro Pro Asn Ser Ile Ser Ser Met Ser Met
                165                 170                 175

TCG TCC AGC ATG GTG CCC TCA GCA GTG ACA GGC GTC CCG GGC TCC AGT     576
Ser Ser Ser Met Val Pro Ser Ala Val Thr Gly Val Pro Gly Ser Ser
            180                 185                 190

CTC AAC AGC CTG AAT AAC TTG AAC AAC CTG AGT AGC CCG TCG CTG AAT     624
Leu Asn Ser Leu Asn Asn Leu Asn Asn Leu Ser Ser Pro Ser Leu Asn
        195                 200                 205

TCC GCG GTG CCG ACG CCT GCC TGT CCT TAC GCG CCG CCG ACT CCT CCG     672
Ser Ala Val Pro Thr Pro Ala Cys Pro Tyr Ala Pro Pro Thr Pro Pro
    210                 215                 220

TAT GTT TAT AGG GAC ACG TGT AAC TCG AGC CTG GCC AGC CTG AGA CTG     720
Tyr Val Tyr Arg Asp Thr Cys Asn Ser Ser Leu Ala Ser Leu Arg Leu
225                 230                 235                 240
```

```
AAA GCA AAG CAG CAC TCC AGC TTC GGC TAC GCC AGC GTG CAG AAA CCG       768
Lys Ala Lys Gln His Ser Ser Phe Gly Tyr Ala Ser Val Gln Lys Pro
                245                 250                 255

GCC TCC AAC CTG AGT GCT TGC CAG TAT GCA GTG GAC CGG CCC GTG T         814
Ala Ser Asn Leu Ser Ala Cys Gln Tyr Ala Val Asp Arg Pro Val
            260                 265                 270

GA                                                                    816
```

(2) INFORMATION FOR SEQ ID NO:127:

(i) SEQUENCE CHARACTERISTICS:
        (A) LENGTH: 1929 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:127:

```
CGAGAAAGCT GGAGAGGAGC AGAAAGAAAC TGCCAGTGGC GGCTAGATTT CGGAGGCCCC      60

AGTGCACCCG TGGACTCCTT CGGAACTTGG CACCCTCAGG AGCCCTGCAG TCCTCTCAGG     120

CCCGGCTTTC GGGCGCTTGC CGTGCAGCCG GAGGCTCGGC TCGCTGGAAA TCGCCCCGGG     180

AAGCAGTGGG ACGGGAGAC AGCAGCTCTC TCCCGGTAGC CGGTAAGTGG AGGCGCTTCT      240

TACAGCCTTC CTTTCTTCTG TTTTGCAGAT AACGGGAAA TGGAGACCAA CTGCCGCAAA      300

CTGGTGTCGG CGTGTCTGCA ATTAGGTAAG AACCCCCTTC TCCTGCCCGG GTCATCGGAC     360

TGTGTTTCAG TTTTCAGAGA AAGATAAAAG CCAGCAGGGG AAGAATGAGG ACGTGGGCGC     420

CGAGGACCCG TCTAAGAAGA AGCGGCAAAG GCGGCAGCGG ACTCACTTTA CCAGCCAGCA     480

GCTCCAGCAG CTGGAGGCCA CTTTCCAGAG GAACCGCTAC CCGGACATGT CCCCACGCGA     540

AGAAATCGCT GTGTGGACCA ACCTTACGGA AGCCCGAGTC CGGGTGAGCC AGCACGGAGT     600

CTGGGAGGCT GTTTGCTCCC TTGCCCCAAC CGCCCCCAGG TTTGGTTCAA GAATCGTCGG     660

GCCAAATGGA GAAAGAGGGA GCGCAACCAG CAGGCCGAGC TATGCAAGAA TGGCTTCGGG     720

CCGCAGTTCA ATGGGCTCAT GCAGCCCTAC GACGACATGT ACCCAGGCTA TTCCTACAAC     780

AACTGGGCCG CCAAGGGCCT TACATCCGCC TCCCTATCCA CCAAGAGCTT CCCCTTCTTC     840

AACTCTATGA ACGTCAACCC CCTGTCATCA CAGAGCATGT TTTCCCCACC CAACTCTATC     900

TCGTCCATGA GCATGTCGTC CAGCATGGTG CCCTCAGCAG TGACAGGCGT CCCGGGCTCC     960

AGTCTCAACA GCCTGAATAA CTTGAACAAC CTGAGTAGCC CGTCGCTGAA TTCCGCGGTG    1020

CCGACGCCTG CCTGTCCTTA CGCGCCGCCG ACTCCTCCGT ATGTTTATAG GGACACGTGT    1080

AACTCGAGCC TGGCCAGCCT GAGACTGAAA GCAAAGCAGC ACTCCAGCTT CGGCTACGCC    1140

AGCGTGCAGA AACCGGCCTC CAACCTGAGT GCTTGCCAGT ATGCAGTGGA CCGGCCCGTG    1200

TGAGCCGCAC CCACAGCGCC GGGATCCTAG GACCTTGCCG GATGGGGCAA CTCCGCCCTT    1260

GAAAGACTGG GAATTATGCT AGAAGGTCGT GGGCACTAAA GAAAGGGAGA GAAAGAGAAG    1320

CTATATAGAG AAAAGGAAAC CACTGAATCA AGAGAGAGC TCCTTTGATT TCAAAGGGAT     1380

GTCCTCAGTG TCTGACATCT TTCACTACAA GTATTTCTAA CAGTTGCAAG GACACATACA    1440

CAAACAAATG TTTTGACTGG ATATGACATT TTAACATTAC TATAAGCTTG TTATTTTTTA    1500

AGTTTAGCAT TGTTAACATT TAAATGACTG AAAGGATGTA TATATATCGA AATGTCAAAT    1560

TAATTTTATA AAAGCAGTTG TTAGTAATAT CACAACAGTG TTTTTAAAGG TTAGGCTTTA    1620

AAATAAAGCA TGTTATACAG AAGCGATTAG GATTTTTCGC TTGCGAGCAA GGGAGTGTAT    1680
```

-continued

| ATACTAAATG CCACACTGTA TGTTTCTAAC ATATTATTAT TATTATAAAA AATGTGTGAA | 1740 |
| TATCAGTTTT AGAATAGTTT GTGTGGTGGA TGCAATGATG TTTCTGAAAC TGCTATGTAC | 1800 |
| AACCTACCCT GTGTATAACA TTTCGTACAA TATTATTGTT TTACTTTTCA GCAAATATGA | 1860 |
| AACAAATGTG TTTTATTTTC ATGGGAGTAA AATATACTGC ATACAAAAAA AAAAAAAAAA | 1920 |
| AAAAAAAAA | 1929 |

(2) INFORMATION FOR SEQ ID NO:128:

(i) SEQUENCE CHARACTERISTICS:
        (A) LENGTH: 1929 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:128:

| CGAGAAAGCT GGAGAGGAGC AGAAAGAAAC TGCCAGTGGC GGCTAGATTT CGGAGGCCCC | 60 |
| AGTGCACCCG TGGACTCCTT CGGAACTTGG CACCCTCAGG AGCCCTGCAG TCCTCTCAGG | 120 |
| CCCGGCTTTC GGGCGCTTGC CGTGCAGCCG GAGGCTCGGC TCGCTGGAAA TCGCCCCGGG | 180 |
| AAGCAGTGGG ACGCGGAGAC AGCAGCTCTC TCCCGGTAGC CGGTAAGTGG AGGCGCTTCT | 240 |
| TACAGCCTTC CTTTCTTCTG TTTTGCAGAT AACGGGAAA TGGAGACCAA CTGCCGCAAA | 300 |
| CTGGTGTCGG CGTGTCTGCA ATTAGGTAAG AACCCCTTC TCCTGCCCGG GTCATCGGAC | 360 |
| TGTGTTTCAG TTTTCAGAGA AAGATAAAAG CCAGCAGGGG AAGAATGAGG ACGTGGGCGC | 420 |
| CGAGGACCCG TCTAAGAAGA AGCGGCAAAG GCGGCAGCGG ACTCACTTTA CCAGCCAGCA | 480 |
| GCTCCAGCAG CTGGAGGCCA CTTTCCAGAG GAACCGCTAC CCGGACATGT CCACACGCGA | 540 |
| AGAAATCGCT GTGTGGACCA ACCTTACGGA AGCCCGAGTC CGGGTGACCC AGCACGGAGT | 600 |
| CTGGGAGGCT GTTTGCTCCC TTGCCCCAAC CGCCCCAGG TTTGGTTCAA GAATCGTCGG | 660 |
| GCCAAATGGA GAAAGAGGGA GCGCAACCAG CAGGCCGAGC TATGCAAGAA TGGCTTCGGG | 720 |
| CCGCAGTTCA ATGGGCTCAT GCAGCCCTAC GACGACATGT ACCCAGGCTA TTCCTACAAC | 780 |
| AACTGGGCCG CCAAGGGCCT TACATCCGCC TCCCTATCCA CCAAGAGCTT CCCCTTCTTC | 840 |
| AACTCTATGA ACGTCAACCC CCTGTCATCA CAGAGCATGT TTTCCCCACC CAACTCTATC | 900 |
| TCGTCCATGA GCATGTCGTC CAGCATGGTG CCCTCAGCAG TGACAGGCGT CCCGGGCTCC | 960 |
| AGTCTCAACA GCCTGAATAA CTTGAACAAC CTGAGTAGCC CGTCGCTGAA TTCCGCGGTG | 1020 |
| CCGACGCCTG CCTGTCCTTA CGCGCCGCCG ACTCCTCCGT ATGTTTATAG GGACACGTGT | 1080 |
| AACTCGAGCC TGGCCAGCCT GAGACTGAAA GCAAAGCAGC ACTCCAGCTT CGGCTACGCC | 1140 |
| AGCGTGCAGA AACCGGCCTC CAACCTGAGT GCTTGCCAGT ATGCAGTGGA CCGGCCCGTG | 1200 |
| TGAGCCGCAC CCACAGCGCC GGGATCCTAG GACCTTGCCG GATGGGGCAA CTCCGCCCTT | 1260 |
| GAAAGACTGG GAATTATGCT AGAAGGTCGT GGGCACTAAA GAAAGGGAGA GAAAGAGAAG | 1320 |
| CTATATAGAG AAAAGGAAAC CACTGAATCA AGAGAGAGC TCCTTTGATT TCAAAGGGAT | 1380 |
| GTCCTCAGTG TCTGACATCT TTCACTACAA GTATTTCTAA CAGTTGCAAG GACACATACA | 1440 |
| CAAACAAATG TTTTGACTGG ATATGACATT TTAACATTAC TATAAGCTTG TTATTTTTA | 1500 |
| AGTTTAGCAT TGTTAACATT TAAATGACTG AAAGGATGTA TATATATCGA AATGTCAAAT | 1560 |
| TAATTTTATA AAAGCAGTTG TTAGTAATAT CACAACAGTG TTTTTAAAGG TTAGGCTTTA | 1620 |
| AAATAAAGCA TGTTATACAG AAGCGATTAG GATTTTTCGC TTGCGAGCAA GGGAGTGTAT | 1680 |

-continued

| ATACTAAATG CCACACTGTA TGTTTCTAAC ATATTATTAT TATTATAAAA AATGTGTGAA | 1740 |
| TATCAGTTTT AGAATAGTTT GTGTGGTGGA TGCAATGATG TTTCTGAAAC TGCTATGTAC | 1800 |
| AACCTACCCT GTGTATAACA TTTCGTACAA TATTATTGTT TTACTTTTCA GCAAATATGA | 1860 |
| AACAAATGTG TTTTATTTTC ATGGGAGTAA AATATACTGC ATACAAAAAA AAAAAAAAAA | 1920 |
| AAAAAAAAA | 1929 |

(2) INFORMATION FOR SEQ ID NO:129:

(i) SEQUENCE CHARACTERISTICS:
        (A) LENGTH: 1929 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:129:

| CGAGAAAGCT GGAGAGGAGC AGAAAGAAAC TGCCAGTGGC GGCTAGATTT CGGAGGCCCC | 60 |
| AGTGCACCCG TGGACTCCTT CGGAACTTGG CACCCTCAGG AGCCCTGCAG TCCTCTCAGG | 120 |
| CCCGGCTTTC GGGCGCTTGC CGTGCAGCCG GAGGCTCGGC TCGCTGGAAA TCGCCCCGGG | 180 |
| AAGCAGTGGG ACGCGGAGAC AGCAGCTCTC TCCCGGTAGC CGGTAAGTGG AGGCGCTTCT | 240 |
| TACAGCCTTC CTTTCTTCTG TTTTGCAGAT AACGGGGAAA TGGAGACCAA CTGCCGCAAA | 300 |
| CTGGTGTCGG CGTGTCTGCA ATTAGGTAAG AACCCCCTTC TCCTGCCCGG GTCATCGGAC | 360 |
| TGTGTTTCAG TTTTCAGAGA AAGATAAAAG CCAGCAGGGG AAGAATGAGG ACGTGGGCGC | 420 |
| CGAGGACCCG TCTAAGAAGA AGCGGCAAAG GCGGCAGCCG ACTCACTTTA CCAGCCAGCA | 480 |
| GCTCCAGCAG CTGGAGGCCA CTTTCCAGAG GAACCGCTAC CCGGACATGT CCACACGCGA | 540 |
| AGAAATCGCT GTGTGGACCA ACCTTACGGA AGCCCGAGTC CGGGTGAGCC AGCACGGAGT | 600 |
| CTGGGAGGCT GTTTGCTCCC TTGCCCCAGC CGCCCCCAGG TTTGGTTCAA GAATCGTCGG | 660 |
| GCCAAATGGA GAAAGAGGGA GCGCAACCAG CAGGCCGAGC TATGCAAGAA TGGCTTCGGG | 720 |
| CCGCAGTTCA ATGGGCTCAT GCAGCCCTAC GACGACATGT ACCCAGGCTA TTCCTACAAC | 780 |
| AACTGGGCCG CCAAGGGCCT TACATCCGCC TCCCTATCCA CCAAGAGCTT CCCCTTCTTC | 840 |
| AACTCTATGA ACGTCAACCC CCTGTCATCA CAGAGCATGT TTTCCCCACC CAACTCTATC | 900 |
| TCGTCCATGA GCATGTCGTC CAGCATGGTG CCCTCAGCAG TGACAGGCGT CCCGGGCTCC | 960 |
| AGTCTCAACA GCCTGAATAA CTTGAACAAC CTGAGTAGCC CGTCGCTGAA TTCCGCGGTG | 1020 |
| CCGACGCCTG CCTGTCCTTA CGCGCCGCCG ACTCCTCCGT ATGTTTATAG GGACACGTGT | 1080 |
| AACTCGAGCC TGGCCAGCCT GAGACTGAAA GCAAAGCAGC ACTCCAGCTT CGGCTACGCC | 1140 |
| AGCGTGCAGA AACCGGCCTC CAACCTGAGT GCTTGCCAGT ATGCAGTGGA CCGGCCCGTG | 1200 |
| TGAGCCGCAC CCACAGCGCC GGGATCCTAG GACCTTGCCG GATGGGGCAA CTCCGCCCTT | 1260 |
| GAAAGACTGG GAATTATGCT AGAAGGTCGT GGGCACTAAA GAAAGGGAGA GAAAGAGAAG | 1320 |
| CTATATAGAG AAAAGGAAAC CACTGAATCA AAGAGAGAGC TCCTTTGATT TCAAAGGGAT | 1380 |
| GTCCTCAGTG TCTGACATCT TTCACTACAA GTATTTCTAA CAGTTGCAAG GACACATACA | 1440 |
| CAAACAAATG TTTTGACTGG ATATGACATT TTAACATTAC TATAAGCTTG TTATTTTTA | 1500 |
| AGTTTAGCAT TGTTAACATT TAAATGACTG AAAGGATGTA TATATATCGA AATGTCAAAT | 1560 |
| TAATTTTATA AAAGCAGTTG TTAGTAATAT CACAACAGTG TTTTTAAAGG TTAGGCTTTA | 1620 |
| AAATAAAGCA TGTTATACAG AAGCGATTAG GATTTTTCGC TTGCGAGCAA GGGAGTGTAT | 1680 |

-continued

```
ATACTAAATG CCACACTGTA TGTTTCTAAC ATATTATTAT TATTATAAAA AATGTGTGAA      1740

TATCAGTTTT AGAATAGTTT GTGTGGTGGA TGCAATGATG TTTCTGAAAC TGCTATGTAC      1800

AACCTACCCT GTGTATAACA TTTCGTACAA TATTATTGTT TTACTTTTCA GCAAATATGA      1860

AACAAATGTG TTTTATTTTC ATGGGAGTAA AATATACTGC ATACAAAAAA AAAAAAAAAA      1920

AAAAAAAAA                                                              1929
```

(2) INFORMATION FOR SEQ ID NO:130:

(i) SEQUENCE CHARACTERISTICS:
        (A) LENGTH: 1775 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 234..1047

(xi) SEQUENCE DESCRIPTION: SEQ ID NO:130:

```
CGAGAAAGCT GGAGAGGAGC AGAAAGAAAC TGCCAGTGGC GGCTAGATTT CGGAGGCCCC       60

AGTGCACCCG TGGACTCCTT CGGAACTTGG CACCCTCAGG AGCCCTGCAG TCCTCTCAGG      120

CCCGGCTTTC GGGCGCTTGC CGTGCAGCCG GAGGCTCGGC TCGCTGGAAA TCGCCCCGGG      180

AAGCAGTGGG ACGCGGAGAC AGCAGCTCTC TCCCGGTAGC CGATAACGGG GAA ATG        236
                                                          Met
                                                            1

GAG ACC AAC TGC CGC AAA CTG GTG TCG GCG TGT CTG CAA TTA GAG AAA       284
Glu Thr Asn Cys Arg Lys Leu Val Ser Ala Cys Leu Gln Leu Glu Lys
         5                  10                  15

GAT AAA AGC CAG CAG GGG AAG AAT GAG GAC GTG GGC GCC GAG GAC CCG       332
Asp Lys Ser Gln Gln Gly Lys Asn Glu Asp Val Gly Ala Glu Asp Pro
     20                  25                  30

TCT AAG AAG AAG CGG CAA AGG CGG CAG CGG ACT CAC TTT ACC AGC CAG       380
Ser Lys Lys Lys Arg Gln Arg Arg Gln Arg Thr His Phe Thr Ser Gln
 35                  40                  45

CAG CTC CAG CAG CTG GAG GCC ACT TTC CAG AGG AAC CGC TAC CCG GAC       428
Gln Leu Gln Gln Leu Glu Ala Thr Phe Gln Arg Asn Arg Tyr Pro Asp
 50                  55                  60                  65

ATG TCC ACA CGC GAA GAA ATC GCT GTG TGG ACC AAC CTT ACG GAA GCC       476
Met Ser Thr Arg Glu Glu Ile Ala Val Trp Thr Asn Leu Thr Glu Ala
                 70                  75                  80

CGA GTC CGG GTT TGG TTC AAG AAT CGT CCG GCC AAA TGG AGA AAG AGG       524
Arg Val Arg Val Trp Phe Lys Asn Arg Pro Ala Lys Trp Arg Lys Arg
             85                  90                  95

GAG CGC AAC CAG CAG GCC GAG CTA TGC AAG AAT GGC TTC GGG CCG CAG       572
Glu Arg Asn Gln Gln Ala Glu Leu Cys Lys Asn Gly Phe Gly Pro Gln
         100                 105                 110

TTC AAT GGG CTC ATG CAG CCC TAC GAC GAC ATG TAC CCA GGC TAT TCC       620
Phe Asn Gly Leu Met Gln Pro Tyr Asp Asp Met Tyr Pro Gly Tyr Ser
     115                 120                 125

TAC AAC AAC TGG GCC GCC AAG GGC CTT ACA TCC GCC TCC CTA TCC ACC       668
Tyr Asn Asn Trp Ala Ala Lys Gly Leu Thr Ser Ala Ser Leu Ser Thr
130                 135                 140                 145

AAG AGC TTC CCC TTC TTC AAC TCT ATG AAC GTC AAC CCC CTG TCA TCA       716
Lys Ser Phe Pro Phe Phe Asn Ser Met Asn Val Asn Pro Leu Ser Ser
                 150                 155                 160

CAG AGC ATG TTT TCC CCA CCC AAC TCT ATC TCG TCC ATG AGC ATG TCG       764
Gln Ser Met Phe Ser Pro Pro Asn Ser Ile Ser Ser Met Ser Met Ser
```

```
                165                 170                 175
TCC AGC ATG GTG CCC TCA GCA GTG ACA GGC GTC CCG GGC TCC AGT CTC         812
Ser Ser Met Val Pro Ser Ala Val Thr Gly Val Pro Gly Ser Ser Leu
            180                 185                 190

AAC AGC CTG AAT AAC TTG AAC AAC CTG AGT AGC CCG TCG CTG AAT TCC         860
Asn Ser Leu Asn Asn Leu Asn Asn Leu Ser Ser Pro Ser Leu Asn Ser
    195                 200                 205

GCG GTG CCG ACG CCT GCC TGT CCT TAC GCG CCG CCG ACT CCT CCG TAT         908
Ala Val Pro Thr Pro Ala Cys Pro Tyr Ala Pro Pro Thr Pro Pro Tyr
210                 215                 220                 225

GTT TAT AGG GAC ACG TGT AAC TCG AGC CTG GCC AGC CTG AGA CTG AAA         956
Val Tyr Arg Asp Thr Cys Asn Ser Ser Leu Ala Ser Leu Arg Leu Lys
                230                 235                 240

GCA AAG CAG CAC TCC AGC TTC GGC TAC GCC AGC GTG CAG AAA CCG GCC        1004
Ala Lys Gln His Ser Ser Phe Gly Tyr Ala Ser Val Gln Lys Pro Ala
            245                 250                 255

TCC AAC CTG AGT GCT TGC CAG TAT GCA GTG GAC CGG CCC GTG T              1047
Ser Asn Leu Ser Ala Cys Gln Tyr Ala Val Asp Arg Pro Val
        260                 265                 270

GAGCCGCACC CACAGCGCCG GGATCCTAGG ACCTTGCCGG ATGGGCAAC TCCGCCCTTG        1107

AAAGACTGGG AATTATGCTA GAAGGTCGTG GGCACTAAAG AAAGGGAGAG AAAGAGAAGC       1167

TATATAGAGA AAAGGAAACC ACTGAATCAA AGAGAGAGCT CCTTTGATTT CAAAGGGATG      1227

TCCTCAGTGT CTGACATCTT TCACTACAAG TATTTCTAAC AGTTGCAAGG ACACATACAC      1287

AAACAAATGT TTTGACTGGA TATGACATTT TAACATTACT ATAAGCTTGT TATTTTTTAA      1347

GTTTAGCATT GTTAACATTT AAATGACTGA AAGGATGTAT ATATATCGAA ATGTCAAATT      1407

AATTTTATAA AAGCAGTTGT TAGTAATATC ACAACAGTGT TTTTAAAGGT TAGGCTTTAA      1467

AATAAAGCAT GTTATACAGA AGCGATTAGG ATTTTTCGCT TGCGAGCAAG GGAGTGTATA      1527

TACTAAATGC CACACTGTAT GTTTCTAACA TATTATTATT ATTATAAAAA ATGTGTGAAT      1587

ATCAGTTTTA GAATAGTTTG TGTGGTGGAT GCAATGATGT TTCTGAAACT GCTATGTACA     1647

ACCTACCCTG TGTATAACAT TTCGTACAAT ATTATTGTTT TACTTTTCAG CAAATATGAA     1707

ACAAATGTGT TTTATTTTCA TGGGAGTAAA ATATACTGCA TACAAAAAAA AAAAAAAAA      1767

AAAAAAA                                                                1775

(2) INFORMATION FOR SEQ ID NO:131:

(i) SEQUENCE CHARACTERISTICS:
        (A) LENGTH: 271 amino acids
        (B) TYPE: amino acid
        (D) TOPOLOGY: linear (ii) MOLECULE TYPE: protein (xi) SEQUENCE DESCRIPTION: SEQ ID NO:131:

Met Glu Thr Asn Cys Arg Lys Leu Val Ser Ala Cys Leu Gln Leu Glu
1               5                   10                  15

Lys Asp Lys Ser Gln Gln Gly Lys Asn Glu Asp Val Gly Ala Glu Asp
            20                  25                  30

Pro Ser Lys Lys Lys Arg Gln Arg Gln Arg Thr His Phe Thr Ser
        35                  40                  45

Gln Gln Leu Gln Gln Leu Glu Ala Thr Phe Gln Arg Asn Arg Tyr Pro
    50                  55                  60

Asp Met Ser Thr Arg Glu Glu Ile Ala Val Trp Thr Asn Leu Thr Glu
65                  70                  75                  80
```

```
Ala Arg Val Arg Val Trp Phe Lys Asn Arg Pro Ala Lys Trp Arg Lys
            85                  90                  95

Arg Glu Arg Asn Gln Gln Ala Glu Leu Cys Lys Asn Gly Phe Gly Pro
            100                 105                 110

Gln Phe Asn Gly Leu Met Gln Pro Tyr Asp Asp Met Tyr Pro Gly Tyr
            115                 120                 125

Ser Tyr Asn Asn Trp Ala Ala Lys Gly Leu Thr Ser Ala Ser Leu Ser
    130                 135                 140

Thr Lys Ser Phe Pro Phe Phe Asn Ser Met Asn Val Asn Pro Leu Ser
145                 150                 155                 160

Ser Gln Ser Met Phe Ser Pro Pro Asn Ser Ile Ser Ser Met Ser Met
                165                 170                 175

Ser Ser Ser Met Val Pro Ser Ala Val Thr Gly Val Pro Gly Ser Ser
                180                 185                 190

Leu Asn Ser Leu Asn Asn Leu Asn Asn Leu Ser Ser Pro Ser Leu Asn
            195                 200                 205

Ser Ala Val Pro Thr Pro Ala Cys Pro Tyr Ala Pro Pro Thr Pro Pro
    210                 215                 220

Tyr Val Tyr Arg Asp Thr Cys Asn Ser Ser Leu Ala Ser Leu Arg Leu
225                 230                 235                 240

Lys Ala Lys Gln His Ser Ser Phe Gly Tyr Ala Ser Val Gln Lys Pro
                245                 250                 255

Ala Ser Asn Leu Ser Ala Cys Gln Tyr Ala Val Asp Arg Pro Val
            260                 265                 270

(2) INFORMATION FOR SEQ ID NO:132:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..814

(xi) SEQUENCE DESCRIPTION: SEQ ID NO:132:

ATG GAG ACC AAC TGC CGC AAA CTG GTG TCG GCG TGT CTG CAA TTA GAG        48
Met Glu Thr Asn Cys Arg Lys Leu Val Ser Ala Cys Leu Gln Leu Glu
 1               5                  10                  15

AAA GAT AAA AGC CAG CAG GGG AAG AAT GAG GAC GTG GGC GCC GAG GAC        96
Lys Asp Lys Ser Gln Gln Gly Lys Asn Glu Asp Val Gly Ala Glu Asp
            20                  25                  30

CCG TCT AAG AAG AAG CGG CAA AGG CGG CAG CGG ACT CAC TTT ACC AGC       144
Pro Ser Lys Lys Lys Arg Gln Arg Arg Gln Arg Thr His Phe Thr Ser
        35                  40                  45

CAG CAG CTC CAG CAG CTG GAG GCC ACT TTC CAG AGG AAC CGC TAC CCG       192
Gln Gln Leu Gln Gln Leu Glu Ala Thr Phe Gln Arg Asn Arg Tyr Pro
    50                  55                  60

GAC ATG TCC ACA CGC GAA GAA ATC GCT GTG TGG ACC AAC CTT ACG GAA       240
Asp Met Ser Thr Arg Glu Glu Ile Ala Val Trp Thr Asn Leu Thr Glu
65                  70                  75                  80

GCC CGA GTC CGG GTT TGG TTC AAG AAT CGT CCG GCC AAA TGG AGA AAG       288
Ala Arg Val Arg Val Trp Phe Lys Asn Arg Pro Ala Lys Trp Arg Lys
                85                  90                  95

AGG GAG CGC AAC CAG CAG GCC GAG CTA TGC AAG AAT GGC TTC GGG CCG       336
Arg Glu Arg Asn Gln Gln Ala Glu Leu Cys Lys Asn Gly Phe Gly Pro
```

```
                    100              105                  110
CAG TTC AAT GGG CTC ATG CAG CCC TAC GAC GAC ATG TAC CCA GGC TAT         384
Gln Phe Asn Gly Leu Met Gln Pro Tyr Asp Asp Met Tyr Pro Gly Tyr
            115                 120                 125

TCC TAC AAC AAC TGG GCC GCC AAG GGC CTT ACA TCC GCC TCC CTA TCC         432
Ser Tyr Asn Asn Trp Ala Ala Lys Gly Leu Thr Ser Ala Ser Leu Ser
130                 135                 140

ACC AAG AGC TTC CCC TTC TTC AAC TCT ATG AAC GTC AAC CCC CTG TCA         480
Thr Lys Ser Phe Pro Phe Phe Asn Ser Met Asn Val Asn Pro Leu Ser
145                 150                 155                 160

TCA CAG AGC ATG TTT TCC CCA CCC AAC TCT ATC TCG TCC ATG AGC ATG         528
Ser Gln Ser Met Phe Ser Pro Pro Asn Ser Ile Ser Ser Met Ser Met
                165                 170                 175

TCG TCC AGC ATG GTG CCC TCA GCA GTG ACA GGC GTC CCG GGC TCC AGT         576
Ser Ser Ser Met Val Pro Ser Ala Val Thr Gly Val Pro Gly Ser Ser
            180                 185                 190

CTC AAC AGC CTG AAT AAC TTG AAC AAC CTG AGT AGC CCG TCG CTG AAT         624
Leu Asn Ser Leu Asn Asn Leu Asn Asn Leu Ser Ser Pro Ser Leu Asn
            195                 200                 205

TCC GCG GTG CCG ACG CCT GCC TGT CCT TAC GCG CCG CCG ACT CCT CCG         672
Ser Ala Val Pro Thr Pro Ala Cys Pro Tyr Ala Pro Pro Thr Pro Pro
210                 215                 220

TAT GTT TAT AGG GAC ACG TGT AAC TCG AGC CTG GCC AGC CTG AGA CTG         720
Tyr Val Tyr Arg Asp Thr Cys Asn Ser Ser Leu Ala Ser Leu Arg Leu
225                 230                 235                 240

AAA GCA AAG CAG CAC TCC AGC TTC GGC TAC GCC AGC GTG CAG AAA CCG         768
Lys Ala Lys Gln His Ser Ser Phe Gly Tyr Ala Ser Val Gln Lys Pro
                245                 250                 255

GCC TCC AAC CTG AGT GCT TGC CAG TAT GCA GTG GAC CGG CCC GTG T           814
Ala Ser Asn Leu Ser Ala Cys Gln Tyr Ala Val Asp Arg Pro Val
            260                 265                 270

GA                                                                      816

(2) INFORMATION FOR SEQ ID NO:133:

(i) SEQUENCE CHARACTERISTICS:
        (A) LENGTH: 1929 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:133:

CGAGAAAGCT GGAGAGGAGC AGAAAGAAAC TGCCAGTGGC GGCTAGATTT CGGAGGCCCC         60

AGTGCACCCG TGGACTCCTT CGGAACTTGG CACCCTCAGG AGCCCTGCAG TCCTCTCAGG        120

CCCGGCTTTC GGGCGCTTGC CGTGCAGCCG GAGGCTCGGC TCGCTGGAAA TCGCCCCGGG        180

AAGCAGTGGG ACGCGGAGAC AGCAGCTCTC TCCCGGTAGC CGGTAAGTGG AGGCGCTTCT        240

TACAGCCTTC CTTTCTTCTG TTTTGCAGAT AACGGGAAA TGGAGACCAA CTGCCGCAAA        300

CTGGTGTCGG CGTGTCTGCA ATTAGGTAAG AACCCCCTTC TCCTGCCCGG GTCATCGGAC        360

TGTGTTTCAG TTTTCAGAGA AAGATAAAAG CCAGCAGGGG AAGAATGAGG ACGTGGGCGC        420

CGAGGACCCG TCTAAGAAGA AGCGGCAAAG GCGGCAGCGG ACTCACTTTA CCAGCCAGCA        480

GCTCCAGCAG CTGGAGGCCA CTTTCCAGAG GAACCGCTAC CCGGACATGT CCACACGCGA        540

AGAAATCGCT GTGTGGACCA ACCTTACGGA AGCCCGAGTC CGGGTGAGCC AGCACGGAGT        600

CTGGGAGGCT GTTTGCTCCC TTGCCCCAAC CGCCCCCAGG TTTGGTTCAA GAATCGTCCG        660
```

```
GCCAAATGGA GAAAGAGGGA GCGCAACCAG CAGGCCGAGC TATGCAAGAA TGGCTTCGGG     720

CCGCAGTTCA ATGGGCTCAT GCAGCCCTAC GACGACATGT ACCCAGGCTA TTCCTACAAC     780

AACTGGGCCG CCAAGGGCCT TACATCCGCC TCCCTATCCA CCAAGAGCTT CCCCTTCTTC     840

AACTCTATGA ACGTCAACCC CCTGTCATCA CAGAGCATGT TTTCCCCACC CAACTCTATC     900

TCGTCCATGA GCATGTCGTC CAGCATGGTG CCCTCAGCAG TGACAGGCGT CCCGGGCTCC     960

AGTCTCAACA GCCTGAATAA CTTGAACAAC CTGAGTAGCC CGTCGCTGAA TTCCGCGGTG    1020

CCGACGCCTG CCTGTCCTTA CGCGCCGCCG ACTCCTCCGT ATGTTTATAG GGACACGTGT    1080

AACTCGAGCC TGGCCAGCCT GAGACTGAAA GCAAAGCAGC ACTCCAGCTT CGGCTACGCC    1140

AGCGTGCAGA AACCGGCCTC CAACCTGAGT GCTTGCCAGT ATGCAGTGGA CCGGCCCGTG    1200

TGAGCCGCAC CCACAGCGCC GGGATCCTAG GACCTTGCCG GATGGGCAA CTCCGCCCTT    1260

GAAAGACTGG GAATTATGCT AGAAGGTCGT GGGCACTAAA GAAAGGGAGA GAAAGAGAAG    1320

CTATATAGAG AAAAGGAAAC CACTGAATCA AGAGAGAGC TCCTTTGATT TCAAAGGGAT    1380

GTCCTCAGTG TCTGACATCT TTCACTACAA GTATTTCTAA CAGTTGCAAG ACACATACA    1440

CAAACAAATG TTTTGACTGG ATATGACATT TTAACATTAC TATAAGCTTG TTATTTTTA    1500

AGTTTAGCAT TGTTAACATT TAAATGACTG AAAGGATGTA TATATATCGA AATGTCAAAT    1560

TAATTTTATA AAAGCAGTTG TTAGTAATAT CACAACAGTG TTTTTAAAGG TTAGGCTTTA    1620

AAATAAAGCA TGTTATACAG AAGCGATTAG GATTTTTCGC TTGCGAGCAA GGGAGTGTAT    1680

ATACTAAATG CCACACTGTA TGTTTCTAAC ATATTATTAT TATTATAAAA AATGTGTGAA    1740

TATCAGTTTT AGAATAGTTT GTGTGGTGGA TGCAATGATG TTTCTGAAAC TGCTATGTAC    1800

AACCTACCCT GTGTATAACA TTTCGTACAA TATTATTGTT TTACTTTTCA GCAAATATGA    1860

AACAAATGTG TTTTATTTTC ATGGGAGTAA AATATACTGC ATACAAAAAA AAAAAAAAA    1920

AAAAAAAA                                                            1929

(2) INFORMATION FOR SEQ ID NO:134:

(i) SEQUENCE CHARACTERISTICS:
        (A) LENGTH: 1775 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 234..629

(xi) SEQUENCE DESCRIPTION: SEQ ID NO:134:

CGAGAAAGCT GGAGAGGAGC AGAAAGAAAC TGCCAGTGGC GGCTAGATTT CGGAGGCCCC      60

AGTGCACCCG TGGACTCCTT CGGAACTTGG CACCCTCAGG AGCCCTGCAG TCCTCTCAGG     120

CCCGGCTTTC GGGCGCTTGC CGTGCAGCCG GAGGCTCGGC TCGCTGGAAA TCGCCCCGGG    180

AAGCAGTGGG ACGCGGAGAC AGCAGCTCTC TCCCGGTAGC CGATAACGGG GAA ATG        236
                                                          Met
                                                          1

GAG ACC AAC TGC CGC AAA CTG GTG TCG GCG TGT CTG CAA TTA GAG AAA       284
Glu Thr Asn Cys Arg Lys Leu Val Ser Ala Cys Leu Gln Leu Glu Lys
         5                  10                  15

GAT AAA AGC CAG CAG GGG AAG AAT GAG GAC GTG GGC GCC GAG GAC CCG       332
Asp Lys Ser Gln Gln Gly Lys Asn Glu Asp Val Gly Ala Glu Asp Pro
    20                  25                  30
```

```
TCT AAG AAG AAG CGG CAA AGG CGG CAG CGG ACT CAC TTT ACC AGC CAG      380
Ser Lys Lys Lys Arg Gln Arg Arg Gln Arg Thr His Phe Thr Ser Gln
    35                  40                  45

CAG CTC CAG CAG CTG GAG GCC ACT TTC CAG AGG AAC CGC TAC CCG GAC      428
Gln Leu Gln Gln Leu Glu Ala Thr Phe Gln Arg Asn Arg Tyr Pro Asp
 50                  55                  60                  65

ATG TCC ACA CGC GAA GAA ATC GCT GTG TGG ACC AAC CTT ACG GAA GCC      476
Met Ser Thr Arg Glu Glu Ile Ala Val Trp Thr Asn Leu Thr Glu Ala
                 70                  75                  80

CGA GTC CGG GTT TGG TTC AAG AAT CGT CGG GCC AAA TGG AGA AAG AGG      524
Arg Val Arg Val Trp Phe Lys Asn Arg Arg Ala Lys Trp Arg Lys Arg
                     85                  90                  95

GAG CGC AAC CAG CAG GCC GAG CTA TGC AAG AAT GGC TTC GGG CCG CAG      572
Glu Arg Asn Gln Gln Ala Glu Leu Cys Lys Asn Gly Phe Gly Pro Gln
                    100                 105                 110

TTC AAT GGG CTC ATG CAG CCC TAC GAC GAC ATG TAC CCA GGC TAT TCC      620
Phe Asn Gly Leu Met Gln Pro Tyr Asp Asp Met Tyr Pro Gly Tyr Ser
            115                 120                 125

TAC AAC AAC TGAGCCGCCA AGGGCTTAC ATCCGCCTCC CTATCCACCA               669
Tyr Asn Asn
130

AGAGCTTCCC CTTCTTCAAC TCTATGAACG TCAACCCCCT GTCATCACAG AGCATGTTTT    729
CCCCACCCAA CTCTATCTCG TCCATGAGCA TGTCGTCCAG CATGGTGCCC TCAGCAGTGA    789
CAGGCGTCCC GGGCTCCAGT CTCAACAGCC TGAATAACTT GAACAACCTG AGTAGCCCGT    849
CGCTGAATTC CGCGGTGCCG ACGCCTGCCT GTCCTTACGC GCCGCCGACT CCTCCGTATG    909
TTTATAGGGA CACGTGTAAC TCGAGCCTGG CCAGCCTGAG ACTGAAAGCA AAGCAGCACT    969
CCAGCTTCGG CTACGCCAGC GTGCAGAAAC CGGCCTCCAA CCTGAGTGCT TGCCAGTATG   1029
CAGTGGACCG GCCCGTGTGA GCCGCACCCA GCGCCGGG ATCCTAGGAC CTTGCCGGAT    1089
GGGGCAACTC CGCCCTTGAA AGACTGGAA TTATGCTAGA AGGTCGTGGG CACTAAAGAA    1149
AGGGAGAGAA AGAGAAGCTA TATAGAGAAA AGGAAACCAC TGAATCAAAG AGAGAGCTCC   1209
TTTGATTTCA AAGGGATGTC CTCAGTGTCT GACATCTTTC ACTACAAGTA TTTCTAACAG   1269
TTGCAAGGAC ACATACACAA ACAAATGTTT TGACTGGATA TGACATTTTA ACATTACTAT   1329
AAGCTTGTTA TTTTTTAAGT TTAGCATTGT TAACATTTAA ATGACTGAAA GGATGTATAT   1389
ATATCGAAAT GTCAAATTAA TTTTATAAAA GCAGTTGTTA GTAATATCAC AACAGTGTTT   1449
TTAAAGGTTA GGCTTTAAAA TAAAGCATGT TATACAGAAG CGATTAGGAT TTTTCGCTTG   1509
CGAGCAAGGG AGTGTATATA CTAAATGCCA CACTGTATGT TTCTAACATA TTATTATTAT   1569
TATAAAAAAT GTGTGAATAT CAGTTTTAGA ATAGTTTGTG TGGTGGATGC AATGATGTTT   1629
CTGAAACTGC TATGTACAAC CTACCCTGTG TATAACATTT CGTACAATAT TATTGTTTTA   1689
CTTTTCAGCA AATATGAAAC AAATGTGTTT TATTTTCATG GGAGTAAAAT ATACTGCATA   1749
CAAAAAAAAA AAAAAAAAAA AAAAA                                         1775
```

(2) INFORMATION FOR SEQ ID NO:135:

(i) SEQUENCE CHARACTERISTICS:
        (A) LENGTH: 132 amino acids
        (B) TYPE: amino acid
        (D) TOPOLOGY: linear (ii) MOLECULE TYPE: protein (xi) SEQUENCE DESCRIPTION: SEQ ID NO:135:

Met Glu Thr Asn Cys Arg Lys Leu Val Ser Ala Cys Leu Gln Leu Glu

```
              1               5                  10                 15
           Lys Asp Lys Ser Gln Gln Gly Lys Asn Glu Asp Val Gly Ala Glu Asp
                           20                  25                 30

Pro Ser Lys Lys Lys Arg Gln Arg Arg Gln Arg Thr His Phe Thr Ser
                       35                  40                  45

Gln Gln Leu Gln Gln Leu Glu Ala Thr Phe Gln Arg Asn Arg Tyr Pro
                   50                  55                  60

Asp Met Ser Thr Arg Glu Glu Ile Ala Val Trp Thr Asn Leu Thr Glu
           65                  70                  75                  80

Ala Arg Val Arg Val Trp Phe Lys Asn Arg Arg Ala Lys Trp Arg Lys
                           85                  90                  95

Arg Glu Arg Asn Gln Gln Ala Glu Leu Cys Lys Asn Gly Phe Gly Pro
                           100                 105                110

Gln Phe Asn Gly Leu Met Gln Pro Tyr Asp Asp Met Tyr Pro Gly Tyr
                       115                 120                 125

Ser Tyr Asn Asn
               130
```

(2) INFORMATION FOR SEQ ID NO:136:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..396

(xi) SEQUENCE DESCRIPTION: SEQ ID NO:136:

```
ATG GAG ACC AAC TGC CGC AAA CTG GTG TCG GCG TGT CTG CAA TTA GAG      48
Met Glu Thr Asn Cys Arg Lys Leu Val Ser Ala Cys Leu Gln Leu Glu
 1               5                  10                  15

AAA GAT AAA AGC CAG CAG GGG AAG AAT GAG GAC GTG GGC GCC GAG GAC      96
Lys Asp Lys Ser Gln Gln Gly Lys Asn Glu Asp Val Gly Ala Glu Asp
                20                  25                  30

CCG TCT AAG AAG AAG CGG CAA AGG CGG CAG CGG ACT CAC TTT ACC AGC     144
Pro Ser Lys Lys Lys Arg Gln Arg Arg Gln Arg Thr His Phe Thr Ser
            35                  40                  45

CAG CAG CTC CAG CAG CTG GAG GCC ACT TTC CAG AGG AAC CGC TAC CCG     192
Gln Gln Leu Gln Gln Leu Glu Ala Thr Phe Gln Arg Asn Arg Tyr Pro
        50                  55                  60

GAC ATG TCC ACA CGC GAA GAA ATC GCT GTG TGG ACC AAC CTT ACG GAA     240
Asp Met Ser Thr Arg Glu Glu Ile Ala Val Trp Thr Asn Leu Thr Glu
65                  70                  75                  80

GCC CGA GTC CGG GTT TGG TTC AAG AAT CGT CGG GCC AAA TGG AGA AAG     288
Ala Arg Val Arg Val Trp Phe Lys Asn Arg Arg Ala Lys Trp Arg Lys
                85                  90                  95

AGG GAG CGC AAC CAG CAG GCC GAG CTA TGC AAG AAT GGC TTC GGG CCG     336
Arg Glu Arg Asn Gln Gln Ala Glu Leu Cys Lys Asn Gly Phe Gly Pro
            100                 105                 110

CAG TTC AAT GGG CTC ATG CAG CCC TAC GAC GAC ATG TAC CCA GGC TAT     384
Gln Phe Asn Gly Leu Met Gln Pro Tyr Asp Asp Met Tyr Pro Gly Tyr
        115                 120                 125

TCC TAC AAC AAC TGA                                                 399
Ser Tyr Asn Asn
    130
```

(2) INFORMATION FOR SEQ ID NO:137:

(i) SEQUENCE CHARACTERISTICS:
        (A) LENGTH: 1929 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:137:

```
CGAGAAAGCT GGAGAGGAGC AGAAAGAAAC TGCCAGTGGC GGCTAGATTT CGGAGGCCCC      60
AGTGCACCCG TGGACTCCTT CGGAACTTGG CACCCTCAGG AGCCCTGCAG TCCTCTCAGG     120
CCCGGCTTTC GGGCGCTTGC CGTGCAGCCG GAGGCTCGGC TCGCTGGAAA TCGCCCCGGG     180
AAGCAGTGGG ACGCGGAGAC AGCAGCTCTC TCCCGGTAGC CGGTAAGTGG AGGCGCTTCT     240
TACAGCCTTC CTTTCTTCTG TTTTGCAGAT AACGGGAAA TGGAGACCAA CTGCCGCAAA      300
CTGGTGTCGG CGTGTCTGCA ATTAGGTAAG AACCCCCTTC TCCTGCCCGG GTCATCGGAC     360
TGTGTTTCAG TTTTCAGAGA AAGATAAAAG CCAGCAGGGG AAGAATGAGG ACGTGGGCGC     420
CGAGGACCCG TCTAAGAAGA AGCGGCAAAG GCGGCAGCGG ACTCACTTTA CCAGCCAGCA     480
GCTCCAGCAG CTGGAGGCCA CTTTCCAGAG GAACCGCTAC CCGGACATGT CCACACGCGA     540
AGAAATCGCT GTGTGGACCA ACCTTACGGA AGCCCGAGTC CGGGTGAGCC AGCACGGAGT     600
CTGGGAGGCT GTTTGCTCCC TTGCCCCAAC CGCCCCCAGG TTTGGTTCAA GAATCGTCGG     660
GCCAAATGGA GAAAGAGGGA GCGCAACCAG CAGGCCGAGC TATGCAAGAA TGGCTTCGGG     720
CCGCAGTTCA ATGGGCTCAT GCAGCCCTAC GACGACATGT ACCCAGGCTA TTCCTACAAC     780
AACTGAGCCG CCAAGGGCCT TACATCCGCC TCCCTATCCA CCAAGAGCTT CCCCTTCTTC     840
AACTCTATGA ACGTCAACCC CCTGTCATCA CAGAGCATGT TTTCCCCACC CAACTCTATC     900
TCGTCCATGA GCATGTCGTC CAGCATGGTG CCCTCAGCAG TGACAGGCGT CCCGGGCTCC     960
AGTCTCAACA GCCTGAATAA CTTGAACAAC CTGAGTAGCC CGTCGCTGAA TTCCGCGGTG    1020
CCGACGCCTG CCTGTCCTTA CGCGCCGCCG ACTCCTCCGT ATGTTTATAG GGACACGTGT    1080
AACTCGAGCC TGGCCAGCCT GAGACTGAAA GCAAAGCAGC ACTCCAGCTT CGGCTACGCC    1140
AGCGTGCAGA AACCGGCCTC CAACCTGAGT GCTTGCCAGT ATGCAGTGGA CCGGCCCGTG    1200
TGAGCCGCAC CCACAGCGCC GGGATCCTAG GACCTTGCCG GATGGGGCAA CTCCGCCCTT    1260
GAAAGACTGG GAATTATGCT AGAAGGTCGT GGGCACTAAA GAAAGGGAGA GAAAGAGAAG    1320
CTATATAGAG AAAAGGAAAC CACTGAATCA AAGAGAGAGC TCCTTTGATT TCAAAGGGAT    1380
GTCCTCAGTG TCTGACATCT TTCACTACAA GTATTTCTAA CAGTTGCAAG GACACATACA    1440
CAAACAAATG TTTTGACTGG ATATGACATT TTAACATTAC TATAAGCTTG TTATTTTTTA    1500
AGTTTAGCAT TGTTAACATT TAAATGACTG AAAGGATGTA TATATATCGA AATGTCAAAT    1560
TAATTTTATA AAAGCAGTTG TTAGTAATAT CACAACAGTG TTTTTAAAGG TTAGGCTTTA    1620
AAATAAAGCA TGTTATACAG AAGCGATTAG GATTTTTCGC TTGCGAGCAA GGGAGTGTAT    1680
ATACTAAATG CCACACTGTA TGTTTCTAAC ATATTATTAT TATTATAAAA AATGTGTGAA    1740
TATCAGTTTT AGAATAGTTT GTGTGGTGGA TGCAATGATG TTTCTGAAAC TGCTATGTAC    1800
AACCTACCCT GTGTATAACA TTTCGTACAA TATTATTGTT TTACTTTTCA GCAAATATGA    1860
AACAAATGTG TTTTATTTTC ATGGGAGTAA AATATACTGC ATACAAAAAA AAAAAAAAA     1920
AAAAAAAA                                                             1929
```

```
(2) INFORMATION FOR SEQ ID NO:138:

(i) SEQUENCE CHARACTERISTICS:
        (A) LENGTH: 484 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 281..484

(xi) SEQUENCE DESCRIPTION: SEQ ID NO:138:

CACCGAGCGG CTCCCTAAAG AGGCTCGCAG CGGTTCCCTC CTGCCCACGT CCCCACGTCT        60

GCGTTGGCCC CCCTGCCTTT CGGCTGCCGA ACTCTTTTTG GCTGGAGTCT GAAGCTAGAG       120

GAGACAGGGC TGGAGGATTC GGCAGTTTGC GTTCCCTGGC TCTTTCAAGT CTCGGCTAAC       180

ACGGGGACAC TTGGCGCCTA GAGCGCTACC GAGAACCGGC GGCCACCGGG GCTCCACTGG       240

CGGTAGCCCT GGACTCATAG GGCTCCGCAC TCCCTCGTCC ATG AAC TGC ATG AAA        295
                                              Met Asn Cys Met Lys
                                                1               5

GGC CCG CTG CCC TTG GAG CAC CGA GCA GCC GGG ACT AAG CTG TCG GCC        343
Gly Pro Leu Pro Leu Glu His Arg Ala Ala Gly Thr Lys Leu Ser Ala
             10                  15                  20

GCC TCC TCA CCC TTC TGT CAC CAT CCC CAG GCG TTA GCC ATG GCT TCG        391
Ala Ser Ser Pro Phe Cys His His Pro Gln Ala Leu Ala Met Ala Ser
         25                  30                  35

GTC CTA GCT CCT GGC CAG CCC CGC TCC TTG GAC TCC TCC AAA CAT AGA        439
Val Leu Ala Pro Gly Gln Pro Arg Ser Leu Asp Ser Ser Lys His Arg
     40                  45                  50

CTG GAG GTG CAT ACA ATC TCC GAT ACT TCC AGC CCT GAA GTC GCA            484
Leu Glu Val His Thr Ile Ser Asp Thr Ser Ser Pro Glu Val Ala
 55                  60                  65

(2) INFORMATION FOR SEQ ID NO:139:

(i) SEQUENCE CHARACTERISTICS:
        (A) LENGTH: 68 amino acids
        (B) TYPE: amino acid
        (D) TOPOLOGY: linear (ii) MOLECULE TYPE: protein (xi) SEQUENCE DESCRIPTION: SEQ ID NO:139:

Met Asn Cys Met Lys Gly Pro Leu Pro Leu Glu His Arg Ala Ala Gly
 1               5                  10                  15

Thr Lys Leu Ser Ala Ala Ser Ser Pro Phe Cys His His Pro Gln Ala
             20                  25                  30

Leu Ala Met Ala Ser Val Leu Ala Pro Gly Gln Pro Arg Ser Leu Asp
         35                  40                  45

Ser Ser Lys His Arg Leu Glu Val His Thr Ile Ser Asp Thr Ser Ser
     50                  55                  60

Pro Glu Val Ala
 65
```

RGS COMPOSITIONS AND THERAPEUTIC AND DIAGNOSTIC USES THEREFOR

BACKGROUND OF THE INVENTION

Rieger syndrome (RS) is an autosomal dominant disorder of morphogenesis characterized by abnormalities of the anterior segment of the eye and dental hypoplasia. Other systemic anomalies have been reported in association with the syndrome, the most common of which are mild craniofacial dysmorphism, including maxillary hypoplasia and failure of involution of the periumbilical skin and omphalocele. Gastrointestinal defects reported include Meckels diverticulum (Krespi, Y. P. and D. Pertsemlidis (1979) *Am. J. Gastroenter.* 71:608–610) colon atresia (Rogers, R. C. (1988) *Proc. Greenwood. Genet. Center* 7:9–13) and anal stenosis (Crawford, R. D. (1967) Brit. J. Ophthalmol. 51:438–440) The ocular features can include a prominent, anteriorly displaced Schwalbe line, iris processes which insert into the Schwalbe line, hypoplasia of the anterior iris stroma or corectopiea and pseudopolycoria. Roughly one-half of the patients will develop glaucoma, usually by young adulthood. The dental features associated with the condition include oligodontia and microdontia.

There is general agreement that patients with both the ocular features and systemic abnormalities (dental, umbilical, craniofacial) should be designated Rieger syndrome. The nomenclature of patients with only the ocular features, however, is confusing and disputed. For example, the condition of only ocular abnormalities is sometimes referred to as Rieger syndrome and other times referred to as Axenfeld-Rieger anomaly.

The underlying genetic defect and the chromosomal localization of RS is uncertain. Cases with Axenfeld-Rieger anomaly have been reported with various aberrations of chromosomes 4, 6, 10, 13, 16, and 22 (Wilcox, L. M. et al., (1978) *Am. J. Ophthalmol.* 86:834–839; Tabbara, K. F. et al. (1973) *Canad. J. Ophthal.* 8:488–491; Herve, J. et al. 1984) *Ann. Pediatr.* 31:77–80; Stathacopoulas, R. A. et al. (1987) *J. Ped. Ophthalmol. Strabismus* 24:198–203; Akazawa, K. et al. (1981) *J. Ophthalmol.* 105:323; Furguson, J. G. and E. L. Hicks (1987) *Arch. Ophthal.* 105:323; Heinemann, M. et al. (1979) *Br. J. Ophthalmol.* 63:40–44). Four cases of fully developed RS, including the dental and umbilical anomalies, have been associated with deletions in the region of chromosome 4q23-26. One case of a deletion in the region of 4q26 which did not have RS has also been reported. These cases indicate that a gene for RS lies in the region of 4q25.

In RS, a high risk of developing increased intraocular pressures and subsequent glaucomatous damage necessitates vigorous screening procedures beginning in infancy. Current screening for the ocular abnormalities of RS requires slit lamp examination, tonometry, gonioscopy and a dilated examination of the optic nerve head.

SUMMARY OF THE INVENTION

The present invention is based on the discovery of novel molecules, referred to herein as RIEG nucleic acids and RIEG or "Solurshin" polypeptide molecules. The human RIEG gene, which is approximately 18 kb, consists of four exons, 222, 49, 206 and 1306 nucleotides in length. The ATG initiation codon is located in the second exon and the homeobox region in the third and fourth exons. Translation of the open reading frame yields a protein of about 271 amino acids.

The gene is expressed in oral epithelium, the umbilicus, and periocular mesoderm, consistent with the phenotypic abnormalities seen in Rieger syndrome patients. In addition, the gene is expressed in Rathke's pouch and the vitelline artery.

In one aspect, the invention features isolated vertebrate RIEG nucleic acid molecules. The disclosed molecules can be non-coding, (e.g. probe, antisense or ribozyme molecules) or can encode a functional RIEG polypeptide (e.g. a polypeptide which specifically modulates, e.g., by acting as either an agonist or antagonist, at least one bioactivity of the human RIEG polypeptide). In one embodiment, the nucleic acids of the present invention can hybridize to a vertebrate RIEG gene or to the complement of a vertebrate RIEG gene. In a further embodiment, the claimed nucleic acid hybridizes with the coding sequence designated in at least one of SEQ ID Nos: 1 or 3 or to the complement to the coding sequence designated in at least one of SEQ ID Nos: 1 or 3. In a preferred embodiment, the hybridization is conducted under mildly stringent or stringent conditions.

In further embodiments, the nucleic acid molecule is an RIEG nucleic acid that is at least 70%, preferably 80%, more preferably 85%, and even more preferably at least 95% homologous in sequence to the nucleic acids shown as SEQ ID Nos: 1 or 3 or to the complement of the nucleic acids shown as SEQ ID Nos: 1 or 3. In another embodiment, the RIEG nucleic acid molecule encodes a polypeptide that is at least 90% and more preferably at least 94% similar in sequence to the polypeptide shown in SEQ ID No: 2.

The invention also provides probes and primers comprising substantially purified oligonucleotides, which correspond to a region of nucleotide sequence which hybridizes to at least 6 consecutive nucleotides of the sequences set forth as SEQ ID Nos: 1 or 3 or complements of the sequences set forth as SEQ ID Nos: 1 or 3, or naturally occurring mutants thereof. In preferred embodiments, the probe/primer further includes a label group attached thereto, which is capable of being detected.

For expression, the subject RIEG nucleic acids can include a transcriptional regulatory sequence, e.g. at least one of a transcriptional promoter (e.g., for constitutive expression or inducible expression) or transcriptional enhancer sequence, which regulatory sequence is operably linked to the RIEG gene sequence. Such regulatory sequences in conjunction with a RIEG nucleic acid molecule can be useful vectors for gene expression. This invention also describes host cells transfected with said expression vector whether prokaryotic or eukaryotic and in vitro (e.g. cell culture) and in vivo (e.g. transgenic) methods for producing RIEG proteins by employing said expression vectors.

In another aspect, the invention features isolated RIEG or Solurshin polypeptides, preferably substantially pure preparations e.g. of plasma purified or recombinantly produced RIEG polypeptides. In preferred embodiments, the polypeptide is a functional transcription factor.

In one embodiment, the polypeptide is identical to or similar to a RIEG protein represented in SEQ ID No: 2. Related members of the vertebrate and particularly the mammalian RIEG family are also within the scope of the invention. Preferably, a RIEG polypeptide has an amino acid sequence at least 60% homologous and preferably at least 80% homologous to the polypeptide represented in SEQ ID No: 2. The subject RIEG proteins also include modified protein, which are resistant to post-translation modification, as for example, due to mutations which alter modification sites (such as tyrosine, threonine, serine or aspargine residues), or which prevent glycosylation of the protein, or which prevent interaction of the protein with intracellular proteins involved in signal transduction.

The RIEG polypeptide can comprise a full length protein, such as represented in SEQ ID No: 2, or it can comprise a fragment corresponding to one or more particular motifs/domains, or to arbitrary sizes, e.g., at least 5, 10, 25, 50, 100, 150, 175, 200, 225, 250 or 260 amino acids in length.

Another aspect of the invention features chimeric molecules (e.g. fusion proteins) comprised of a RIEG protein. For instance, the RIEG protein can be provided as a recombinant fusion protein which includes a second polypeptide portion, e.g., a second polypeptide having an amino acid sequence unrelated (heterologous) to the RIEG polypeptide (e.g. the second polypeptide portion is glutathione-S-transferase, an enzymatic activity such as alkaline phosphatase or an epitope tag).

Yet another aspect of the present invention concerns an immunogen comprising a RIEG polypeptide in an immunogenic preparation, the immunogen being capable of eliciting an immune response specific for a RIEG polypeptide; e.g. a humoral response, an antibody response and/or cellular response. In preferred embodiments, the immunogen comprises an antigenic determinant, e.g. a unique determinant, from the protein represented in SEQ ID No: 2.

A still further aspect of the present invention features antibodies and antibody preparations specifically reactive with an epitope of the RIEG protein. In preferred embodiments the antibody specifically binds to an epitope represented in SEQ ID No: 2.

The invention also features transgenic non-human animals which include (and preferably express) a heterologous form of a RIEG gene described herein, or which misexpress an endogenous RIEG gene (e.g., an animal in which expression of one or more of the subject RIEG proteins is disrupted). Such a transgenic animal can serve as an animal model for studying cellular and tissue disorders comprising mutated or mis-expressed RIEG alleles or for use in drug screening. Alternatively, such a transgenic animal can be useful for expressing recombinant RIEG polypeptides.

In yet another aspect, the invention provides assays, e.g., for screening test compounds to identify inhibitors, or alternatively, potentiators, of an interaction between a RIEG protein and, for example, a virus, an extracellular ligand of the RIEG protein, or an intracellular protein which binds to the RIEG protein. An exemplary method includes the steps of (i) combining a RIEG polypeptide or bioactive fragments thereof, a RIEG target molecule (such as a RIEG ligand or a RIEG substrate), and a test compound, e.g., under conditions wherein, but for the test compound, the RIEG protein and target molecule are able to interact; and (ii) detecting the formation of a complex which includes the RIEG protein and the target polypeptide either by directly quantitating the complex, by measuring inductive effects of the RIEG protein, or, in the instance of a substrate, measuring the conversion to product. A statistically significant change, such as a decrease, in the interaction of the RIEG and target molecule in the presence of a test compound (relative to what is detected in the absence of the test compound) is indicative of a modulation (e.g., inhibition or potentiation of the interaction between the RIEG protein and the target molecule).

Yet another aspect of the present invention concerns a method for modulating the transcription of certain genes in a cell by modulating RIEG bioactivity, (e.g., by potentiating or disrupting RIEG bioactivity). In general, whether carried out in vivo, in vitro, or in situ, the method comprises treating the cell with an effective amount of a RIEG therapeutic so as to alter, relative to the cell in the absence of treatment, the level of transcription of certain genes Accordingly, the method can be carried out with RIEG therapeutics such as peptide and peptidomimetics or other molecules identified in the above-referenced drug screens which agonize or antagonize the effects of signaling from a RIEG protein or ligand binding of a RIEG protein. Other RIEG therapeutics include antisense constructs for inhibiting expression of RIEG proteins, and dominant negative mutants of RIEG proteins which competitively inhibit ligand interactions upstream and signal transduction downstream of the wild-type RIEG protein.

A further aspect of the present invention provides a method of determining if a subject is at risk for Rieger Syndrome or other disorder. The method includes detecting, in a tissue of the subject, the presence or absence of a genetic lesion characterized by at least one of (i) a mutation of a gene encoding a RIEG protein, e.g. represented in one of SEQ ID Nos: 1 or 3 or a homolog thereof; or (ii) the mis-expression of a RIEG gene. In preferred embodiments, detecting the genetic lesion includes ascertaining the existence of at least one of: a deletion of one or more nucleotides from a RIEG gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; a non-wild type level of the protein; and/or an aberrant level of soluble RIEG protein.

For example, detecting the genetic lesion can include (i) providing a probe/primer comprised of an oligonucleotide which hybridizes to a sense or antisense sequence of a RIEG gene or naturally occurring mutants thereof, or 5' or 3' flanking sequences naturally associated with the RIEG gene; (ii) contacting the probe/primer to an appropriate nucleic acid containing sample; and (iii) detecting, by hybridization of the probe/primer to the nucleic acid, the presence or absence of the genetic lesion; e.g. wherein detecting the lesion comprises utilizing the probe/primer to determine the nucleotide sequence of the RIEG gene and, optionally, of the flanking nucleic acid sequences. For instance, the primer can be employed in a polymerase chain reaction (PCR) or in a ligation chain reaction (LCR). In alternate embodiments, the level of a RIEG protein is detected in an immunoassay using an antibody which is specifically immunoreactive with the RIEG protein.

Other features and advantages of the invention will be apparent from the following detailed description and claims.

BRIEF DESCRIPTION OF THE FIGURES

FIG. 1. a) Shows the nucleotide sequence of the human (h) RIEG gene including a portion of the 5' and 3' untranslated region (UTR) (SEQ. ID. NO. 1). In addition, the deduced amino-acid sequence of the human RIEG gene is shown (SEQ. ID. NO.2) based on the coding sequence of hRIEG (SEQ. ID. NO.3). The intron sequence (shown in lower case) was determined only at intron-exon junctions. The start (ATG) and stop (TGA) codons are in boldface, as are the conserved gt and ag sequences flanking each intron and the polyadenylation signals in the 3'UTR. Multiple stop codons 5' from the initiating methionine are underlined and the in-frame stop codon is boxed. The 5' ATG is shown in bold italic. The homeobox has a solid underline, the conserved 14-amino-acid sequence has a dashed underline, and the conserved region in the 3' UTR is italicized. The nucleotide sequence of the mouse (m)Rieg gene is shown in comparison including the 5' and 3' UTR (SEQ. ID. NO.4); and the deduced amino acid sequence of the mouse Rieg gene (SEQ. ID. NO. 5) based on the coding sequence of mRieg (SEQ. ID. NO.6) is shown in comparison to the human. Where mRieg and hRIEG sequences differ, the mouse Rieg nucleotides appear above their corresponding RIEG nucleotides in the main sequence. The homologous coding region, beginning within the third exon (start point marked with an arrow), is indicated by an initial square bracket. Two amino-acid changes in the protein sequence are shown italicized above the main sequence as well. Intron-exon junction sequences have been identified only for RIEG. Nucleotides below the main sequence indicate the positions of and nucleotide changes in the RGS families' mutations; corresponding amino-acid changes are shown as well. The numbers at left and right indicate positions within the cDNA and protein sequences, respectively. The region spanning at nt 950–1760 had significant homology with EST sequences H95407, T64905, and H13139. b) cDNA sequence from the 3'UTR of Rieg. The region sharing 97% homology with the human RIEG3' UTR is italicized.

FIG. 2. a) Alignment of the solurshin homeodomain region with the homeodomains of related proteins. The conserved lysine at position 9 of the third helix is shown in bold. b) Alignment of the 14-amino-acid region in the C-terminal end of solurshin with protein sequences of other homeodomain-containing genes.

DETAILED DESCRIPTION OF THE INVENTION

4.1. General

Figure 3:
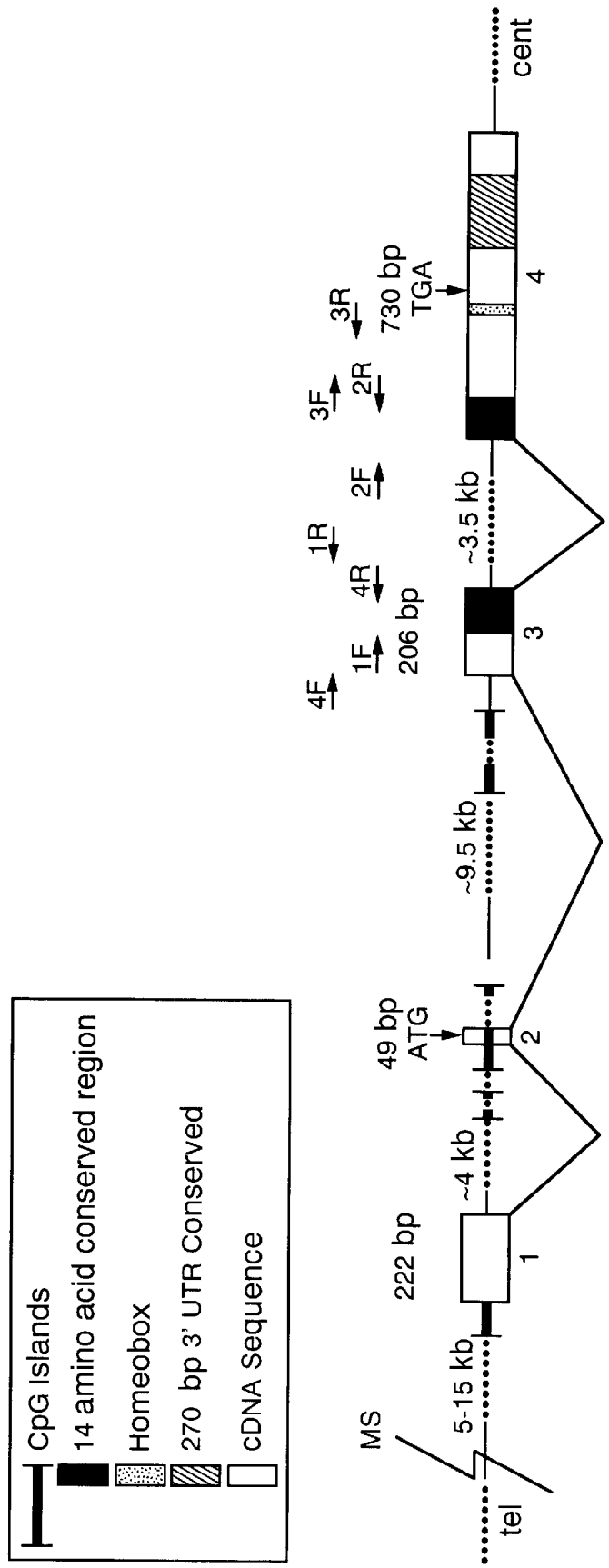
FIG. 3. Genomic organization of the human RIEG gene. The numbered boxes represent the 4 exons; the horizontal lines, introns, with intron sizes indicated by the numbers above them. The line above the second exon shows the position of the 319N1 CpG-island genomic probe used for isolation of the RIEG cDNA. The lines 187,8 and 163 represents cosmids from the cosmid contig comprising the RIEG region. The translation start (ATG) and stop (TGA) signals are indicated. The black box represents the homeobox; the grey box, the 14-amino acid conserved element; and hatched, the conserved region of the 3' UTR of the gene. The arrows indicated the amplification primers used for mutation screening.
Figure 4A:
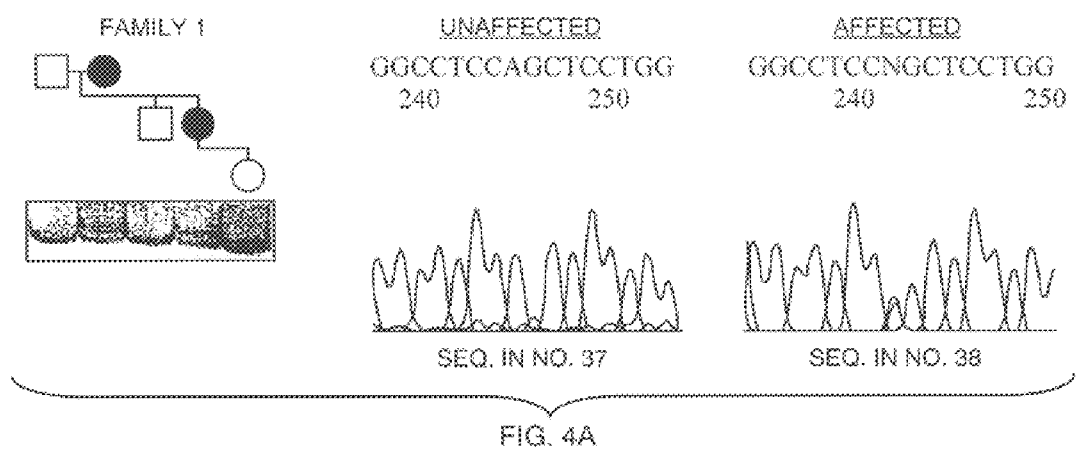
FIG. 4 is a schematic of the results of mutation screening in RIEG families. (A), (B), (C), (D) represent the pedigree and the segregation of the mutated allele in the families 1, 2, 3, 4 respectively. (E), (F) represent probands with de novo RIEG mutations. Open squares, unaffected males; closed squares, affected males; open circles, unaffected females; closed circles, affected females. Corresponding sequences of the amplified genomic DNA from unaffected and affected individuals from the family are shown to the right of each pedigree and the position their mutation occurred is pointed on both pictures with arrows.
Figure 4B:
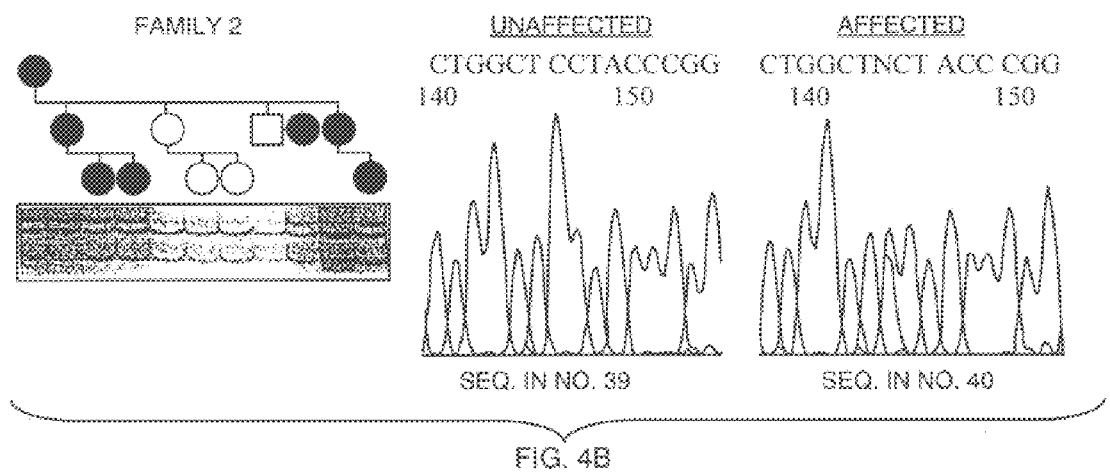
Figure 4D:
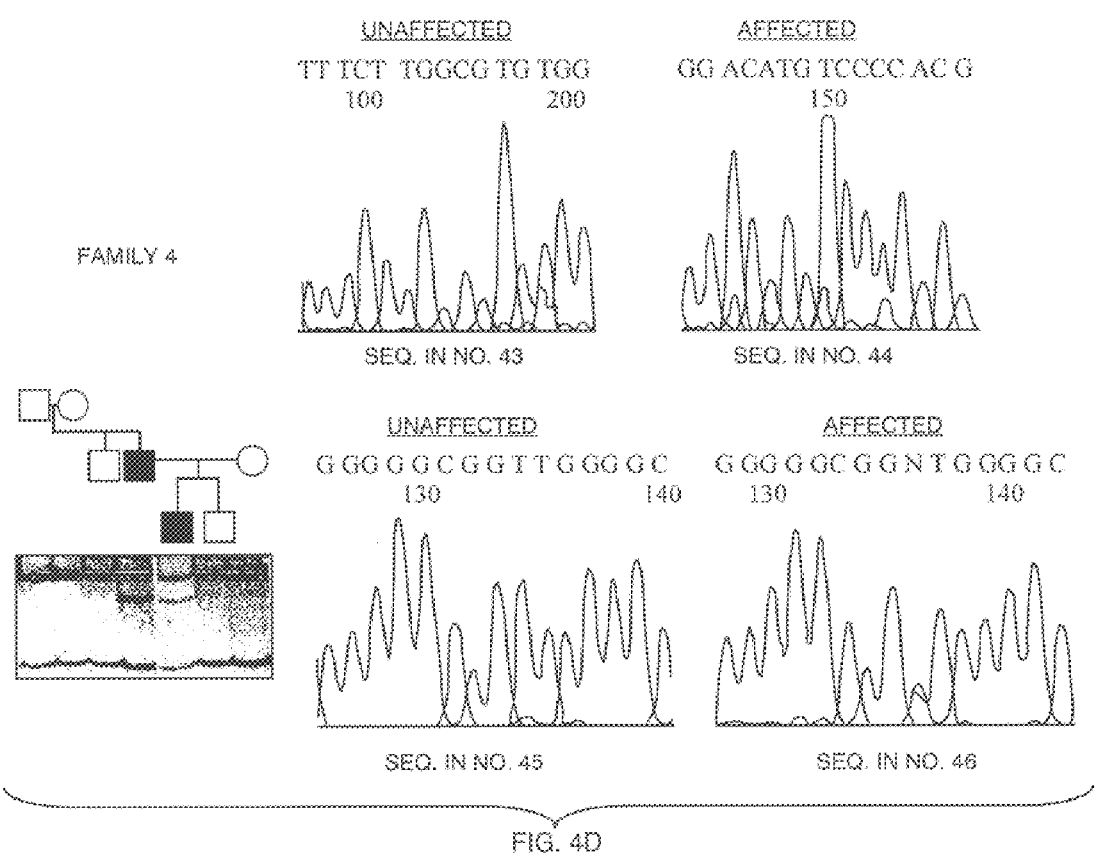
Figure 4E:
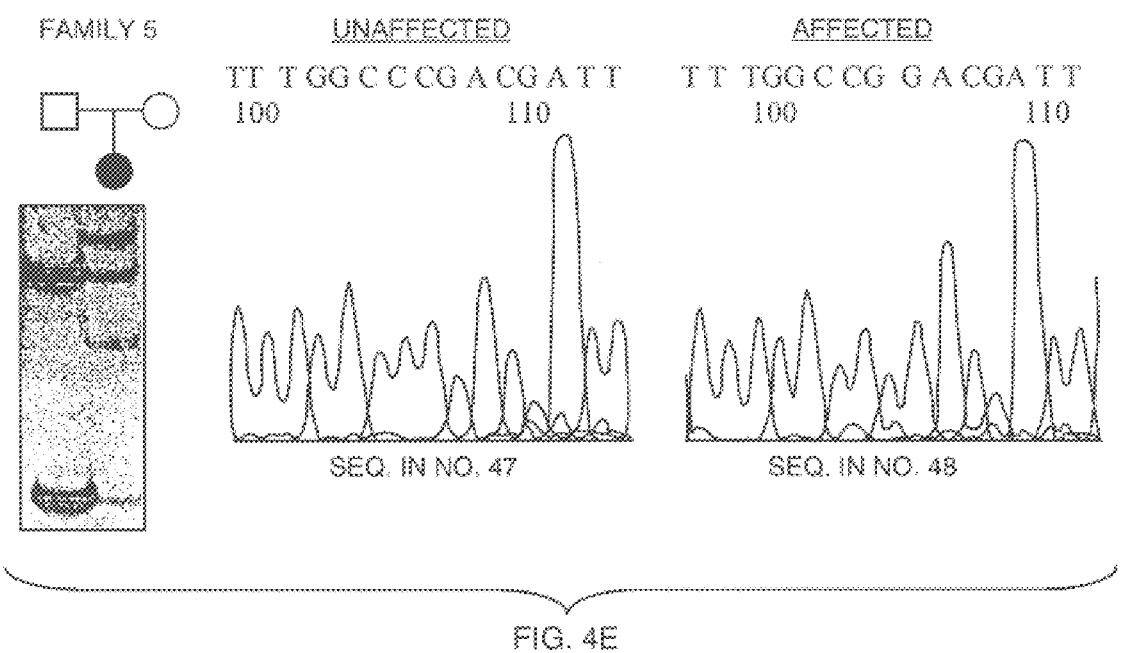
Figure 4F:
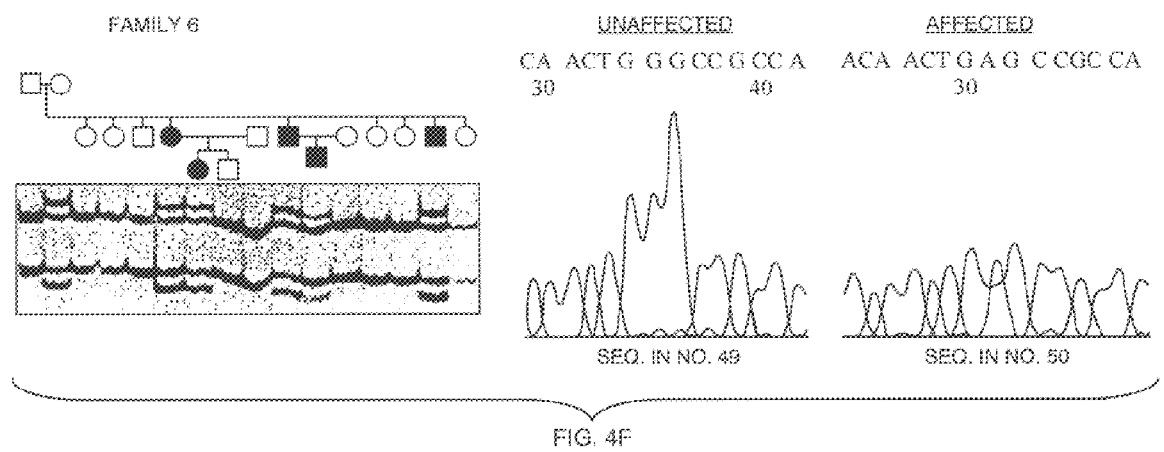

The present invention is based on the discovery of a family of novel genes, referred to herein as "RIEG" gene.

The RIEG genes or gene products provided by the present invention are exemplified by hRIEG and mRIEG. The mRNA transcripts including 5' and 3' untranslated regions as well as the coding region; and the deduced amino acid sequences of hRIEG is shown in FIG. 1 and in SEQ ID Nos: 1, 2 and 3. The mRNA transcripts including: 5' and 3' untranslated regions as well as the coding region; and the deduced amino acid sequences of mRIEG is shown in FIG. 2 and in SEQ ID Nos: 4, 5 and 6.

Based on in situ hybridization, the RIEG gene has been detected in the following tissues: eye mesenchyme, maxillary and mandibular epithelium, Rathke's pouch, limb-body junction, and umbilicus.

The gene itself has several interesting features. First, comparison of the mouse sequence shows there is strong amino acid conservation throughout the gene, particularly in the homeodomain. In addition, there is also a region of strong nucleotide conservation located in the 3' untranslated region of the gene between human and mouse nucleotide sequences. The strongest region of homology extends over 270 nucleotides, beginning 200 base pairs 3' of the stop codon and spanning the polyadenylation signal where 261/270 bp are shared (97%). This strong region of conservation suggests that this is an important and conserved regulatory element.

Another interesting region of sequence conservation is a 14-amino-acid sequence in the C-terminal of the protein that is identical to Ptx1 (Lamonerie T., et al. (1996) Genes Dev. 10:1284–1295) and similar to sequences in genes found in Drosophila, chicken, mouse, and human with craniofacial-specific expression. Such sequences may be targetting recognition sequences that have regional specificity.

As reported herein, six mutations were identified in six unrelated families that both cosegregate with the disorder and were not identified in screens of 200 unaffected individuals drawn from populations of similar ethnic and geographic origin. These mutations were identified in regions that either demonstrated conserved amino acid homology between the human and the mouse, generated stop codons within the gene, or were found immediately adjacent to splice sites, suggesting that a disruption of splicing could result from the mutation. This provides compelling evidence for the role of this gene in the etiology of this disorder.

Further, the expression pattern in the mouse strongly overlaps with the human phenotypic abnormalities (e.g. oral epithelium and dental hypoplasia, periocular mesenchyme and anterior chamber abnormalities and umbilical) providing further evidence for the role of the RIEG gene in the etiology of relevant disorders, as well as strong evidence of conservation between vertebrates. In addition, there is strong expression of the gene in Rathke's pouch, the pituitary anlage, and at least one reported Rieger family has had growth hormone deficiency as part of the phenotype (Feingold et al., (1969) Pediatrics 44:564–569; Sadeghi-Nejad et al., (1974) J. Pediatr. 85: 644–648). This finding together with the discovered strong conservation in the homeobox region suggest that RIEG is important in pituitary development and gene expression.

Accordingly, certain aspects of the present invention relate to nucleic acid molecules encoding vertebrate RIEG proteins, the RIEG proteins, antibodies immunoreactive with RIEG proteins, and preparations of such compositions. In addition, drug discovery assays are provided for identifying agents which can modulate the biological function of RIEG proteins, such as by altering the interaction of vertebrate RIEG molecules with either downstream or upstream elements in the signal transduction pathway. Such agents can be useful therapeutically as further described herein. Moreover, the present invention provides diagnostic and therapeutic assays and reagents for detecting and treating disorders involving, for example, aberrant expression (or loss thereof) of vertebrate RIEG genes. Other aspects of the invention are described below or will be apparent to those skilled in the art in light of the present disclosure.

4.2 Definitions

For convenience, the meaning of certain terms and phrases employed in the specification, examples, and appended claims are provided below.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject RIEG polypeptides with a second amino acid sequence defining a domain (e.g. polypeptide portion) foreign to and not substantially homologous with any domain of one of the RIEG proteins. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-RIEG-Y, wherein RIEG represents a portion of the protein which is derived from one of the RIEG proteins, and X and Y are independently absent or represent amino acid sequences which are not related to one of the RIEG sequences in an organism, including naturally occurring mutants.

"Complementary" sequences as used herein refer to sequences which have sufficient complementarity to be able to hybridize, forming a stable duplex.

A "delivery complex" shall mean a targeting means (e.g. a molecule that results in higher affinity binding of a gene, protein, polypeptide or peptide to a target cell surface and/or increased cellular uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a RIEG polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

As used herein, the term "gene" or "recombinant gene" refers to a nucleic acid molecule comprising an open reading frame encoding one of the RIEG polypeptides of the present invention, including both exon and (optionally) intron sequences. A "recombinant gene" refers to nucleic acid encoding a RIEG polypeptide and comprising RIEG-encoding exon sequences, though it may optionally include intron sequences which are either derived from a chromosomal RIEG gene or from an unrelated chromosomal gene. Exemplary recombinant genes encoding the subject RIEG polypeptides are represented in the appended Sequence Listing. The term "intron" refers to a DNA sequence present in a given RIEG gene which is not translated into protein and is generally found between exons.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the RIEG sequences of the present invention.

The term "interact" as used herein is meant to include detectable interactions between molecules, such as can be detected using, for example, a yeast two hybrid assay. The term interact is also meant to include "binding" interactions between molecules. Interactions may be protein-protein or protein-nucleic acid in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject RIEG polypeptides preferably includes no more than 10 kilobases (kb) of nucleic acid sequence which naturally immediately flanks the RIEG gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "modulation" as used herein refers to both upregulation, i.e., stimulation, and downregulation, i.e. suppression, of a response.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant is expressed in some but not all cells of the animal. The term "tissue-specific chimeric animal" indicates that one of the recombinant RIEG genes is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA techniques, wherein generally, DNA encoding a RIEG polypeptide is inserted into a suitable expression vector which is in turn used to transform a host cell to produce the heterologous protein. Moreover, the, phrase "derived from", with respect to a recombinant RIEG gene, is meant to include within the meaning of "recombinant protein" those proteins having an amino acid sequence of a native RIEG protein, or an amino acid sequence similar thereto which is generated by mutations including substitutions and deletions (including truncation) of a naturally occurring form of the protein.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400 or 425 consecutive nucleotides of a vertebrate, preferably RIEG gene, such as a RIEG sequence designated in one of SEQ ID Nos:1 or 3, or a sequence complementary thereto, or naturally occurring mutants thereof, such that it shows more than 10 times more hybridization, preferably more than 100 times more hybridization, and even more preferably more than 100 times more hybridization than it does to a cellular nucleic acid (e.g., mRNA or genomic DNA) encoding a protein other than a vertebrate RIEG protein as defined herein.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the recombinant mammalian RIEG genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of RIEG proteins.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a mammalian RIEG polypeptide or, in the case of anti-sense expression from the transferred gene, the expression of a naturally-occurring form of the RIEG protein is disrupted.

As used herein, the term "transgene" means a nucleic acid sequence (encoding, e.g., one of the mammalian RIEG polypeptides, or pending an antisense transcript thereto), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the mammalian RIEG proteins, e.g. either agonistic or antagonistic forms. However, transgenic animals in which the recombinant RIEG gene is silent are also contemplated, as for example, the FLP or CRE recombinase dependent constructs described below. Moreover, "transgenic animal" also includes those recombinant animals in which gene disruption of one or more RIEG genes is caused by human intervention, including both recombination and antisense techniques.

As used herein, the term "vector" refers to a nucleic acid molecule: capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

4.3 Nucleic Acids of the Present Invention

As described below, one aspect of the invention pertains to isolated nucleic acids comprising nucleotide sequences encoding RIEG polypeptides, and/or equivalents of such nucleic acids. The term equivalent is understood to include nucleotide sequences encoding functionally equivalent RIEG polypeptides or functionally equivalent peptides having an activity of a vertebrate RIEG protein such as described herein. Equivalent nucleotide sequences will include sequences that differ by one or more nucleotide substitutions, additions or deletions, such as allelic variants; and will, therefore, include sequences that differ from the nucleotide sequence of the RIEG gene shown in any of SEQ ID Nos: 1 or 3 due to the degeneracy of the genetic code.

Preferred nucleic acids are vertebrate RIEG nucleic acids. Particularly preferred vertebrate RIEG nucleic acids are mammalian. Regardless of species, particularly preferred RIEG nucleic acids encode polypeptides that are at least 90% similar to an amino acid sequence of a vertebrate RIEG. Preferred nucleic acids encode a RIEG polypeptide comprising an amino acid sequence at least 92.5% homologous and more preferably 94% homologous with an amino acid sequence of a vertebrate RIEG, e.g., such as a sequence shown in one of SEQ ID Nos: 1 or 3. Nucleic acids which encode polypeptides at least about 95%, and even more preferably at least about 98–99% similarity with an amino acid sequence represented in one of SEQ ID Nos: 2 or 4 are also within the scope of the invention. In a particularly preferred embodiment, the nucleic acid of the present invention encodes an amino acid RIEG sequence shown in one of SEQ ID No: 2. In one embodiment, the nucleic acid is a cDNA encoding a peptide having at least one bioactivity of the subject RIEG polypeptide. Preferably, the nucleic acid includes all or a portion of the nucleotide sequence corresponding to the coding region of SEQ ID Nos: 1 or 3.

Still other preferred nucleic acids of the present invention encode a RIEG polypeptide which includes a polypeptide sequence corresponding to all or a portion of amino acid residues of SEQ ID No: 3 or of SEQ ID No. 6, e.g., at least 2, 5, 10, 25, 50, 100, 150 or 200 amino acid residues of that region. For example, preferred nucleic acid molecules for use as probes/primer or antisense molecules (i.e. noncoding nucleic acid molecules) can comprise at least about 6, 12, 20, 30, 50, 100, 125, 150 or 200 base pairs in length, whereas coding nucleic acid molecules can comprise about 200, 250, 300, 350, 400, 410, 420, 430, 435 or 440 base pairs.

Another aspect of the invention provides a nucleic acid which hybridizes under stringent conditions to a nucleic acid represented by one of SEQ ID Nos: 1 or 3. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature of salt concentration may be held constant while the other variable is changed. In a preferred embodiment, a RIEG nucleic acid of the present invention will bind to one of SEQ ID Nos 1 or 3 under moderately stringent conditions, for example at about 2.0×SSC and about 40° C. In a particularly preferred embodiment, a RIEG nucleic acid of the present invention will bind to one of SEQ ID Nos: 1 or 3 under high stringency conditions, but will not bind to the nucleic acid shown in SEQ ID No: 5.

Preferred nucleic acids have a sequence at least 75% homologous and more preferably 80% and even more preferably at least 85% homologous with an amino acid sequence of a mammalian RIEG, e.g., such as a sequence shown in one of SEQ ID Nos: 1 and 3. Nucleic acids at least 90%, more preferably 95%, and most preferably at least about 98–99% homologous with a nucleic sequence represented in one of SEQ ID Nos: 1 and 3 are of course also within the scope of the invention. In preferred embodiments, the nucleic acid is a mammalian RIEG gene and in particularly preferred embodiments, includes all or a portion of the nucleotide sequence corresponding to the coding region of one of SEQ ID Nos: 1 or 3.

Nucleic acids having a sequence that differs from the nucleotide sequences shown in one of SEQ ID Nos: 1 or 3 due to degeneracy in the genetic code are also within the scope of the invention. Such nucleic acids encode functionally equivalent peptides (i.e., a peptide having a biological activity of a mammalian RIEG polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a mammalian RIEG polypeptide. However, it is expected that DNA sequence polymorphisms that do lead to changes in the amino acid sequences of the subject RIEG polypeptides will exist among mammalians. One skilled in the art will appreciate that these variations in one or more nucleotides (e.g., up to about 3–5% of the nucleotides) of the nucleic acids encoding polypeptides having an activity of a mammalian RIEG polypeptide may exist among individuals of a given species due to natural allelic variation.

As indicated by the examples set out below, RIEG protein-encoding nucleic acids can be obtained from mRNA present in any of a number of eukaryotic cells. It should also be possible to obtain nucleic acids encoding mammalian RIEG polypeptides of the present invention from genomic DNA from both adults and embryos. For example, a gene encoding a RIEG protein can be cloned from either a cDNA or a genomic library in accordance with protocols described herein, as well as those generally known to persons skilled in the art. Examples of tissues and/or libraries suitable for isolation of the subject nucleic acids include breast, spleen, thymus, prostate, testes, ovary, small intestine, colon, and peripheral blood cells, among others. A cDNA encoding a RIEG protein can be obtained by isolating total mRNA from a cell, e.g. a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a mammalian RIEG protein can also be cloned using established polymerase chain reaction techniques in accordance with the nucleotide sequence information provided by the invention. The nucleic acid of the invention can be DNA or RNA. A preferred nucleic acid is a cDNA represented by a sequence selected from the group consisting of SEQ ID Nos: 1 and 3.

4.3.1. Vectors.

This invention also provides expression vectors containing a nucleic acid encoding a RIEG polypeptide, operably linked to at least one transcriptional regulatory sequence. "Operably linked" is intended to mean that the nucleotide sequence is linked to a regulatory sequence in a manner which allows expression of the nucleotide sequence. Regulatory sequences are art-recognized and are selected to direct expression of the subject mammalian RIEG proteins. Accordingly, the term "transcriptional regulatory sequence" includes promoters, enhancers and other expression control elements. Such regulatory sequences are described in Goeddel; *Gene Expression Technology: Methods in Enzymology* 185, Academic Press, San Diego, Calif. (1990). In one embodiment, the expression vector includes a recombinant gene encoding a peptide having an agonistic activity of a subject RIEG polypeptide, or alternatively, encoding a peptide which is an antagonistic form of the RIEG protein. Such expression vectors can be used to transfect cells and thereby produce polypeptides, including fusion proteins, encoded by nucleic acids as described herein. Moreover, the gene constructs of the present invention can also be used as a part of a gene therapy protocol to deliver nucleic acids encoding either an agonistic or antagonistic form of one of the subject mammalian RIEG proteins. Thus, another aspect of the invention features expression vectors for in vivo or in vitro transfection and expression of a mammalian RIEG polypeptide in particular cell types so as to reconstitute the function of, or alternatively, abrogate the function of RIEG-induced signaling in a tissue. This could be desirable, for example, when the naturally-occurring form of the protein is misexpressed; or to deliver a form of the protein which alters differentiation of tissue. Expression vectors may also be employed to inhibit neoplastic transformation.

In addition to viral transfer methods, such as those illustrated above, non-viral methods can also be employed to cause expression of a subject RIEG polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject RIEG polypeptide gene by the targeted cell. Exemplary targeting means of this type include liposomal derived systems, poly-lysine conjugates, and artificial viral envelopes.

4.3.2. Probes and Primers

Moreover, the nucleotide sequences determined from the cloning of RIEG genes from mammalian organisms will further allow for the generation of probes and primers designed for use in identifying and/or cloning RIEG homologs in other cell types, e.g. from other tissues, as well as RIEG homologs from other mammalian organisms. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or anti-sense sequence selected from the group consisting of SEQ ID No:1 and 3, or naturally occurring mutants thereof. For instance, primers based on the nucleic acid represented in SEQ ID Nos:1 and 3 can be used in PCR reactions to clone RIEG homologs.

Likewise, probes based on the subject RIEG sequences can be used to detect transcripts or genomic sequences encoding the same or homologous proteins. In preferred embodiments, the probe further comprises a label group attached thereto and able to be detected, e.g. the label group is selected from amongst radioisotopes, fluorescent compounds, enzymes, and enzyme co-factors.

As discussed in more detail below, such probes can also be used as a part of a diagnostic test kit for identifying cells or tissue which misexpress a RIEG protein, such as by measuring a level of a RIEG-encoding nucleic acid in a sample of cells from a patient; e.g. detecting RIEG mRNA levels or determining whether a genomic RIEG gene has been mutated or deleted. Briefly, nucleotide probes can be generated from the subject RIEG genes which facilitate histological screening of intact tissue and tissue samples for the presence (or absence) of RIEG-encoding transcripts. Similar to the diagnostic uses of anti-RIEG antibodies, the use of probes directed to RIEG messages, or to genomic RIEG sequences, can be used for both predictive and therapeutic evaluation of allelic mutations which might be manifest in, for example, neoplastic or hyperplastic disorders (e.g. unwanted cell growth) or abnormal differentiation of tissue. Used in conjunction with immunoassays as described herein, the oligonucleotide probes can help facilitate the determination of the molecular basis for a developmental disorder which may involve some abnormality associated with expression (or lack thereof) of a RIEG protein. For instance, variation in polypeptide synthesis can be differentiated from a mutation in a coding sequence.

4.3.3. Antisense, Ribozyme and Triplex Techniques

One aspect of the invention relates to the use of the isolated nucleic acid in "antisense" therapy. As used herein, "antisense" therapy refers to administration or in situ generation of oligonucleotide molecules or their derivatives which specifically hybridize (e.g. bind) under cellular conditions, with the cellular mRNA and/or genomic DNA encoding one or more of the subject RIEG proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a mammalian RIEG protein. Alternatively, the antisense construct is an oligonucleotide probe which is generated ex vivo and which, when introduced into the cell causes inhibition of expression by hybridizing with the mRNA and/or genomic sequences of a mammalian RIEG gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668. With respect to antisense DNA, oligodeoxyribonucleotides derived from the translation initiation site, e.g., between the −10 and +10 regions of the RIEG nucleotide sequence of interest, are preferred.

Antisense approaches involve the design of oligonucleotides (either DNA or RNA) that are complementary to RIEG mRNA. The antisense oligonucleotides will bind to the RIEG mRNA transcripts and prevent translation. Absolute complementarity, although preferred, is not required, a sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. *Nature* 372:333). Therefore, oligonucleotides complementary to either the 5' or 3' untranslated, non-coding regions of a RIEG gene could be used in an antisense approach to inhibit translation of endogenous RIEG mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of RIEG mRNA, antisense nucleic acids should be at least six nucleotides in length, and are preferably oligonucleotides ranging from 6 to about 50 nucleotides in length. In certain embodiments, the oligonucleotide is at least 10 nucleotides, at least 17 nucleotides, at least 25 nucleotides, or at least 50 nucleotides.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86:6553–6556; Lemaitre et al., 1987, *Proc. Natl. Acad. Sci.* 84:648–652; PCT Publication No. W088/09810, published Dec. 15, 1988) or the blood-brain barrier (see, e.g., PCT Publication No. W089/10134, published Apr. 25, 1988), hybridization-triggered cleavage agents. (See, e.g., Krol et al., 1988, *BioTechniques* 6:958–976) or intercalating agents. (See, e.g., Zon, 1988, *Pharm. Res.* 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, *Nucl. Acids Res.* 15:6625–6641). The oligonucleotide is a 2'-0-methylribonucleotide (Inoue et al., 1987, *Nucl. Acids Res.* 15:6131–6148), or a chimeric RNA-DNA analogue (Inoue et al., 1987, *FEBS Lett.* 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, *Nucl. Acids Res.* 16:3209), methylphosphonate olgonucleotides can be prepared by use of controlled pore glass polymer supports (Sarin et al., 1988, *Proc. Natl. Acad. Sci. U.S.A.* 85:7448–7451), etc.

While antisense nucleotides complementary to the RIEG coding region sequence could be used, those complementary to the transcribed untranslated region are most preferred. For example, an antisense oligonucleotide as set forth in SEQ ID No. 14 can be utilized in accordance with the invention.

The antisense molecules should be delivered to cells which express the RIEG in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous RIEG transcripts and thereby prevent translation of the RIEG mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, *Nature* 290:304–310), the promoter contained in the 3' long terminal repeat of Rous sarcoma virus (Yamamoto et al., 1980, *Cell* 22:787–797), the herpes thymidine kinase promoter (Wagner et al., 1981, *Proc. Natl. Acad. Sci. U.S.A.* 78:1441–1445), the regulatory sequences of the metallothionein gene (Brinster et al, 1982, *Nature* 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue; (e.g., for brain, herpesvirus vectors may be used), in which case administration may be accomplished by another route (e.g., systematically).

Ribozyme molecules designed to catalytically cleave RIEG mRNA transcripts can also be used to prevent translation of RIEG mRNA and expression of RIEG. (See, e.g., PCT International Publication WO90/11364, published Oct. 4, 1990; Sarver et al., 1990, Science 247:1222–1225). While ribozymes that cleave mRNA at site specific recognition sequences can be used to destroy RIEG mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, *Nature*, 334:585–591. There are hundreds of potential hammerhead ribozyme cleavage sites within the nucleotide sequence of human RIEG cDNA (FIG. 3). Preferably the ribozyme is engineered so that the cleavage recognition site is located near the 5' end of the RIEG mRNA; i.e., to increase efficiency and minimize the intracellular accumulation of non-functional mRNA transcripts.

For example, ribozymes having the sequence set forth in SEQ ID NO 13 can be utilized in accordance with the invention. The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, *Science*, 224:574–578; Zaug and Cech, 1986, *Science*, 231:470–475; Zaug, et al., 1986, Nature, 324:429–433; published International patent application No. WO88/04300 by University Patents Inc.; Been and Cech, 1986, *Cell*, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in RIEG.

As in the antisense approach, the ribozymes can be composed of modified oligonucleotides (e.g. for improved stability, targeting, etc.) and should be delivered to cells which express the RIEG in vivo e.g., hypothalamus and/or the choroid plexus. A preferred method of delivery involves using a DNA construct "encoding" the robozyme under the control of a strong constitutive pol III or pol II promoter, so that transfected cells will produce sufficient quantities of the ribozyme to destroy endogenous RIEG messages and inhibit translation. Because ribozymes unlike antisense molecules, are catalytic, a lower intracellular concentration is required for efficiency.

Endogenous RIEG gene expression can also be reduced by inactivating or "knocking out" the RIEG gene or its promoter using targeted homologous recombination. (E.g., see Smithies et al., 1985, *Nature* 317:230–234; Thomas & Capecchi, 1987, *Cell* 51:503–512; Thompson et al., 1989 *Cell* 5:313–321; each of which is incorporated by reference herein in its entirety). For example, a mutant, non-functional RIEG (or a completely unrelated DNA sequence) flanked by DNA homologous to the endogenous RIEG gene (either the coding regions or regulatory regions of the RIEG gene) can be used, with or without a selectable marker and/or a negative selectable marker, to transfect cells that express RIEG in vivo. Insertion of the DNA construct, via targeted homologous recombination, results in inactivation of the RIEG gene. Such approaches are particularly suited in the agricultural field where modifications to ES (embryonic stem) cells can be used to generate animal offspring with an inactive RIEG (e.g., see Thomas & Capecchi 1987 and Thompson 1989, supra). However this approach can be adapted for use in humans provided the recominant DNA constructs are directly administered or targeted to the required site in vivo using appropriate viral vectors, e.g., herpes virus vectors for delivery to brain tissue; e.g., the hypothalamus and/or choroid plexus.

Alternatively, endogenous RIEG gene expression can be reduced by targeting deoxyribonucleotide sequences complementary to the regulatory region of the RIEG gene (i.e., the RIEG promoter and/or enhancers) to form triple helical structures that prevent transcription of the RIEG gene in target cells in the body. (See generally, Helene, C. 1991, *Anticancer Drug Des.*, 6(6):569–84; Helene, C., et al., 1992, Ann, N.Y. *Accad. Sci.*, 660:27–36; and Maher, L. J., 1992, *Bioassays* 14(12):807–15).

Likewise, the antisense constructs of the present invention, by antagonizing the normal biological activity of one of the RIEG proteins, can be used in the manipulation of tissue, e.g. tissue differentiation, both in vivo and for ex vivo tissue cultures.

Furthermore, the anti-sense techniques (e.g. microinjection of antisense molecules, or transfection with plasmids whose transcripts are anti-sense with regard to a RIEG mRNA or gene sequence) can be used to investigate role of RIEG in developmental events, as well as the normal cellular function of RIEG in adult tissue. Such techniques can be utilized in cell culture, but can also be used in the creation of transgenic animals, as detailed below.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding FCHD534 interactor proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

4.4. Polypeptides of the Present Invention

The present invention also makes available isolated RIEG ("Solurshin") polypeptides which are isolated from, or otherwise substantially free of other. cellular proteins, especially other signal transduction factors and/or transcription factors which may normally be associated with the RIEG polypeptide. The term "substantially free of other cellular proteins" (also referred to herein as "contaminating proteins") or "substantially pure or purified preparations" are defined as encompassing preparations of RIEG polypeptides having less than about 20% (by dry weight) contaminating protein, and preferably having less than about 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified RIEG preparations will lack any contaminating proteins from the same animal from which RIEG is normally produced, as can be accomplished by recombinant expression of, for example, a human RIEG protein in a non-human cell.

Full length proteins or fragments corresponding to one or more particular motifs and/or domains or to arbitrary sizes, for example, at least 5, 10, 25, 50, 75, 100, 125, 150 amino acids in length are within the scope of the present invention.

For example, isolated RIEG polypeptides can include all or a portion of an amino acid sequences corresponding to a RIEG polypeptide represented in one or more of SEQ ID No:2 or 5. Isolated peptidyl portions of RIEG proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a RIEG polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") RIEG protein.

Another aspect of the present invention concerns recombinant forms of the RIEG proteins. Recombinant polypeptides preferred by the present invention, in addition to native RIEG proteins, are at least 92% homologous and more preferably 94% homologous and most preferably 95% homologous with an amino acid sequence represented by any of SEQ ID Nos:2 or 5. Polypeptides which are at least about 98–99% homologous with a sequence selected from the group consisting of SEQ ID Nos: 2 or 5 are also within the scope of the invention. In a preferred embodiment, a RIEG protein of the present invention is a mammalian RIEG protein. In a particularly preferred embodiment a RIEG protein comprises the coding sequence of one of SEQ ID Nos.:2 or 5. In particularly preferred embodiments, a RIEG protein has a RIEG bioactivity.

In certain preferred embodiments, the invention features a purified or recombinant RIEG polypeptide having a molecular weight of approximately 17 kD. It will be understood that certain post-translational modifications, e.g., phosphorylation and the like, can increase the apparent molecular weight of the RIEG protein relative to the unmodified polypeptide chain.

The present invention further pertains to recombinant forms of one of the subject RIEG polypeptides which are encoded by genes derived from a mammalian organism, and which have amino acid sequences evolutionarily related to the RIEG proteins represented in SEQ ID Nos: 2 or 5. Such recombinant RIEG polypeptides preferably are capable of functioning in one of either role of an agonist or antagonist of at least one biological activity of a wild-type ("authentic") RIEG protein of the appended sequence listing. The term "evolutionarily related to", with respect to amino acid sequences of mammalian RIEG proteins, refers to both polypeptides having amino acid sequences which have arisen naturally, and also to mutational variants of mammalian RIEG polypeptides which are derived, for example, by combinatorial mutagenesis. Such evolutionarily derived RIEG polypeptides preferred by the present invention have a RIEG bioactivity and are at least 92% homologous and more preferably 94% homologous and most preferably 98–99% homologous with the amino acid sequence selected from the group consisting of SEQ ID Nos: 2 or 5. In a particularly preferred embodiment, a RIEG protein comprises the amino acid coding sequence of one of SEQ ID No: 2 or 5.

In general, polypeptides referred to herein as having an activity (e.g., are "bioactive") of a mammalian RIEG protein are defined as polypeptides which include an amino acid sequence corresponding (e.g., identical or homologous) to all or a portion of the amino acid sequences of a mammalian RIEG proteins shown in any one or more of SEQ ID Nos: 2 or 5 and which mimic or antagonize all or a portion of the biological/biochemical activities of a naturally occurring RIEG protein. In preferred embodiments, the biochemical activities are related to gene expression, pituitary development, and abdominal development related to umbilical and vitelline artery expression.

Other biological activities of the subject RIEG proteins are described herein or will be reasonably apparent to those skilled in the art. According to the present invention, a polypeptide has biological activity if it is a specific agonist or antagonist of a naturally-occurring form of a mammalian RIEG protein.

The present invention further pertains to methods of producing the subject RIEG polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant RIEG polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant RIEG polypeptide is a fusion protein containing a domain which facilitates its purification, such as GST fusion protein or poly(His) fusion protein.

Moreover, it will be generally appreciated that, under certain circumstances, it may be advantageous to provide homologs of one of the subject RIEG polypeptides which function in a limited capacity as one of either a RIEG agonist (mimetic) or a RIEG antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of RIEG proteins.

Homologs of each of the subject RIEG proteins can be generated by mutagenesis, such as by discrete point mutation(s), or by truncation. For instance, mutation can give rise to homologs which retain substantially the same, or merely a subset, of the biological activity of the RIEG polypeptide from which it was derived. Alternatively, antagonistic forms of the protein can be generated which are able to inhibit the function of the naturally occurring form of the protein, such as by competitively binding to a downstream or upstream member of the biochemical pathway, which includes the RIEG protein. In addition, agonistic forms of the protein may be generated which are constitutively active. Thus, the mammalian RIEG protein and homologs thereof provided by the subject invention may be either positive or negative regulators of gene expression.

The recombinant RIEG polypeptides of the present invention also include homologs of the authentic RIEG proteins, such as versions of those protein which are resistant to proteolytic cleavage, as for example, due to mutations which alter ubiquitination or other enzymatic targeting associated with the protein.

RIEG polypeptides may also be chemically modified to create RIEG derivatives by forming covalent or aggregate conjugates with other chemical moieties, such as glycosyl groups, lipids, phosphate, acetyl groups and the like. Covalent derivatives of RIEG proteins can be prepared by linking the chemical moieties to functional groups on amino acid sidechains of the protein or at the N-terminus or at the C-terminus of the polypeptide.

Modification of the structure of the subject mammalian RIEG polypeptides can be for such purposes as enhancing therapeutic or prophylactic efficacy, stability (e.g., ex vivo shelf life and resistance to proteolytic degradation in vivo), or post-translational modifications (e.g., to alter phosphorylation pattern of protein). Such modified peptides, when designed to retain at least one activity of the naturally-occurring form of the protein, or to produce specific antagonists thereof, are considered functional equivalents of the RIEG polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (I) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, WH Freeman and Co.: 1981). Whether a change in the amino acid sequence of a peptide results in a functional RIEG homolog (e.g. functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject RIEG proteins as well as truncation mutants, and is especially useful for identifying potential variant sequences (e.g. homologs) that are functional in modulating gene expression. The purpose of screening such combinatorial libraries is to generate, for example, novel RIEG homologs which can act as either agonists or antagonist, or alternatively, possess novel activities all together.

Likewise, RIEG homologs can be generated by the present combinatorial approach to selectively inhibit gene expression. For instance, mutagenesis can provide RIEG homologs which are able to bind other signal pathway proteins (or DNA) yet prevent propagation of the signal, e.g. the homologs can be dominant negative mutants. Moreover, manipulation of certain domains of RIEG by the present method can provide domains more suitable for use in fusion proteins.

In one embodiment, the variegated library of RIEG variants is generated by combinatorial mutagenesis at the nucleic acid level, and is encoded by a variegated gene library. For instance, a mixture of synthetic oligonucleotides can be enzymatically ligated into gene sequences such that the degenerate set of potential RIEG sequences are expressible as individual polypeptides, or alternatively, as a set of larger fusion proteins (e.g. for phage display) containing the set of RIEG sequences therein.

There are many ways by which such libraries of potential RIEG homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential RIEG sequences. The synthesis of degenerate oligonucleotides is well known in the art (see for example, Narang, SA (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Likewise, a library of coding sequence fragments can be provided for a RIEG clone in order to generate a variegated population of RIEG fragments for screening and subsequent selection of bioactive fragments. A variety of techniques are known in the art for generating such libraries, including chemical synthesis., In one embodiment, a library of coding sequence fragments can be generated by (i) treating a double stranded PCR fragment of a RIEG coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of RIEG homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate RIEG sequences created by combinatorial mutagenesis techniques.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89:7811–7815; Yourvan et al., 1992, *Parallel Problem Solving from Nature*, 2., In Maenner and Manderick, eds., Elsevir Publishing Co., Amsterdam, pp. 401–410; Delgrave et al., 1993, *Protein Engineering* 6(3):327–331).

The invention also provides for reduction of the mammalian RIEG proteins to generate mimetics, e.g. peptide or non-peptide agents, which are able to disrupt binding of a mammalian RIEG polypeptide of the present invention with either upstream or downstream components. Thus, such mutagenic techniques as described above are also useful to map the determinants of the RIEG proteins which participate in protein-protein interactions involved in, for example, binding of the subject RIEG polypeptide to proteins which may function upstream (including both activators and repressors of its activity) or to proteins or nucleic acids which may function downstream of the RIEG polypeptide, whether they are positively or negatively regulated by it. To illustrate, the critical residues of a subject RIEG polypeptide which are involved in molecular recognition of a component upstream or downstream of a RIEG can be determined and used to generate RIEG-derived peptidomimetics which competitively inhibit binding of the authentic RIEG protein with that moiety. By employing, for example, scanning mutagenesis to map the amino acid residues of each of the subject RIEG proteins which are involved in binding other extracellular proteins, peptidomimetic compounds can be generated which mimic those residues of the RIEG protein which facilitate the interaction. Such mimetics may then be used to interfere with the normal function of a RIEG protein. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

4.4.1. Cells Expressing Recombinant RIEG Polypeptides.

This invention also pertains to a host cell transfected to express a recombinant form of the subject RIEG polypeptides. The host cell may be any prokaryotic or eukaryotic cell. Thus, a nucleotide sequence derived from the cloning of mammalian RIEG proteins, encoding all or a selected portion of the full-length protein, can be used to produce a recombinant form of a RIEG polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. MAP kinase, p53, WT1, PTP phosphotases, SRC, and the like. Similar procedures, or modifications thereof, can be employed to prepare recombinant RIEG polypeptides by microbial means or tissue-culture technology in accord with the subject invention.

The recombinant RIEG genes can be produced by ligating nucleic acid encoding a RIEG protein, or a portion thereof, into a vector suitable for expression in either prokaryotic cells, eukaryotic cells, or both. Expression vectors for production of recombinant forms of the subject RIEG polypeptides include plasmids and other vectors. For instance, suitable vectors for the expression of a RIEG polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in east. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, a RIEG polypeptide is produced recombinantly utilizing an expression vector generated by sub-cloning the coding sequence of one of the RIEG genes represented in SEQ ID Nos: 1 and 3.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

In some instances, it may be desirable to express the recombinant RIEG polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a RIEG protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing RIEG-derived polypeptides in a host which produces MAP (e.g., *E. coli* or CM89 or *S. cerevisiae*), or in vitro by use of purified MAP (e.g., procedure of Miller et al., supra).

In other embodiments transgenic animals, described in more detail below could be used to produce recombinant proteins.

4.4.2 Fusion Proteins and Immunogens.

In another embodiment, the coding sequences for the polypeptide can be incorporated as a part of a fusion gene including a nucleotide sequence encoding a different polypeptide. This type of expression system can be useful under conditions where it is desirable to produce an immunogenic fragment of a RIEG protein. For example, the VP6 capsid protein of rotavirus can be used as an immunologic carrier protein for portions of the RIEG polypeptide, either in the monomeric form or in the form of a viral particle. The nucleic acid sequences corresponding to the portion of a subject RIEG protein to which antibodies are to be raised can be incorporated into a fusion gene construct which includes coding sequences for a late vaccinia virus structural protein to produce a set of recombinant viruses expressing fusion proteins comprising RIEG epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a RIEG protein and the poliovirus capsid protein can be created to enhance immunogenicity of the set of polypeptide antigens (see, for example, EP Publication No: 0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can also be utilized to generate an immunogen, wherein a desired portion of a RIEG polypeptide is obtained directly from organo-chemical synthesis of the peptide onto an oligomeric branching lysine core (see, for example, Posnett et al. (1988) *JBC* 263:1719 and Nardelli et al. (1992) *J. Immunol.* 148:914). Antigenic determinants of RIEG proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the mammalian RIEG polypeptides of the present invention. For example, RIEG polypeptides can be generated as glutathione-S-transferase (GST-fusion) proteins. Such GST-fusion proteins can enable easy purification of the RIEG polypeptide, as for example by the use of glutathione-derivatized matrices (see, for example, *Current Protocols in Molecular Biology*, eds. Ausubel et al. (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

4.4.3. Antibodies

Another aspect of the invention pertains to an antibody specifically reactive with a RIEG protein. For example, by using immunogens derived from a RIEG protein, e.g. based on the cDNA sequences, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide (e.g., a RIEG polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of a RIEG protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a RIEG protein of a mammal, e.g. antigenic determinants of a protein represented by SEQ ID Nos:2 or 4 or closely related homologs (e.g. at least 92% homologous, and more preferably at least 94% homologous).

Following immunization of an animal with an antigenic preparation of a RIEG polypeptide, anti-RIEG antisera can be obtained and, if desired, polyclonal anti-RIEG antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256: 495–497), the human B cell hybridoma technique (Kozbar et al., (1983) *Immunology*

Today, 4: 72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with a RIEG polypeptide of the present invention and monoclonal antibodies isolated from a culture comprising such hybridoma cells.

The term antibody as used herein is intended to include fragments thereof which are also specifically reactive with one of the subject mammalian RIEG polypeptides. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific and chimeric molecules having affinity for a RIEG protein conferred by at least one CDR region of the antibody.

Antibodies which specifically bind RIEG epitopes can also be used in immunohistochemical staining of tissue samples in order to evaluate the abundance and pattern of expression of each of the subject RIEG polypeptides. Anti-RIEG antibodies can be used diagnostically in immuno-precipitation and immuno-blotting to detect and evaluate RIEG protein levels in tissue as part of a clinical testing procedure. For instance, such measurements can be useful in predictive valuations of the onset or progression of proliferative disorders. Likewise, the ability to monitor RIEG protein levels in an individual can allow determination of the efficacy of a given treatment regimen for an individual afflicted with such a disorder. The level of RIEG polypeptides may be measured from cells in bodily fluid, such as in samples of cerebral spinal fluid or amniotic fluid, or can be measured in tissue, such as produced by biopsy. Diagnostic assays using anti-RIEG antibodies can include, for example, immunoassays designed to aid in early diagnosis of a degenerative disorder, particularly ones which are manifest at birth. Diagnostic assays using anti-RIEG polypeptide antibodies can also include immunoassays designed to aid in early diagnosis and phenotyping neoplastic or hyperplastic disorders.

Another application of anti-RIEG antibodies of the present invention is in the immunological screening of cDNA libraries constructed in expression vectors such as λgt11, λgt18-23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a RIEG protein, e.g. other orthologs of a particular RIEG protein or other paralogs from the same species, can then be detected with antibodies, as, for example, reacting nitrocellulose filters lifted from infected plates with anti-RIEG antibodies. Positive phage detected by this assay can then be isolated from the infected plate. Thus, the presence of RIEG homologs can be detected and cloned from other animals, as can alternate isoforms (including splicing variants) from humans.

4.5 Methods of Treating Disease

The RIEG therapeutics of the present invention can be used in treatment of Rieger Syndrome, or associated conditions including pituitary disorders and abdominal disorders related to umbilical and vitelline artery expression.

A "RIEG therapeutic," whether an antagonist or agonist of wild type RIEG, can be, as appropriate, any of the preparations described above, including isolated polypeptides, gene therapy constructs, antisense molecules, peptidomimetics or agents identified in the drug assays provided herein.

Since, in some cases, genes may be upregulated in a disease state and in other cases may be downregulated, it will be desirable to activate and/or potentiate or suppress and/or downmodulate RIEG bioactivity depending on the condition to be treated using the techniques compounds and methods described herein. Some genes may be underexpressed in certain disease states. Several genes are now known to be down-regulated in monocytes under disease conditions. For example, bcl-2 and glutathione peroxidase gene expression is down-regulated in the monocytes of patients exposed to a high lipid diet, e.g. cholesterol or fat, that leads to high serum LDL levels. The activity of RIEG gene products may be in some way impaired, leading to the development of cardiovascular disease symptoms. Such down-regulation of RIEG gene expression or decrease in the activity of a RIEG protein may have a causative or exacerbating effect on the disease state.

Among the approaches which may be used to ameliorate disease symptoms involving the misexpression of a RIEG gene are, for example, antisense, ribozyme, and triple helix molecules described above. Compounds that compete with an RIEG protein for binding to upstream or downstream element in a signaling cascade will antagonize a RIEG protein, thereby inducing a therapeutic effect. Examples of suitable compounds include the antagonists or homologues described in detail above. In other instances, the increased expression or bioactivity of a RIEG protein may be desirable and may be accomplished by, for example the use of the RIEG agonists or mimetics or by gene replacement therapy, as described herein.

Compounds identified as increasing or decreasing RIEG gene expression or protein activity can be administered to a subject at therapeutically effective dose to treat or ameliorate a disease or condition.

4.5.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.5.2. Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

In clinical settings, the gene delivery systems for the therapeutic RIEG gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057). A RIEG gene, such as any one of the sequences represented in the group consisting of SEQ ID NO: 1 or 3, or a sequence homologous thereto can be delivered in a gene therapy construct by electroporation using techniques described, for example, by Dev et al. ((1994) *Cancer Treat Rev* 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.6 Diagnostic and Prognostic Assays

In the diagnostic and prognostic assays described herein, in addition to the RIEG nucleic acid molecules and polypeptides described above, the present invention provides for the use of nucleic comprising at least a portion of the nucleic acid sequence shown in SEQ ID No:1 or 3 or polypeptides comprising at least a portion of the amino acid sequence shown in SEQ ID No:2.

The present method provides a method for determining if a subject is at risk for a disorder characterized by aberrant cell proliferation and/or differentiation. In preferred embodiments, the methods can be characterized as comprising detecting, in a sample of cells from the subject, the presence or absence of a genetic lesion characterized by at least one of (i) an alteration affecting the integrity of a gene encoding a RIEG-protein, or (ii) the mis-expression of the RIEG gene. To illustrate, such genetic lesions can be detected by ascertaining the existence of at least one of (i) a deletion of one or more nucleotides from a RIEG gene, (ii) an addition of one or more nucleotides to a RIEG gene, (iii) a substitution of one or more nucleotides of a RIEG gene, (iv) a gross chromosomal rearrangement of a RIEG gene, (v) a gross alteration in the level of a messenger RNA transcript of a RIEG gene, (vii) aberrant modification of a RIEG gene, such as of the methylation pattern of the genomic DNA, (vii) the presence of a non-wild type splicing pattern of a messenger RNA transcript of a RIEG gene, (viii) a non-wild type level of a RIEG-protein, (ix) allelic loss of a RIEG gene, and (x) inappropriate post-translational modification of a RIEG-protein. As set out below, the present invention provides a large number of assay techniques for detecting lesions in a RIEG gene, and importantly, provides the ability to discern between different molecular causes underlying RIEG-dependent aberrant cell growth, proliferation and/or differentiation.

In an exemplary embodiment, there is provided a nucleic acid composition comprising a (purified) oligonucleotide probe including a region of nucleotide sequence which is capable of hybridizing to a sense or antisense sequence of a RIEG gene, such as represented by any of SEQ ID Nos: 1 and 3, or naturally occurring mutants thereof, or 5' or 3' flanking sequences or intronic sequences naturally associated with the subject. RIEG genes or naturally occurring mutants thereof. The nucleic acid of a cell is rendered accessible for hybridization, the probe-is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

As set out above, one aspect of the present invention relates to diagnostic assays for determining, in the context of cells isolated from a patient, if mutations have arisen in one or more RIEG of the sample cells. The present method provides a method for determining if a subject is at risk for a disorder characterized by aberrant cell proliferation and/or differentiation. In preferred embodiments, the method can be generally characterized as comprising detecting, in a sample of cells from the subject, the presence or absence of a genetic lesion characterized by an alteration affecting the integrity of a gene encoding a RIEG. To illustrate, such genetic lesions can be detected by ascertaining the existence of at least one of (i) a deletion of one or more nucleotides from a RIEG-gene, (ii) an addition of one or more nucleotides to a RIEG-gene, (iii) a substitution of one or more nucleotides of a RIEG-gene, and (iv) the presence of a non-wild type splicing pattern of a messenger RNA transcript of a RIEG-gene. As set out below, the present invention provides a large number of assay techniques for detecting lesions in RIEG genes, and importantly, provides the ability to discern between different molecular causes underlying RIEG-dependent aberrant cell growth, proliferation and/or differentiation.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the RIEG-gene (see Abravaya et al. (1995) *Nuc Acid Res* 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a RIEG gene under conditions such that hybridization and amplification of the RIEG-gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In a preferred embodiment of the subject assay, mutations in a RIEG gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the RIEG gene and detect mutations by comparing the sequence of the sample RIEG with the corresponding wild-type (control) sequence. Exemplary sequencing reactions include those based on techniques developed by Maxim and Gilbert (*Proc. Natl Acad Sci USA* (1977) 74:560) or Sanger (Sanger et al (1977) *Proc. Nat. Acad Sci* 74:5463). It is also contemplated that any of a variety of automated sequencing procedures may be utilized when performing the subject assays (*Biotechniques* (1995) 19:448), including by sequencing by mass spectrometry (see, for example PCT publication WO 94/16101; Cohen et al. (1996) *Adv Chromatogr* 36:127–162; and Griffin et al. (1993) *Appl Biochem Biotechnol* 38:147–159). It will be evident to one skilled in the art that, for certain embodiments, the occurence of only one, two or three of the nucleic acid bases need be determined in the sequencing reaction. For instance, A-tract or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA heteroduplexes (Myers, et al. (1985) *Science* 230:1242). In general, the art technique of "mismatch cleavage" starts by providing heteroduplexes of formed by hybridizing (labelled) RNA or DNA containing the wild-type RIEG sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; Saleeba et al (1992) Methods Enzymod. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in RIEG cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a RIEG sequence, e.g., a wild-type RIEG sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in RIEG genes. For example, single strand conformation polymorphism (SSCP) may be used to detect differences in electrophoretic mobility between mutant and wild type nucleic acids (Orita et al. (1989) *Proc Natl. Acad Sci USA* 86:2766, see also Cotton (1993) *Mutat Res* 285:125–144; and Hayashi (1992) *Genet Anal Tech Appl* 9:73–79). Single-stranded DNA fragments of sample and control RIEG nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al (1989) *Proc. Natl Acad. Sci USA* 86:6230). Such allele speicific oligonucleotide hybridization techniques may be used to test one mutation per reaction when oligonucleotides are hybridized to PCR amplified target DNA or a number of different mutations when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) *Nucleic Acids Res*. 17:2437–2448) or at the extreme 3' end of one primer where, under appropriate conditions, mismatch can prevent, or reduce polymerase extension (Prossner (1993) *Tibtech* 11:238. In addition it may be desirable to introduce a novel restriction site in the region of the mutation to create cleavage-based detection (Gasparini et al (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

For mutations that produce premature termination of protein translation, the protein truncation test (PTT) offers an efficient diagnostic approach (Roest, et. al., (1993) *Hum. Mol. Genet*. 2:1719–21; van der Luijt, et. al., (1994) *Genomics* 20:1–4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

Another embodiment of the invention provides for a nucleic acid composition comprising a (purified) oligonucleotide probe including a region of nucleotide sequence which is capable of hybridizing to a sense or antisense sequence of a RIEG-gene, or naturally occurring mutants thereof, or 5' or 3' flanking sequences or intronic sequences naturally associated with the subject RIEG-genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels. Such oligonucleotide probes can be used for both predictive and therapeutic evaluation of allelic mutations which might be manifest in, for example, neoplastic or hyperplastic disorders (e.g. aberrant cell growth).

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a RIEG gene.

Any cell type or tissue, preferably monocytes, endothelial cells, or smooth muscle cells, in which the RIEG is expressed may be utilized in the diagnostics described below. For example, a subject's bodily fluid (e.g. blood) can be obtained by known techniques (e.g. venipuncture). Alternatively, nucleic acid tests can be performed on dry samples (e.g. hair or skin). Fetal nucleic acid samples can be obtained from maternal blood as described in International Patent Application No. WO91/07660 to Bianchi. Alternatively, amniocytes or chorionic villi may be obtained for performing prenatal testing.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutant RIEG proteins, which are discussed, above, may also be used indisease diagnostics and prognostics. Such diagnostic methods, may be used to detect abnormalities in the level of RIEG protein expression, or abnormalities in the structure and/or tissue, cellular, or subcellular location of RIEG protein. Structural differences may include, for example, differences in the size, electronegativity, or antigenicity of the mutant RIEG protein relative to the normal RIEG protein. Protein from the tissue or cell type to be analyzed may easily be detected or isolated using techniques which are well known to one of skill in the art, including but not limited to western blot analysis. For a detailed explanation of methods for carrying out western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of RIEG proteins. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the RIEG protein, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an anti-RIEG protein specific antibody is via linkage to an enzyme and use in an enzyme immunoassay (EIA) (Voller, "The Enzyme Linked Immunosorbent Assay (ELISA)", *Diagnostic Horizons* 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) *Enzyme Immunoassay*, CRC Press, Boca Raton, Fla., 1980; Ishikawa, et al., (eds.) *Enzyme Immunoassay*, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme.

Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Moreover, it will be understood that any of the above methods for detecting alterations in a RIEG gene or gene product can be used to monitor the course of treatment or therapy.

4.7. Drug Screening Assays

In drug screening assays described herein, in addition to the RIEG nucleic acid molecules and polypeptides described above, the present invention also provides for the use of nucleic comprising at least a portion of the nucleic acid sequence shown in SEQ ID No:5 or polypeptides comprising at least a portion of the amino acid sequence shown in SEQ ID No:6.

Furthermore, by making available purified and recombinant RIEG polypeptides, the present invention facilitates the development of assays which can be used to screen for drugs, including RIEG homologs, which are either agonists or antagonists of the normal cellular function of the subject RIEG polypeptides, or of their role in the pathogenesis of cellular differentiation and/or proliferation and disorders related thereto. In one embodiment, the assay evaluates the ability of a compound to modulate binding between a RIEG polypeptide and a molecule, be it protein or DNA, that interacts either upstream or downstream of the RIEG polypeptide in the TGFT signaling pathway. A variety of assay formats will suffice and, in light of the present inventions, will be comprehended by a skilled artisan.

4.7.1 Cell-free Assays

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements. Accordingly, in an exemplary screening assay of the present invention, the compound of interest is contacted with proteins which may function upstream (including both activators and repressors of its activity) or to proteins or nucleic acids which may function downstream of the RIEG polypeptide, whether they are positively or negatively regulated by it. To the mixture of the compound and the upstream or downstream element is then added a composition containing a RIEG polypeptide. Detection and quantification of complexes of RIEG with it's upstream or downstream elements provide a means for determining a compound's efficacy at inhibiting (or potentiating) complex formation between RIEG and the RIEG-binding elements. The efficacy of the compound can be assessed by generating dose response curves from data obtained using various concentrations of the test compound. Moreover, a control assay can also be performed to provide a baseline for comparison. In the control assay, isolated and purified RIEG polypeptide is added to a composition containing the RIEG-binding element, and the formation of a complex is quantitated in the absence of the test compound.

Complex formation between the RIEG polypeptide and a RIEG binding element may be detected by a variety of techniques. Modulation of the formation of complexes can be quantitated using, for example, detectably labeled proteins such as radiolabeled, fluorescently labeled, or enzymatically labeled RIEG polypeptides, by immunoassay, or by chromatographic detection.

Typically, it will be desirable to immobilize either RIEG or its binding protein to facilitate separation of complexes from uncomplexed forms of one or both of the proteins, as well as to accommodate automation of the assay. Binding of RIEG to an upstream or downstream element, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/RIEG (GST/RIEG) fusion proteins can be adsorbed onto glutathione sepharose beads (Sigma-Chemical, St. Louis, Mo.) or glutathione derivatized microtitre plates, which are then combined with the cell lysates, e.g. an $^{35}$S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of RIEG-binding protein found in the bead fraction quantitated from the gel using standard electrophoretic techniques such as described in the appended examples.

Other techniques for immobilizing proteins on matrices are also available for use in the subject assay. For instance, either RIEG or its cognate binding protein can be immobilized utilizing conjugation of biotin and streptavidin. For instance, biotinylated RIEG molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with RIEG but which do not interfere with binding of upstream or downstream elements can be derivatized to the wells of the plate, and RIEG trapped in the wells by antibody conjugation. As above, preparations of a RIEG-binding protein and a test compound are incubated in the RIEG-presenting wells of the plate, and the amount of complex trapped in the well can be quantitated. Exemplary methods for detecting such complexes, in addition to those described above for the GST-immobilized complexes, include immunodetection of complexes using antibodies reactive with the RIEG binding element, or which are reactive with RIEG protein and compete with the binding element; as well as enzyme-linked assays which rely on detecting an enzymatic activity associated with the binding element, either intrinsic or extrinsic activity. In the instance of the latter, the enzyme can be chemically conjugated or provided as a fusion protein with the RIEG-BP. To illustrate, the RIEG-BP can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-RIEG antibodies, can be used. Alternatively, the protein to be detected in the complex can be "epitope tagged" in the form of a fusion protein which includes, in addition to the RIEG sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J.).

4.7.2. Cell Based Assays

In addition to cell-free assays, such as described above, the readily available source of mammalian RIEG proteins provided by the present invention also facilitates the generation of cell-based assays for identifying small molecule agonists/antagonists and the like. For example, cells which are sensitive to TGFβ signals can be caused to overexpress a recombinant RIEG protein in the presence and absence of a test agent of interest, with the assay scoring for modulation in RIEG responses by the target cell mediated by the test agent. As with the cell-free assays, agents which produce a statistically significant change in RIEG-dependent responses (either inhibition or potentiation) can be identified. In an illustrative embodiment, the expression or activity of a RIEG is modulated embryos or cells and the effects of compounds of interest on the readout of interest (such as tissue differentiation, proliferation, tumorigenesis) are measured. For example, the expression of genes which are up- or down-regulated in response to a RIEG-dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected.

Exemplary cell lines may include non-recombinant monocyte cell lines, such as U937 (ATCC# CRL-1593), THP-1 (ATCC# TIB-202), and P388D1 (ATCC# TIB-63); endothelial cells such as HUVEC's and bovine aortic endothelial cells (BAEC's); as well as generic mammalian cell lines such as HeLa cells and COS cells, e.g., COS-7 (ATCC# CRL-1651). Further, the transgenic animals discussed herein may be used to generate cell lines, containing one or more cell types involved in cardiovascular disease, that can be used as cell culture models for this disorder. While primary cultures derived from the cardiovascular disease transgenic animals of the invention may be utilized, the generation of continuous cell lines is preferred. For examples of techniques which may be used to derive a continuous cell line from the transgenic animals, see Small et al., 1985, Mol. Cell Biol. 5:642–648.

For example, the effect of a test compound on a variety of end points could be tested including rates of LDL uptake, adhesion to endothelial cells, transmigration, foam cell formation, fatty streak-formation, and production by foam cells of growth factors such as bFGF, IGF-I, VEGF, IL-1, M-CSF, TGFβ, TGFα, TNFα, HB-EGF, PDGF, IFN-γ, and GM-CSF. Similarly, HUVEC's can be treated with test compounds or transfected with genetically engineered RIEG genes. The HUVEC's can then be examined for phenotypes associated with cardiovascular disease, including, but not limited to changes in cellular morphology, cell proliferation, cell migration, and mononuclear cell adhesion; or for the effects on production of other proteins involved in cardiovascular disease such as ICAM, VCAM, PDGF-β, and E-selectin.

In the event that the RIEG proteins themselves, or in complexes with other proteins, are capable of binding DNA and modifying transcription of a gene, a transcriptional based assay could be used, for example, in which a RIEG responsive regulatory sequence is operably linked to a detectable marker gene.

Monitoring the influence of compounds on cells may be applied not only in basic drug screening, but also in clinical trials. In such clinical trials, the expression of a panel of genes may be used as a "read out" of a particular drug's therapeutic effect.

In yet another aspect of the invention, the subject RIEG polypeptides can be used to generate a "two hybrid" assay (see, for example, U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), for isolating coding sequences for other cellular proteins which bind to or interact with RIEG ("RIEG-binding proteins" or "RIEG-bp"), such as FCHD 534, and the like. Such RIEG-binding proteins would likely also be involved in the propagation of TGFβ signals by the RIEG proteins as, for example, the upstream or downstream elements of the RIEG pathway or as collateral regulators of signal bioactivity.

Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a RIEG polypeptide. The second hybrid protein encodes a transcriptional activation domain fused in frame to a sample gene from a cDNA library. If the bait and sample hybrid proteins are able to interact, e.g., form a RIEG-dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the RIEG and sample proteins.

4.8 Transgenic Animals

These systems may be used in a variety of applications. For example, the cell- and animal-based model systems may be used to further characterize RIEG genes and proteins. In addition, such assays may be utilized as part of screening strategies designed to identify compounds which are capable of ameliorating disease symptoms. Thus, the animal- and cell-based models may be used to identify drugs, pharmaceuticals, therapies and interventions which may be effective in treating disease.

4.8.1. Animal-based Systems

One aspect of the present invention concerns transgenic animals which are comprised of cells (of that animal) which contain a transgene of the present invention and which preferably (though optionally) express an exogenous RIEG protein in one or more cells in the animal. A RIEG transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a RIEG protein can be essential for many forms of lineage analysis and can additionally provide a means to assess the effects of, for example, lack of RIEG expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject RIEG proteins. For example, excision of a target sequence which interferes with the expression of a recombinant RIEG gene, such as one which encodes an antagonistic homolog or an antisense transcript, can be designed to activate expression of that gene. This interference with expression of the protein can result from a variety of mechanisms, such as spatial separation of the RIEG gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant RIEG protein can be regulated via control of recombinase expression.

Use of the cre/loxP recombinase system to regulate expression of a recombinant RIEG protein requires the construction of a transgenic animal containing transgenes encoding both the Cre recombinase and the subject protein. Animals containing both the Cre recombinase and a recombinant RIEG gene can be provided through the construction of "double" transgenic animals. A convenient method for providing such animals is to mate two transgenic animals each containing a transgene, e.g., a RIEG gene and recombinase gene.

One advantage derived from initially constructing transgenic animals containing a RIEG transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic RIEG transgene is silent will allow the study of progeny from that founder in which disruption of RIEG mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the RIEG transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a RIEG transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a RIEG protein (either agonistic or antagonistic), and antisense transcript, or a RIEG mutant.

Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J*. 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

In one embodiment, gene targeting, which is a method of using homologous recombination to modify an animal's genome, can be used to introduce changes into cultured embryonic stem cells. By targeting a RIEG gene of interest in ES cells, these changes can be introduced into the germlines of animals to generate chimeras. The gene targeting procedure is accomplished by introducing into tissue culture cells a DNA targeting construct that includes a segment homologous to a target RIEG locus, and which also includes an intended sequence modification to the RIEG genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a RIEG gene function through the use of a targeting transgene construct designed to undergo homologous recombination with one or more RIEG genomic sequences. The targeting construct can be arranged so that, upon recombination with an element of a RIEG gene, a positive selection marker is inserted into (or replaces) coding sequences of the targeted siganlin gene. The inserted sequence functionally disrupts the RIEG gene, while also providing a positive selection trait. Exemplary RIEG targeting constructs are described in more detail below.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) *J. Embryol. Exp. Morphol.* 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934). Still another preferred ES cell line is the WW6 cell line (Ioffe et al. (1995) *PNAS* 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of insertion is electroporation.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene, for example, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence Alternatively, PCR can be used. Finally, if the marker gene is a gene that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the RIEG coding sequence, transcriptional regulatory sequence, etc. Typically, less than about 1–5% of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, as the appended Examples describe, the transformed ES cells can be microinjected into blastocytes.

The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the RIEG gene knocked out in various tissues of the offspring by probing the Western blot with an antibody against the particular RIEG protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a RIEG-gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. T. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

The present invention is further illustrated by the following examples which should not be construed as limiting in any way. The contents of all cited references (including literature references, issued patents, published patent applications, and co-pending patent applications) cited throughout this application are hereby expressly incorporated by reference.

EXAMPLE 1

Mapping of the Rieger Syndrome Causing Gene and Exclusion of the Epidermal Growth Factor (EGF) Gene as a Candidate Gene for Rieger Syndrome Materials and Methods Patients and Cell Lines.

Seven families were identified with characteristic RGS. In all families at least one individual within the pedigree manifested all three cardinal signs of RGS: abnormalities of the anterior segment of the eye, hypodontia, and failure of normal involution of the periumbilical skin. Individuals were considered to be affected within families if they had any of those features.

The MS cell line was established from a RGS patient with karyotype 46,XX,t(4:16)q26:q22. MS and her daughter HS have the same balanced translocation and ocular features of Rieger syndrome as well as dental hypoplasia.

The LR cell line was established from a patient with an apparent de novo balanced translocation and karyotype 46,XX,t(4;11)q27:121. Both of LR's parents have normal karyotypes, and LR has anterior segment abnormalities, dental hypoplasia, and umbilical outpouching (all consistent with Rieger). In addition, LR has mild development delay and polydactyly.

The AR cell line was established from a patient with the karyotype 46,XY,? del or inv(4)(q26q28). AR had an omphalocele repaired at birth, anterior segment abnormalities, dental hypoplasia, and moderate developmental delay. AR is adopted, and family history data are unavailable.

Single-strand Conformation Polymorphism (SSCP) Analysis and Sequencing.

SSCP analysis was carried out using primers selected from each of the introns of EGF and chosen to flank the appropriate exon and to generate fragments of 100 to 220 base pairs in length. The sequence of primers for each of the individual exons is shown in Table 1. SSCP analysis was carried out using a modification of a technique of Orita et al. (Orita M. et al., (1989) *Genomics* 5:874–879) with $^{35}$S-labeled PCR products run on 6% polyacrylamide gels with 10% glycerol at room temperature. Following autoradiography, films were inspected for potential allelic variants.

with several chromosome 4 STSs. From the total 50 hybrids, three independent cell lines derived from MS were isolated which carried 4q26-tel: M 9-1, MS 22-2, MS 19-2. From the fusion between LR and USW56, 46 hybrids were obtained, and four independent cell lines carrying 4pter-cen-4q26 (LR 11-2, LR 10-1, LR 22-2 and LR 19-2) and 2 hybrids carrying 4q26-4tel (LR 22-2, LR 23-1) were selected. Hybrids AR22-2 and AR24-1 were created from AR lymphoblastoid cell line and contained different chromosome 4 counterparts (Table 2).

TABLE 1

| EGF PRIMERS | SIZE | Tm |
|---|---|---|
| EGF1 FWD: GAAAGTTCAAACTCATCAAG (SEQ ID NO. 51) | 150 | 55 |
| EGF1 REV: GAGTACTTACCCACACAAGTA (SEQ ID NO. 52) | | |
| EGF2 FWD: GGTCTCTTTCTTCCACCCA (SEQ ID NO. 53) | 239 | 51 |
| EGF2 REV: TGTAGGTAAGGGTATTTTAC (SEQ ID NO. 54) | | |
| EGF3 FWD: TAAAATTTGATTTTCGAGAGAG (SEQ ID NO. 55) | 230 | 55 |
| EGF3 REV: CTGAATACAGCAGAATTTACC (SEQ ID NO. 56) | | |
| EGF4 FWD: TGAAGTGTGTTTGCCCTCA (SEQ ID NO. 57) | 267 | 51 |
| EGF4 REV: ATACCAAGAGTAAAACTTAC (SEQ ID NO. 58) | | |
| EGF5 FWD: TTTGTCGGTTGCTTTTTAGG (SEQ ID NO. 59) | 243 | 53 |
| EGF5 REV: CAAGGTCAACGATGACTCAC (SEQ ID NO. 60) | | |
| EGF6 FWD: CCCACTCCAAATAAAGCATC (SEQ ID NO. 61) | 182 | 53 |
| EGF6 REV: CATTACCTTCACAGTCATTC (SEQ ID NO. 62) | | |
| EGF7 FWD: TTTGAATGTATTGTGCTGTTG (SEQ ID NO. 63) | 187 | 53 |
| EGF7 REV: TAATGCAATAAATACTTGTTGC (SEQ ID NO. 64) | | |
| EGF8 FWD: AACACTAATCTGACCTGTCT (SEQ ID NO. 65) | 186 | 54 |
| EGF8 REV: CAAACAAAAGGTAAATAAAGCAA (SEQ ID NO. 66) | | |
| EGF9 FWD: GTAGCATCATTACTAAGCAATT (SEQ ID NO. 67) | 188 | 54 |
| EGF9 REV: GACACAGTTCCAGACAACCA (SEQ ID NO. 68) | | |
| EGF10 FWD: TAAATTCAGCCATATTTGAAATT (SEQ ID NO. 69) | 200 | 53 |
| EGF10 REV: TCCACATCTGTTCAAGTAAC (SEQ ID NO. 70) | | |
| EGF11 FWD: AAATCACAGTGCTGTGTTCT (SEQ ID NO. 71) | 209 | 55 |
| EGF11 REV: ACAGCTTAAAACTGAAGCAG (SEQ ID NO. 72) | | |
| EGF13 FWD: TATTTGTTGTGTGCTTTCTTG (SEQ ID NO. 73) | 277 | 53 |
| EGF13 REV: AAAATCGCCCATCCCAAAG (SEQ ID NO. 74) | | |
| EGF14 FWD: GGTGTATTTAACAAACTTGAAT (SEQ ID NO. 75) | 230 | 52 |
| EGF14 REV: GAAAGACTGTGTAACATCTC (SEQ ID NO. 76) | | |
| EGF15 FWD: CCCACTTGTGAATTTGTTTC (SEQ ID NO. 77) | 215 | 52 |
| EGF15 REV: TTAGGTAATTGCCACATAATTT (SEQ ID NO. 78) | | |
| FGF16 FWD: AAATTTAATTGCATCTATTGAC (SEQ ID NO. 79) | 181 | 52 |
| EGF16 REV: AGGTATATTGGAGAACTAGT (SEQ ID NO. 80) | | |
| EGF17 FWD: ATAACTGCACGGGATTCTTG (SEQ ID NO. 81) | 181 | 53 |
| EGF17 REV: TGTCCAAATATGTGAATTTGC (SEQ ID NO. 82) | | |
| EGF18 FWD: CCTAAATATTGCACTAGTTCATAAT (SEQ ID NO. 83) | 192 | 59 |
| EGF18 REV: CCCTCCTCCCCAGCACATGT (SEQ ID NO. 84) | | |
| EGF19 FWD: TCTCTCCCGTACTCTGTCTT (SEQ ID NO. 85) | 184 | 56 |
| EGF19 REV: TCCCCTTCACTGTAGACCAC (SEQ ID NO. 86) | | |
| EGF20 FWD: GAAAGTAAAAGTAATGTCTTGG (SEQ ID NO. 87) | 215 | 53 |
| EGF20 REV: ATCTCTCTGTCCATCAGCAA (SEQ ID NO. 88) | | |
| EGF21 FWD: CTGATGACCTCTGTTTGTGT (SEQ ID NO. 89) | 234 | 53 |
| EGF21 REV: AAAGAGGTTTCCAGTACCAA (SEQ ID NO. 90) | | |
| EGF22 FWD: TGAGATTGTCTCAAATTTTGG (SEQ ID NO. 91) | 178 | 51 |
| EGF22 REV: TCCTTGCTTCATCTGCTTTG (SEQ ID NO. 92) | | |
| EGF23 FWD: AATATCCTCTCTCCCTCCTT (SEQ ID NO. 93) | 139 | 54 |
| EGF23 REV: ACCGAGGAGCCAGGATAAAA (SEQ ID NO. 94) | | |
| EGF24 FWD: GAATATTGAAATTTCTTTTGTC (SEQ ID NO. 95) | 317 | 50 |
| EGF24 REV: TTCTTCTTGACTTTCCTTTTA (SEQ ID NO. 96) | | |

DNA sequence analysis on individual exons demonstrating SSCP variants was carried out using a technique of Sheffield (Sheffield, V. C. et al. (1993) *Genomics* 16:325–332). All sequences were compared to previously published cDNA sequences for EGF.

Somatic Cell Hybrid Creation and Breakpoint Mapping

Somatic cell hybrids were obtained from a polyethylene glycol-mediated fusion between lymphoblastoid cells established form the RGS patients carrying the translocations and hamster UCW56 cells (provided by John Wasmuth). Hybrid cell clones that retained the der(4) and had lost all other chromosome 4 material were identified by PCR screening

TABLE 2

Somatic hybrid cell line panel developed from the RS patients carrying translocations

| Number | Content |
|---|---|
| MS9-1 | 4q26-qter: 16pter-q22 |
| MS22-2 | same as above |
| L11-2 | 4pter-q26: 11q21-ter |

TABLE 2-continued

Somatic hybrid cell line panel developed from the RS patients carrying translocations

| Number | Content |
| --- | --- |
| L10-1 | same as above |
| L19-2 | same as above |
| L22-2 | 4q26-ter: 11pter-q21 |
| L23-1 | same as above |
| AR24-2 | ?del or inv(4) (q26q28) |
| AR22-1 | ?normal 4 |

The panel of somatic cell hybrids obtained from the RGS patients carrying translocations were tested with 82 unknown STSs derived from chromosome 4, with the most dense distribution in the region between D4S1564–D4S1573 loci as this region showed linkage with RGS (Murray, J. D. et al., (1992) *Nature Genet*. 2:46–49).

Screening of YAC Libraries

The YAC library used in this study was prepared at CEPH. The YAC library was screened by PCR assays. The YACs for the Généthon markers were identified through the CEPH-Généthon information service on the World Wide Web (http://www.cephb.genethon-map.html).

Construction of the YAC Contig

YAC clones were grown in AHC medium (deficient in uracil and tryptophan), and their DNA was isolated according to the method of Green and Olson (Green, E. D. and M. V. Olson (1990) *Proc. Nat'l. Acad Sci. USA*, 87:1213–1217). Total-yeast DNA containing YAC(s) was prepared in agarose plugs (Dixon, M. J. (1994) *Am. J. Hum. Genetics* 55:372 378), and the YAC and yeast chromosomes were separated and sized by pulsed-field gel electrophoresis using a Biorad CHEF mapper and DR11. Electrophoresis was performed in 0.5 TBE at 12° C. and 240V and with a switch interval of 20–50 sec for 20–25 h. They were stained with ethidium bromide and prepared for DNA transfer to Hybond N+ filters. To visualize the YACs the filters were hybridized with random-prime-labeled total human genomic DNA and autoradiographed MegaBase 11 DNA standards from Biorad were used as size markers.

DNA extracted from the YAC clones was used for amplification with known STSs in the critical region identified by translocation breakpoint mapping as described above. The amplification was carried out in 10 µl total volume, with 20 ng of DNAs, 1 µl of 10×Boehringer PCR buffer, 2.5 pm of each primer, 2 mM of each dNTPs, and 0.25 units of Taq polymerase (Boehringer). The YAC contig was constructed based on the STS content. Additional STSs from the YACs were isolated by Alu-PCR method (Nelson, D. L. et al., *Proc. Nat'l. Acad. Sci, USA*, 86:6686–6690) and tested on the somatic cell hybrid panel as well as with the other YACs to verify the contig integrity. STS49 amplification used primers F-AAGAATTGGGACGTGCAGTG (SEQ ID NO. 97) and R-AGCAGCTTCCACATTTCCTG (SEQ ID NO. 98) at $T_m$=55° C., with a product size of 146 bp.

Cosmid Sublibrary Preparations and Contig Construction

Cosmid sublibraries were made from three YACs covering the breakpoints in LR and MS: 928_e_5 (1130 kb), 747_e_8 (1760 kb) and 896_d_3(1500 kb). Ten milligrams of yeast DNA containing YAC(s) DNA were digested with 0.001 units of Sau3A in a total volume of 100 µl for 10 min. at 37° C. to provide partially digested DNA. The digestion was checked on 0.6% agarose gel. Ultracentrifugation in a sucrose gradient was applied to the reaction, and fractions containing 30- to 500 kb fragments of DNA were selected for further experiments. Preparation of vector (SuperCos) DNA and genomic DNA, ligation, packaging, and preparation of plating cultures were carried out according to an instruction manual from Stratagene. Cosmid libraries from each YAC were plated on 150 mm LB with ampicillin (100 µg/ml). Master and replica lifts were made from each plate using Biodyne 0.45 micromm membranes. The membranes were denaturated and neutralized using manufacturer-specified conditions and UV cross-linked. Cosmid clones containing human DNA inserts were selected by colony hybridization using total human DNA labeled by random prime reaction (Boehringer) as a probe. Human clones were picked into 96-well microtiter plates for manipulation and storage.

From the YAC 928_E_5, 80 human clones were obtained from the total 2000 clones; from YAC 747_e_8, 1,000 clones were selected out of 10,000; and, from YAC 896_d_3, 6,000 from a total of 7,000. Altogether that was equivalent to nearly twenty genomes. First cosmid sublibraries with known STS markers were screened. The original YACs were shown to be positive for D4S1571, D4S1564, D4S193, D4S406, D4S407, D4S1651, D4S448, D4S2350, GATA62A12, and GATA 65D06 by colony hybridization. From three to ten positive clones were identified for each STS. Then cosmid DNA from 370 cosmids, equivalent to nearly 3 genomes was extacted using Qiagen's mini prep protocol. One hundred nanograms of DNA from each individual clone were digested with EcoRI and completion of digestion confirmed on 0.8% agarose gel containing ethidium bromide. Two nanogams of each sample were then electrophoresed in 0.8% agarose gel at 50V for 3 hours following Southern transfer to Hybond+membranes. In order to identify overlapping clones, hybridization was carried out using whole cosmid DNA as a probe. Ten nanograms of whole cosmid DNA were labeled with $^{32}$P-dCTP using a random prime labeling kit from Boehringer, prehybridized for 1 h with human placental DNA (200 µg/ml) at 65° C., and then hybridized with the membranes in a hybridization buffer containing 7% SDS, 10% PEG-8000, 1 mM EDTA, and 200 mg/ml of human placental DNA, at a probe concentration of 10 cpm/ml. The membranes were prehybridized in the same buffer at 65° C. for no less than 4 hours before hybridization (Murata, Y., *Hum Mol. Genet*. (1994) 3:1341–1344).

Cosmids were preliminarily grouped according to the digestion pattern with EcoRI. (Cosmids sharing three or more bands suggested contiguity). Three clones at the end of each contig were selected as probes for Southern hybridization to confirm grouping and to detect clones that bridged contigs (Murata, Y. (1994) *Hum. Mo. Genet*. 3:1341–1344). Cosmid walks were initiated first from two groups of cosmids: the groups being positive for markers D4S2350, EGF, D4S193 and D4S406, as they were considered to be the closest to the breakpoints according to the physical map of the region, and the groups with present Not1 restriction site, as was shown to be strongly associated with CpG islands surrounding the genes. Multiple contigs were assembled, and the end points of each contig were sequenced and mapped back on the somatic cell hybrid panel. The cosmid contig crossing both breakpoints was identified. Amplification primers for STS 240T3 were F-GCTCGCTTCCCAAAATTAGC (SEQ ID NO. 99) and R-CATTATAAGTCGACTATAAGTG (SEQ ID NO. 100), yielding a PCR product of 148 bp; STS 240T7, F-GAGTGTTTAGTTTTGCTTGTG (SEQ ID NO. 101) and R-CCCACTTTTGGGTATGTATCC (SEQ ID NO. 102), with a 137-bp product; STS 222T3, F-TAACCTCTAGCC AATCTGATC (SEQ ID NO. 103), and R-TTGACCACAT CAGCCCAAC (SEQ ID NO. 104); 160 bp; STS 222T7, F-TCTATCTCCTCTTGGATTCAG (SEQ ID NO. 105) and R-AATTGTAGAATGTAGGTCAAAG (SEQ ID NO. 106), 190 bp; STS 187T3, F-CCACGCTTTAAATTCGACTC (SEQ ID NO. 107) and R-TTGGTTATTTGGCAACATTC (SEQ ID NO. 108), 120 bp; STS 187T7, F-CTGTCT CCCAATTCCTCACT (SEQ ID NO. 109) and R-GTCAG CAGTCTGTGACAAGG (SEQ ID NO. 110), 134 bp.

Sequencing

Cosmid DNA was extracted using Qiagen Midi prep and digested with Not1 to linearize (Dugaiczyk, A. et al. (1992) *Nucleic Acids Res.*, 20:6421–6422). Aliquots were checked on 0.8% agarose gel to assure complete digestion. Then the reaction was run through the Microcon column according to the manufacuter's protocol or cleaned with phenol-chloroform and precipitated with ethanol. One to 1.5 µg of cosmid DNA were used for dye terminator sequencing with conditions according to the manufacturer's (Applied Biosystems) protocol and loaded in at Applied Biosystems Model 373A DNA sequencer. Sequences were analyzed using Blast and Grail software available on the WWW.

Results

Mutation Search in the Epidermal Growth Factor Gene

SSCP analysis was performed on PCR amplification products generated from genomic DNA of seven unrelated patients with appropriate oligonucleotides spanning each of 24 exons of the epidermal growth factor (EGF) gene (Table 1). Four abnormal variants were identified as shown in FIG. 2. In all cases the variants were also identified in individuals unaffected with Rieger syndrome and in unrelated family members. The variants then underwent DNA sequence analysis; these sequence differences are shown in FIG. 3 and the specificities of the variants are outlined in Table 3. As can be seen, in three cases single base-pair changes resulted in alterations of the amino acid sequence in exons 14, 15 and 19. In exon 7, differences were also located within coding sequences but resulted in no change in the amino acid sequence.

A control group of 50 unrelated individuals selected from a combination of CEPH parents and other Caucasian individuals available from populations not segregating from Rieger syndrome were studied. The frequencies of the individual allelic variants were calculated from this material and are shown in Table 3. These allelic variants were also compared and haplotyped with previously described variants for the EGF gene as reported in the studies of Murray et al. (Murray, J. D. et al., (1992) *Nature Genet.* 2:46–49; and Murray, J. C. et al., (1986) *Nucleic Acids Research* 14:5117) and Ritty et al., (Ritty T. M. et al. and J. C. Murray (1989) *Nucleic Acid Res.* 17:5870). When haplotypes were combined, a level of heterozygosity of 0.95 in 100 unrelated Caucasians was obtained.

Construction of the High-resolution Map of 4q25-26

Genetic maps of the region have been obtained through the Genethon (http://www.cephb.fr/ceph-genethon-map.html) and the CHLC (http://www.chlc.org/) servers on the World Wide Web. Identified markers were then tested on the somatic cell hybrid panel derived from the Rieger syndrome patients with translocations (Table 2). The panel consisted often cell lines: hybrids MS9-1, MS22-2, and MS19-2, containing the human translocation chromosome 4q26-ter:16pter-q22; hybrids LR11-2, LR10-1, and LR19-2, containing the human translocation chromosome 4pter-q26:11q21-qter; the hybrids LR22-2 and LR23-1, containing the human translocation chromosome 4q26-ter: 11pter-q21, without the normal human chromosome 4 and the reciprocal translocation chromosomes; and hybrids AR22-2 and AR24-1, carrying normal and deleted chromosomes 4. Chromosome-4 markers present in MS9-1, 22-2, and 19-2 must be located distally to both breakpoints (i.e., between the breakpoints and the end of the long arm of chromosome 4), whereas markers missing from the MS hybrid cell lines and present in LR11-2, 10-1, and 19-2 must be from the LR22-2 and LR23-1 cell lines (or vice versa) must be located in between breakpoints. From this analysis it was deduced that the EGF-D4S1571 markers were the closest proximal markers to the breakpoint, and the microsatellite markers D4S1651-D4S406-D4S193 were then closest flanking distal markers (FIG. 3). The genetic distance between D4S1571 and D4S193 was identified as 3 cM.

Localization of the Translocation Breakpoints

The markers flanking the translocation breakpoints were used to screen the CEPH YAC libraries. (The YACs for the Genethon markers were identified through the CEPH-Genethon information service on the WWW). The YAC contig was constructed based on STS content (FIG. 3). Probes from the ends of the YACs were isolated and tested on the somatic cell hybrid panel as well as with the other YACs to verify the contig integrity.

The YACs 928_3_5, 747_3_8, and 896_d_3 contained STSs that were localized proximally as well as distally form both breakpoints; thus, all these YACs crossed both breakpoints, but the STS content of YAC 928_e_5 was different from the STS content of YACs 747_3_8 and 896_d_3. Cosmid sublibraries were made from all three YACs to assure complete representation of the region of interest.

Cosmids positive for the STSs present in the original YACs were identified and used as starting points for the cosmid walks. Multiple contigs were assembled. End points of each contig were sequenced and mapped back on to the somatic cell hybrid panel. A large contig. spanning approximately 500 kb and consisting of about 70 cosmids was identified as encompassing both breakpoints. This region was narrowed down to a cosmid consisting of two cosmids: 240 (overlapping LR's breakpoint) and 222 (overlapping MS's breakpoint; FIG. 3). The distance between breakpoints is approximately 50 kb, as determined by mapping of STSs derived from the cosmids ends.

EXAMPLE 2

Cloning and Characterization of RIEG

Clinical Status of the Rieger Syndrome Pedigrees

Seventeen families were identified with characteristic RGS. In seven of them the patient also had cytogenetic abnormalities. From the remaining ten families at least one of the individuals in the pedigree manifested all normal involution of the periumbilical skin (Table 3).

TABLE 3

Rieger syndrome patients' features and etiologic mutations in the RIEG gene sequence and adjacent regions

| Family no. | Diagnosed by | Features | Variability within family | Mutation (region and nature) |
|---|---|---|---|---|
| 1 | JCM | | | |
| 2 | WLA | | | |

TABLE 3-continued

Rieger syndrome patients' features and etiologic mutations in the RIEG gene sequence and adjacent regions

| Family no. | Diagnosed by | Features | Variability within family | Mutation (region and nature) |
|---|---|---|---|---|
| 3 | KWS | | | homeobox |
| 4 | JSB | | | homeobox |
| 5 | DBN | | | intron |
| 6 | PB | | | homeobox |
| MS | BUZ | | | translocation occurred at ~5–15 kb from 5' region of gene |
| LR | JCC | | | translocation occurred at ~55–65 kb from 5' region of gene |

Identification of CpG Islands

CpG islands were identified by restriction analysis of the cosmids from the contig spanning the cytogenetic breakpoints with EcoRI, HindIII, PstI, and the rare-cutter enzymes NotI, HPaII, SmaI, EagII, and SacII. Significant overrepresentation of CG cut sites in 203 kb DNA fragment relative to an average distribution (Lindsay, S. and Bird, A. P. (1987) Nature 327:336–338) indicated likely CpG-island presence. Such fragments were subcloned into pBlueScript plasmids and sequenced in both directions to ascertain CG-rich content. Sequences were analyzed using Blastn and Grail search engines available on the World-Wide Web.

cDNA Library Screening

Several cDNA libraries were used in this study: human fetal brain (Stratagene), human craniofacial constructed from mRNA derived from the craniofacial region of human embryos ranging from 42 to 53 days' gestation (Padanilam, B. J., Stadler H. S., Mills, K. A., McLeod, L. B., Solursh, M., Lee, B., Ramirez, F., Buetow, K. H., and Murray, J. C., 1992. Characterization of the human HOX7 cDNA and identification of polymorphic markers. *Hum. Mol. Genet.* 1, 407–410.), mouse embryonic carcinoma (Stratagene), and mouse fetal 15-day (Novagene). The 3.5-kb 319not1.896 and the 2-kb 8ecor1.747 GC-rich fragments were random-prime labeled with P according to instructions from the kit's manufacturer (Boehringer) and were used to screen the craniofacial cDNA library in hybridization. The hybridization was carried out at 55° C. over 18 hours and was followed by several washes at room temperature and by a 2-hour wash at 60° C. in 0.1% SSC and 0.5% SDS. cDNA fragments isolated in this initial screening were then used in subsequent screenings of the same (human craniofacial) and of the other human and mouse cDNA libraries to identify homologous and overlapping clones.

Clone Isolation and Sequencing

Plasmids from positive plaques were isolated from their I-Zap II or Uni-Zap XR hosts by in-vivo excision with R408 helper phage as described by the manufacturer (Stratagene). Bluescript plasmids containing cDNA inserts were sequenced and analyzed using the Blastn and Grail engines.

Genomic Structure and Identification

Exon-intron boundaries were identified by primer walking between the cDNA and genomic cosmid clones. Introns were sized by PCR with exon-specific primers and cosmid-end-derived primers (FIG. 3), the cosmid ends had been previously mapped by restriction and hybridization, with a total of 24 overlapping cosmids identified in the region (Semina, E. et al., (1996) *Am. J. Hum. Genet.*).

SSCP and DNA Analysis

Oligonucleotide primers for the PCR amplification of the various RIEG fragments (See FIG. 3) were as follows: primer I forward GATAAAAGCCAGCAGGGGAA (SEQ ID NO.111) and reverse GAGGGAACTGTAATCTCGCA (SEQ ID NO.112); primer 2 forward GTAATCTGCACTGTGGCATC (SEQ ID NO.113) and reverse CCAGTTGTTGTAGGAATAGCC (SEQ ID NO.114); primer 3 forward AGTTCAATGGGCTCATGCAG (SEQ ID NO.115) and reverse GGGGAAAACATGCTCTGTGA (SEQ ID NO.116). Genomic DNA from the 10 unrelated probands diagnosed with Rieger syndrome, was amplified in a PCR thermocycler (Perkin-Elmer Cetus), with a single four-minute, 94° C. cycle followed by 30 cycles comprising 94° C., 55° C., and 72° C. steps of 30 seconds each, in 10 µl total volume: 1 µl Boehringer PCR buffer, 2.5 pmol of eac primer, 2 mM in each dNTP, and 0.25 units of Taq polymerase (Boehringer). PCR products were heated for four minutes at 95° C. and electrophoresed for four hours at 20 W through a fan-cooled gel composed of 3.3 ml of 10 TBE, 1.37 ml of glycerol, 13.75 ml of MDE mix (from FMC), 36.6 ml of water, 220 µl of 10% APS, and 22 µl of TEMED. After silver staining the gels were visually inspected for potential abnormal variants.

Potential variant fragments were then extracted from the gel, reamplified, sequenced in both directions together with genomic PCR products from the corresponding individual, and compared with the normal sequence. Genomic DNA from family members was analyzed via SSCP to verify cosegregation of the relevant fragment with the phenotype.

In-situ Hybridization

NIH Swiss mice from Harlan (Indianapolis, Ind.) were used in this study. Developmental staging was done according to Theiler, K. (1989) *The House Mouse. Atlas of Embryonic development.*

$^{35}$S-uridine 5'(a-thio) triphosphate (NEN) and digoxigenin (DIG) 5'-triphosphate (Boehringer) were used as labeling materials. The 535 bp DNA fragment (SALI-DraII) of 3'UTR region of the mouse rgs cDNA clone was cloned into pBlueScript vector and used as a probe for in-situ hybridization. Sense and antisense RNA probes were synthesized with labeling material using either T3 or T7 RNA polymerase (Stratagene) linearized DNA. Labeled RNA probes were purified with Bio-spin chromatography columns #30 (Bio-Rad). Probes were hydrolysed before using in hybridization. For $^{35}$S-labeled probes $3.5 \times 10^6$ cpm/kb per 50 µl of hybridization mixture was used, and 300–500 ng of probe per ml of hybridization mixture was used for digoxigenin-labeled probes.

Embryonic mice for radioactive in-situ hybridization were fixed overnight at 4° C. in 4% paraformaldehyde in PBS, dehydrated, cleared in Histosol (National Diagnostics), and embedd in Paraplast Plus (Oxford). Seven-micron sections were cut and mounted onto Superfrost plus slides (Fisher) with DEPC-treated water, dried overnight at 40° C., and then stored at room temperature. Before use the slides were baked at 60° C. overnight and then processed for in-situ hybridization according to the methods described by Sassoon, D. and Rosenthal, N. (1993) *Meth. Enzymol.* 225:384–404. Slides were hybridized overnight at 50° C., washed in 5×SSC at 50° C. to remove coverslips, and then washed in 2×SSC, 50% formamide at 60° C. Autoradiography was done with Kodak NTB-2 emulsion. A two-week exposure time at 4° C. was determined to be optimal. Developed slides were stained for 30 minutes in hematoxuin, dehydrated, cleared in Histosol, and mounted with Permount (Fisher).

Embryonic mice for whole-mount in-situ hybridization were fixed and processed following a modification of the procedures described by Harland and Richard M. H. (1991) *Meth. Cell Bio.* 36:685–695). Briefly, embryos were fixed overnight at 4° C. in 4% paraformaldehyde in M buffer (100 mM MOPS, ph7.4, 2 mM EGTA, 1 mM $MgSO_4$) and then bleached in 3% hydrogen peroxide in M buffer, dehydrated in a graded series of M buffer and methanol, and stored at −20° C. Hybridization was performed at 60° C. overnight with rocking. Post-hybridization washes were done at 60° C. in 2×SSC.

In preparation for antibody incubation the embryos were washed in 10% heat-inactivated sheep serum in PBS+0.5% Tween 20 (PBSTw). A 1/2000 dilution of a-digoxigenin antibody (Boehringer) was added, and the embryos were incubated overnight at 4° C. with gentle rocking. Embryos were rinsed for 24 hours in PBST2 with at least 10 changes of buffer and then washed in color reaction buffer (100 mM Tris, pH 9.0, 50 mM $MgCl_2$, 100 mM NaCl, 0.5% Tween 20, 1 mM levamisole) 3× for 20 minutes each. Color reagents (4.5 $\mu$l/ml NBT and 3.5 $\mu$l/ml BCIP) were then added. The reaction was monitored under a dissecting scope and stopped with 2 washes of PBS. The embryos were again fixed in Bouin's buffer to help preserve the color and dehydrated in a graded series of PBS:glycerol and stored in 80% glycerol: 20% PBS, 0.2% sodium azide.

Results

Cloning of the Gene

Example 1 reports on fine physical mapping of translocation breakpoints on 4q25 from two patients with RGS. By restriction analysis of the cosmids crossing both breakpoints with CG-cutter enzymes six potentially C+G-rich regions ranging from one to four kilobases were identified, subcloned into plasmids and sequenced in both directions. Five fragments were shown to be C+G-rich by sequence analysis.

Screening of a human craniofacial cDNA library (Padanilam, B. J., Stadler H. S., Mills, K. A., McLeod, L. B., Solursh, M., Lee, B., Ramirez, F., Buetow, K. H., and Murray, J. C., 1992. Characterization of the human HOX7 cDNA and identification of polymorphic markers. Hum-.Mol.Genet. 1, 407–410.) with a fragment 3.5-kb 319 not 1.896 identified positive plaques which were cloned and sequenced. The longest clone (1306 bp) was found to contain 1047 bp of a single open reading frame. Rescreening of two different cDNA libraries (human cranofacial [Padanilam, B. J., Stadler H. S., Mills, K. A., McLeod, L. B., Solursh, M., Lee, B., Ramirez, F., Buetow, K. H., and Murray, J. C., 1992. Characterization of the human HOX7 cDNA and identification of polymorphic markers. (*Hum. Mol. Genet.* 1, 407–410) and fetal brain [Stratagene]) with a variety of probes isolated from the original cDNA yielded several new clones, extending the known sequence to 1783 bp, which contained a polyadenylation signals and poly-A tail (FIG. 1).

Sequence analysis of the 5' end of the cDNA revealed high G+C content (66% for bases 1 through 222) and five restriction sites for HpaII, one for SmaI, and one for BstUI—commonly associated with the CpG islands found to surround the transcription sites of vertebrate genes (Lindsay, S. and Bird, A. P. (1987) *Nature* 327:336–338). An ATG initiation codon was found at position 226, followed by a G at 229 (+4 from the beginning of the ATG codon) and preceded by a G at 223 (−3 from the ATG), in agreement with Kozak's rules (Kozak, M. (1987) *Nucleic Acids Res.* 15:8125–48), and represents the only in-frame ATG codon in the 5' region. Two potential CTG codons were identified upstream of the 5' region which might play a role in the regulation of tissue-specific transcription of the gene (Kozak, M. (1987) *J. Mol. Biol.* 196:947–950). The 3' region of the cDNA was found to contain a polyadenylation signal at positions 1393–1399 and 1458–1463 with poly-A tail of 25 nucleotides. Translation of the open reading frame yielded a protein of 271 amino acids.

Sequence comparison using GenBank indicated that it is a novel gene that contains a homeobox, and the gene and encoded protein were named RIEG. The protein alone is also referred to as "Solurshin" (Syndrome of orofacial and umbilical abnormalities of the Rieger syndrome homeobox). Comparison of the RIEG homeodomain with others identified the greatest homology with the recently published murine Ptx-1 and P-OTX proteins which themselves appear to be identical (Lamonerie T., et al. (1996) *Genes Dev.* 10:1284–1295; Szeto, D. P. et al. (1996) *Proc. Natl. Acad. Sci.* 93:7706–7710). The RIEG homeodomain sequence is different from Ptx-1 or P-OTX by just two residues: RIEG has Thr at position 3 of the second helix and an Ala residue at the position 2 of the third helix instead of the Met and Pro residues, respectively, at the corresponding positions in the Ptx-1/P-OTX homeodomain. Both homeodomains, however, share the Lys at position 9 of 35 the predicted third helix (position 50 of the homeodomain) which is characteristic for the bicoid-related proteins as found in *C. elegans* unc-30 gene (Jin Y. et al., (1994) *Nature* 372, 780–783), the murine Otx-1 and Otx-2, and with the Drosophila Otd homeodomains (Simeone, A. et al., *Embo. J.* 12:2735–2747) (FIG. 2). The amino acid at position 9 of the recognition helix has been shown in bicoid and some other homeodomains to determine the specificity of binding to the two bases following the TAAT core (Hanes, S. D. and R. Brent (1989) *Cell* 57:1275–1283; Hanes, S. D. et al, (1994) *Mol. Cell Biol.* 14:3364–3375). Other classes of homeodomain proteins show identity of amino acid at position 9 in the majority of their members: the antp-class proteins usually have a Gln, the paired proteins a Ser, proteins such as cut products usually contain a His, and POU-class proteins a Cys (Hanes, S. D. and R. Brent (1989) *Cell* 14:1275–1283).

A 14-a.a. sequence located in the C-terminal of the homeodomain spanning a.a. 233–246 was found to be conserved in several other homeodomain-containing genes (FIG. 2b). Solurshin and Ptx-1/POT-X have 100% conservation in this region, followed by less homology with chicken prx-1 (known also as gMHox in chicken, MHox, pmx and k2 in mouse, and phox in human (Nohno, T. et al., (1993) *Dev. Bio.* 158: 254–264) and prx-2 (known also as S8 (Leussink, B. et al. (1995) *Mech. Dev.* 52:51–64; KeCr, M. J. et al., (1994) *Pmx. Genomics* 19:334–340; Kuratani, S. et al (1994) *Dev. Bio.* 161:357–369)), human Cart-1 (Zhao, G.Q. et al. (1994) *Mech. Dev.* 48:245–254), *Drosphila aristaless* (Schneitz, K. et. al., (1993) *Genes Dev.* 7:114–129), rat drg11 (Saito, T. et al., (1995) *Mol. Cell. Neurosci* 6:280–292), murine chx10 (Liu, I. S. et al., (1994) *Neuron* 13:377–393) and otp (Simeone, A., et. al., (1994) *Neuron* 13:81–101) proteins. Ptx-1/P-OTX, prx-1 and prx-2, Cart-1, aristaless, chx10 and otp mRNAs are expressed at high levels in the craniofacial region in different species; three of these genes (prx-1 and prx-2, Cart-1) are also expressed in the limb mesenchyme, which correlates with the expression pattern of murine solurshin (see below). This 14-a.a sequence might represent an element important for target specificity of those transcription factors. The fact that proteins sharing this conserved 14-a.a sequence also have correlations in their expression patterns suggest that this may be important for region-specific function of those proteins.

The gene was found to comprise about 18 kb in the human and to consist of four exons of 572, 57, 206, and 1290 nucleotides in length. The initiation codon is located in the second exon with the homeobox region in the third and fourth exons. The genomic structure of the gene is illustrated in FIG. 3. The approximate distances of the most 5' end of RIEG to the translocation breakpoints were approximated by analysis of genomic clones containing both breakpoints in one contig (FIG. 3) and were estimated at 5 to 15 kb for MS and 55 to 65 kb for LR, suggesting position effect as the cause of RGS in those patients. "Position effect" mutations (usually translocations, inversions, deletions, duplications or retroviral integrations) alter gene expression through a long-range effect on chromatin structure (position effect variegation) or by disrupting distal elements of a gene and have been described in Drosphila, mouse, and human (Bedell, M. A., et al. (1996) *Nature Genet.* 12:229–232)).

Mutation Analysis

Ten families with dominant Rieger syndrome have been identified (Table 3). In those families at least one of the affected individuals in the pedigree manifested all three cardinal features of the syndrome: abnormalities of the anterior segment of the eye, hypodonita, and failure of normal involution of the periumbilical skin (FIG. 4). Parts of the exon and adjacent intron sequences were subsequently amplified from the DNA of one affected individual from each of ten Rieger syndrome families and screened for mutations using single-strand conformational polymorphism (SSCP) analysis. The mutation screen was initiated at the homeobox region of the gene using three overlapping sets of primers (FIG. 3) and then expanded to cover the full coding sequence.

Figures 5A, 5B:
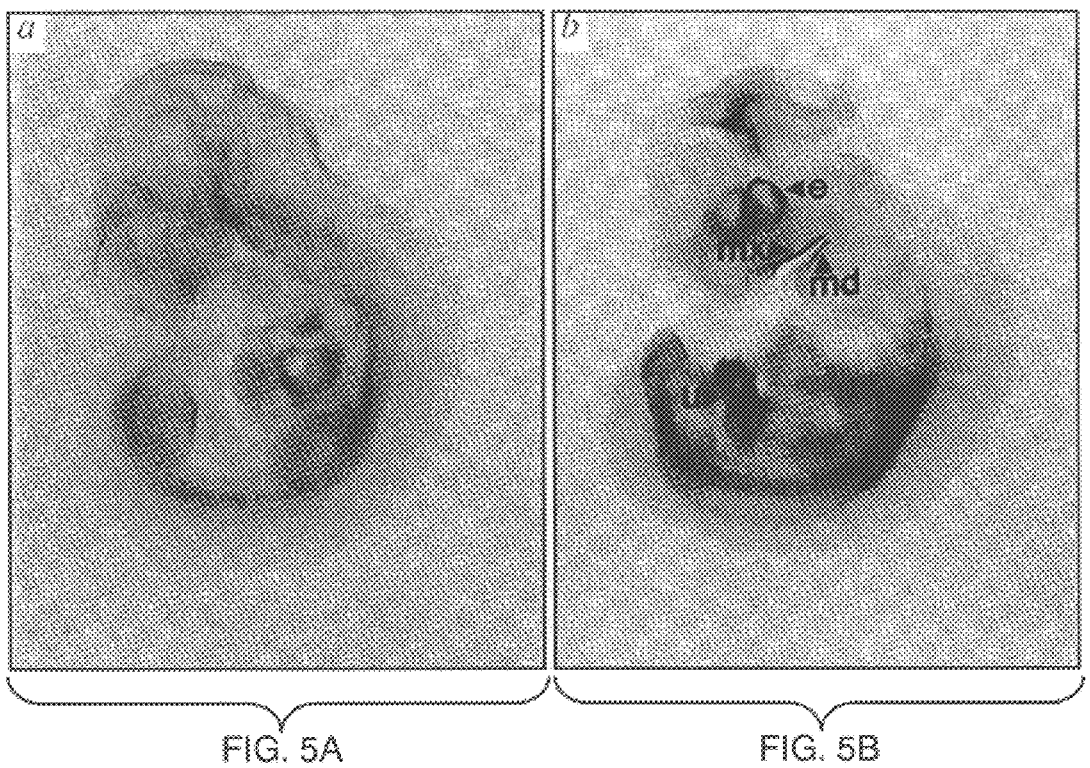
FIG. 5. Whole mount in situ hybridization on mouse day 11 embryos with sense (A) and anti-sense (B) digoxigen labeled riboprobes derived from the 3'UTR of mouse RIEG cDNA. Marked regions of embryo are: eye (e), maxillary (mx) and mandibular (md) and in the umbilical cord (u). Bars: 0.57 mm.
Figure 6A:
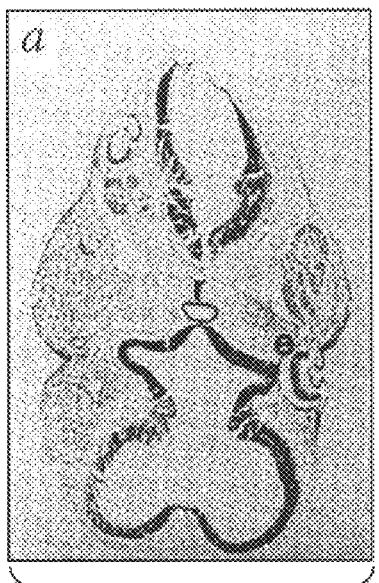
FIG. 6. Shows brightfield (A, B, C) and darkfield (D, E, F) micrographs of sections through the head (A and B) and midgut regions (C) of day 11 mouse embryo. Note the signal around the eye (e) and in Rathke's pouch (r) in (D) (arrows); in the epithelium of the maxillary (mx) and mandibular (md) processes in (E) (arrows); and in (F) at the juncture of the limb (l) to the body, the dorsal mesentery (dm) the vitteline (v) and umbilical (u) vessels (arrows). Bars: d and E, 0.37 mm; F, 0.42 mm.
Figure 6B:
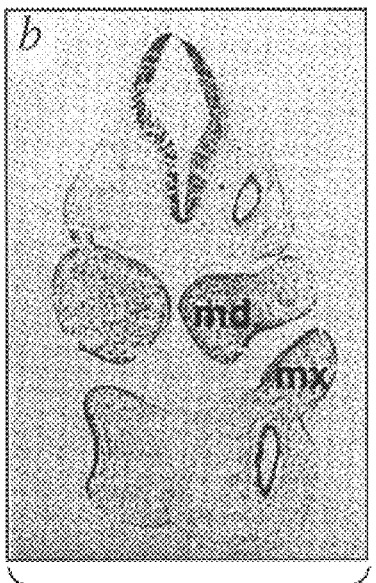
Figure 6C:
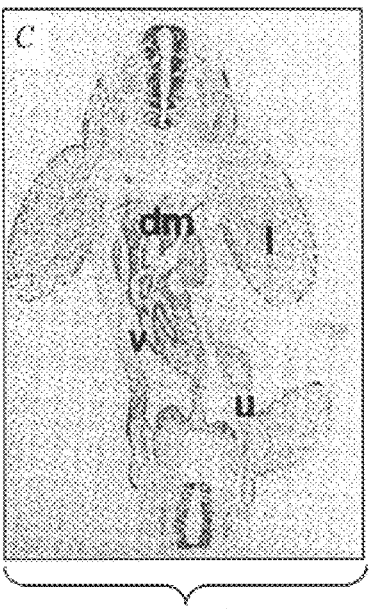
Figures 6D, 6E, 6F:
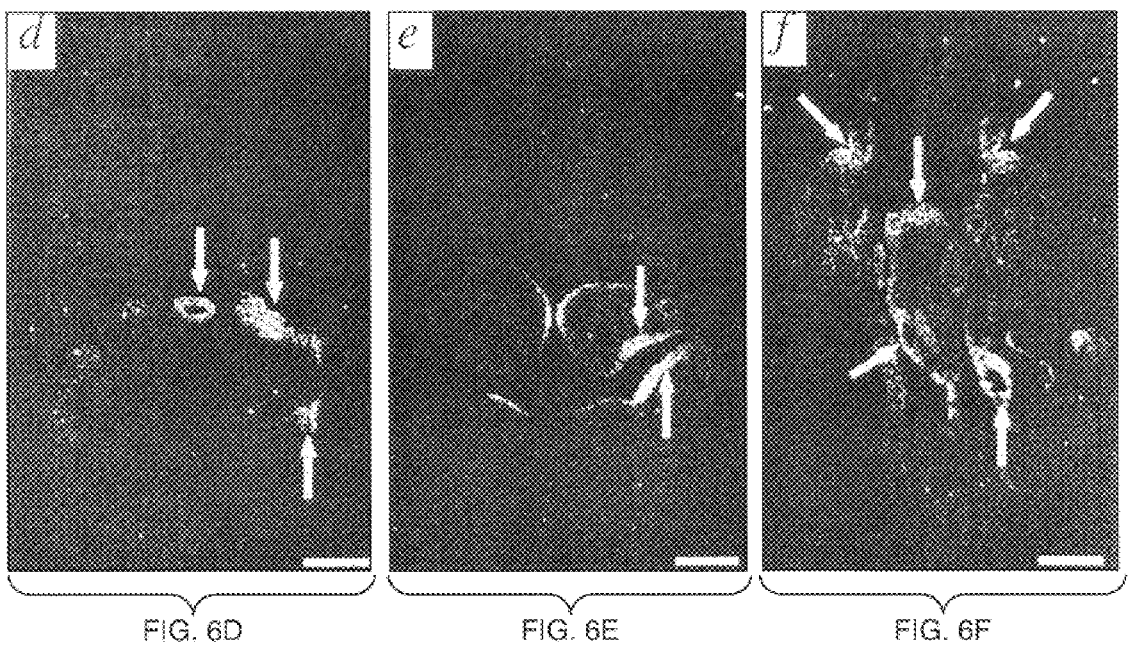

Amplification with primer set 1 revealed a variant band in each of three probands (FIGS. 5a, b, c); two familial cases which showed cosegregation of SSCP variants and phenotype, and a third case that was a de novo Rieger phenotype mutation. In family 1 sequencing identified a missense mutation T394A, that changes the CTG codon for Leu into a CAG codon for Gln in the first helix of the homeodomain. In family 2 a G-to-C point mutation was found at position +5 of the 5' splice site of the third intron separating parts of the homeobox element. This position is occupied by G in 82% of 5' splice sites, which indicates its importance in the mechanism of splicing (Shapiro, M. B. (1987) *Nucleic Acid Res.* 15:7155–7174). In family 3 the band shift was not obvious, but the band structure consistently looked different from the other bands, and sequencing revealed a point mutation A435C, changing an ACA codon for a Thr residue to a CCA coding for Pro in the second helix of the homeodomain. Amplification with primer set 2 revealed bands with altered mobility in two additional families (FIGS. 5d,e). The mutation in family 4 changes A to G at position −11 in the third intron, which creates an additional acceptor site, AG, 5' from the current one. The nearest 3' acceptor site usually becomes the major site used by splicing machinery (Reed, R. (1989) *Genes Dev.* 3:2113–2123), so that, in this case, an insertion of three additional amino acids and a frame shift would occur in the third helix of the homeodomain. In family 5, where the proband has apparent de novo Rieger syndrome, sequencing identified a missense mutation G505C changing a CGG codon for Arg to a CCG for Pro in the third helix of the homeobox. Amplification with primer set 3 revealed an abnormal band in family 6 (FIG. 2a) that cosegregated with the disease phenotype. Sequencing of DNA from affected individuals in this family identified a point mutation G632A that results in a TGA stop codon in place of a TGG for a Thr residue, resulting in premature termination of the protein 34-a.a. C-terminal of the homeodomain (FIG. 1).

All the SSCP variants for mutations were found to cosegregate with the disease phenotype in families with more than one affected (FIG. 3), and the SSCP variants were not detected in any of the chromosomes from ~200 control individuals (~400 chromosomes) with the same ethnic background as the corresponding Rieger syndrome families (Caucasian for families 1,2,3, 4 and 6 and Filipino for family 5). No SSCP variants were detected in the remaining four classic RGS families with primer pairs spanning the whole RIEG cDNA sequence.

A mouse embryonic carcinoma cDNA library (Stratagene) was screened with the PCR product containing the human RIEG gene sequence form nt 880–1120. Positive clones were identified from secondary screens and sequenced. The longest clone was found to represent partial cDNA sequences homologous to the human clone starting in exon 3 (FIG. 1). The cDNA sequences of the human and mouse genes shared 91% of their nucleotide sequence through the coding region and averaged 85% nucleotide sequence identity in the 3' UTR, with the highest homology −97% seen over 270 nucleotides of (A+T) rich-region of the 3' UTR. Homology at the protein level was found to be 99.2% with 100% homology through the homeodomain region (FIG. 1). Considering the strong nucleotide and amino acid homolog of the isolated mouse cDNA and the human RIEG cDNA this sequence was designated as a partial cDNA sequence of the murine homolog of the human RIEG gene, Rieg.

A 535-bp fragment from teh mouse Rieg cDNA spanning nt 740–1182 and containing mostly the 3' UTR region (the stop codon is located at position 782) was subcloned and used for preparing sense and anti-sense riboprobes for in-situ hybridization experiments. Whole-mount in-situ hybridization in day-11 mouse embryos revealed signal around the eye, the maxillary and mandibular epithelia, at the base of the limb, and in the umbilical cord (FIG. 4). Hybridizaiton on sections through the head and the midgut region of the mouse day-11 embryo detected strone signal in the mesenchyme around the eye, in Rathke's pouch, in the dental lamina, the limb mesenchyme, in the dorsal mesentery, and the vitelline umbilical vessels (FIG. 5). Expresion seen in the eye mesenchyme, dental lamina and umbilical cord is consistent with the role of RIEG gene in the pathogenesis or Rieger syndrome. Expression in the limb mesenchyme and Rathke's pouch is stron in day-11 mouse embryos and suggests this gene may be playing in some hand an CNS abnormalities reported in association with RGS.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. An isolated nucleic acid molecule which encodes a polypeptide set forth in SEQ ID NO: 2, 5, 121, 125, 131, or 135.

2. An isolated nucleic acid molecule of claim 1, which is human nucleotide sequence set forth in SEQ ID NO: 3, 122, 126, 132 or 136.

3. An isolated nucleic acid molecule of claim 1, which comprises the full length nucleotide sequence set forth in SEQ ID NO. 1, 120, 124, 130, or 134.

4. An isolated nucleic acid molecule of claim 1, which comprises the full length nucleotide sequence set forth in SEQ ID NO: 6.

5. An isolated nucleic acid molecule of claim 1, which comprises the full length nucleotide sequence set forth in SEQ ID NO: 4.

6. An isolated nucleic acid of claim 1 encoding a polypeptide comprising the full length amino acid sequence set forth in SEQ ID NO: 2 or 5.

7. An isolated nucleic acid of claim 1 encoding a mutant polypeptide comprising the full length amino acid sequence set forth in SEQ ID NO: 121, 125, 131, or 135.

8. An isolated nucleic acid consisting of nucleotides 584–608 or 609–639 of SEQ ID NO:117, SEQ ID NO:128, SEQ ID NO:129, or the complete complement thereof.

9. An isolated nucleic acid consisting of SEQ ID NO:111, SEQ ID NO:112, SEQ ID NO:113, SEQ ID NO:114, SEQ ID NO:15, SEQ ID NO:116, or the complete complement thereof.

* * * * *